United States Patent
Thanos et al.

(10) Patent No.: US 10,669,347 B2
(45) Date of Patent: *Jun. 2, 2020

(54) ANTIBODIES COMPRISING SITE-SPECIFIC NON-NATURAL AMINO ACID RESIDUES, METHODS OF THEIR PREPARATION AND METHODS OF THEIR USE

(71) Applicant: Sutro Biopharma, Inc., South San Francisco, CA (US)

(72) Inventors: Christopher D. Thanos, Tiburon, CA (US); Leslie McEvoy, Mountain View, CA (US); Gang Yin, South San Francisco, CA (US); Kalyani Penta, Palo Alto, CA (US); Ramesh Baliga, Foster City, CA (US); Sunil Bajad, Fremont, CA (US); Sonia Pollitt, San Mateo, CA (US); Chris Murray, Soquel, CA (US); Alex Steiner, San Francisco, CA (US); Avinash Gill, Emeryville, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/632,192

(22) Filed: Jun. 23, 2017

(65) Prior Publication Data

US 2017/0362334 A1 Dec. 21, 2017

Related U.S. Application Data

(63) Continuation of application No. 13/913,345, filed on Jun. 7, 2013, now Pat. No. 9,738,724.

(60) Provisional application No. 61/657,556, filed on Jun. 8, 2012, provisional application No. 61/725,433, filed on Nov. 12, 2012.

(51) Int. Cl.
| | |
|---|---|
| *A61K 47/68* | (2017.01) |
| *C07K 16/00* | (2006.01) |
| *C07K 16/30* | (2006.01) |
| *C07K 16/32* | (2006.01) |

(52) U.S. Cl.
CPC .......... *C07K 16/30* (2013.01); *A61K 47/6817* (2017.08); *A61K 47/6855* (2017.08); *C07K 16/00* (2013.01); *C07K 16/32* (2013.01); *C07K 2317/52* (2013.01); *C07K 2317/622* (2013.01); *C07K 2317/73* (2013.01); *C07K 2317/92* (2013.01); *C07K 2317/94* (2013.01)

(58) Field of Classification Search
CPC ........ C07K 16/30; C07K 16/32; C07K 16/00; C07K 2317/94; C07K 2317/92; C07K 2317/73; C07K 2317/52; C07K 2039/505; C07K 2317/56; A61K 47/6855; A61K 47/6817; A61K 47/6869; A61K 47/6851; A61K 47/6803

See application file for complete search history.

(56) References Cited

U.S. PATENT DOCUMENTS

| | | |
|---|---|---|
| 4,542,225 A | 9/1985 | Blattler et al. |
| 4,618,492 A | 10/1986 | Blattler et al. |
| 4,625,014 A | 11/1986 | Senter et al. |
| 4,671,958 A | 6/1987 | Rodwell et al. |
| 5,643,575 A | 7/1997 | Martinez et al. |
| 5,932,462 A | 8/1999 | Harris et al. |
| 6,339,142 B1 | 1/2002 | Basey et al. |
| 7,026,440 B2 | 4/2006 | Bentley et al. |
| 7,045,337 B2 | 5/2006 | Schultz et al. |
| 7,083,970 B2 | 8/2006 | Schultz et al. |
| 7,338,789 B2 | 3/2008 | Swartz et al. |
| 7,632,924 B2 | 12/2009 | Cho et al. |
| 7,659,241 B2 | 2/2010 | Senter et al. |
| 7,736,653 B2 | 6/2010 | Kim et al. |
| 7,887,809 B1 | 2/2011 | Garen et al. |
| 8,008,443 B2 | 8/2011 | Dall'Acqua et al. |
| 8,008,453 B2 | 8/2011 | Gegg et al. |
| 8,124,094 B2 | 2/2012 | Kim et al. |
| 8,216,804 B2 | 7/2012 | Schultz et al. |
| 8,618,257 B2 | 12/2013 | Sheffer et al. |
| 8,715,958 B2 | 5/2014 | Goerke et al. |
| 8,937,161 B2 | 1/2015 | Mao et al. |
| 2003/0082575 A1 | 5/2003 | Schultz et al. |
| 2003/0108885 A1 | 7/2003 | Schultz et al. |
| 2005/0260711 A1 | 11/2005 | Datta et al. |
| 2007/0148170 A1 | 6/2007 | Desjarlais et al. |
| 2008/0085277 A1 | 4/2008 | Cho et al. |
| 2008/0317670 A1 | 12/2008 | Miao et al. |

(Continued)

FOREIGN PATENT DOCUMENTS

| | | |
|---|---|---|
| CN | 102627615 A | 8/2012 |
| WO | WO 2002/085923 A3 | 10/2002 |

(Continued)

OTHER PUBLICATIONS

Rudikoff et al., PNAS 79: 1979-1983 (Year: 1982).*

(Continued)

*Primary Examiner* — Phuong Huynh
(74) *Attorney, Agent, or Firm* — Squire Patton Boggs (US) LLP

(57) ABSTRACT

Provided herein are antibodies comprising non-natural amino acid residues at site-specific positions, compositions comprising the antibodies, methods of their production and methods of their use. The antibodies are useful for methods of treatment and prevention, methods of detection and methods of diagnosis.

16 Claims, 17 Drawing Sheets

Specification includes a Sequence Listing.

(56) References Cited

U.S. PATENT DOCUMENTS

| | | |
|---|---|---|
| 2009/0035836 A1 | 2/2009 | Datta et al. |
| 2009/0093405 A1 | 4/2009 | Wallen, III et al. |
| 2009/0110662 A1 | 4/2009 | Breitenkamp et al. |
| 2009/0117100 A1 | 5/2009 | Mao et al. |
| 2009/0258420 A1 | 10/2009 | van Vlijmen et al. |
| 2010/0093082 A1 | 4/2010 | Tian et al. |
| 2010/0098630 A1 | 4/2010 | Miao |
| 2011/0033378 A1 | 2/2011 | Dimasi et al. |
| 2012/0077948 A1 | 3/2012 | Nguyen et al. |
| 2012/0100140 A1 | 4/2012 | Reyes et al. |
| 2014/0046030 A1 | 2/2014 | Thanos et al. |
| 2014/0051836 A1 | 2/2014 | Thanos et al. |
| 2014/0066598 A1 | 3/2014 | Stafford et al. |
| 2014/0127209 A1 | 5/2014 | Grabstein et al. |
| 2015/0017187 A1 | 1/2015 | Thanos et al. |

FOREIGN PATENT DOCUMENTS

| | | |
|---|---|---|
| WO | WO 2004/016778 A1 | 2/2004 |
| WO | WO 2005/047337 A1 | 5/2005 |
| WO | WO 2006/069246 A2 | 6/2006 |
| WO | WO 2006/116260 A2 | 11/2006 |
| WO | WO 2007/041635 A2 | 4/2007 |
| WO | WO 2008/030558 A2 | 3/2008 |
| WO | WO2008030612 A2 | 3/2008 |
| WO | WO 2008/066583 A2 | 6/2008 |
| WO | WO 2008/134761 A2 | 11/2008 |
| WO | WO 2009/052249 A1 | 4/2009 |
| WO | WO 2010/006214 A1 | 1/2010 |
| WO | WO 2010/051056 A2 | 5/2010 |
| WO | WO 2010/139948 A2 | 12/2010 |
| WO | WO 2012/032181 A2 | 3/2012 |
| WO | WO 2013/068874 A1 | 5/2013 |
| WO | WO 2014/065860 A1 | 5/2014 |

OTHER PUBLICATIONS

Wu et al., "An Analysis of the Sequences of the Variable Regions of Bence Jones Proteins and Myeloma Light Chains and their Implications for Antibody Complementarity" J. Exp. Med. 132(2): 211-250; Aug. 1, 1970.

Axup et al., Synthesis of site-specific antibody-drug conjugates using unnatural amino acids, (2012), Proc. Nat. Acad. Sci. USA 109(40):16101-16106.

Balog et al., Synthesis of new 2,2,5,5-Tetramethyl-2,5-dihydro-1H-pyrrol-1-yloxyl Radicals and 2-Substituted-2,5,5-trimethylpyrrolidin-1-yloxyl Radicals Based α-Amino Acids, (2004) SYNLETT 14:2591-2593.

Bazewicz et al., Expanding the Utility of 4-Cyano-L-Phenylalanine as a Vibrational Reporter of Protein Environments (2012) J. Phys. Chem. B 116:10824-10831.

Caldas et al., Humanization of the anti-CD18 antibody 6.7: An unexpected effect of a framework residue in binding to antigen, Molecular Immunology, (2003), vol. 39, pp. 941-952.

Carter, Introduction to current and future protein therapeutics: A protein engineering perspective, Experimental Cell Research (2011) 317(9):1261-1269.

Chen et al., N-Benzylpyroglutamyl-L-phenylalanine Derivatives as VCAM/VLA-4 Antagonists, (2000), Bioorg. & Med. Chem. Let. 10:729-733.

Chien et al., Significant structural and functional change of an antigen-binding site by a distant amino acid substitution: Proposal of a structural mechanism, Proc. Natl. Acad. Sci. USA, (Jul. 1989), vol. 86, pp. 5532-5536.

Chin et al., Addition of p-azido-L-phenylalanine to the genetic code of Escherichia coli (2002) J. Am. Chem. Soc. 124:9026-9027.

Chin et al., An Expanded Eukaryotic Genetic Code (2003) Science 301:964-967.

Colman et al., In Research in Immunology (145(1):33-35, 1994.

Database WPI Week 201310 Thomson Scientific, London, GB; AN 2012-P98574 CN 102 627 615 A (Univ Lanzhou) Aug. 8, 2012.

Delgado et al., The uses and properties of PEG-linked proteins, (1992), Critical Reviews in Therapeutic Drug Carrier Systems 9:249-304.

Gerber et al., The antibody-drug conjugate: an enabling modality for natural product-based cancer therapeutics (2013) Nat. Prod. Rep. 30:625-639.

Giusti et al., Somatic diversification of S107 from an antiphosphocholine to an anti-DNA autoantibody is due to a single base change in its heavy chain variable region, Proc. Natl. Acad. Sci. USA, May 1987, vol. 84, pp. 2926-2930.

Golay et al., Mechanism of action of therapeutic monoclonal antibodies: Promises and pitfalls of in vitro and in vivo assays, Archives of Biochemistry and Biophysics, (2012), vol. 526, pp. 146-153.

Harris, Laboratory synthesis of polyethylene glycol derivatives (1985) Macronol. Chem. Phys. C25:325-373.

Hutchins et al., Site-Specific Coupling and Sterically Controlled Formation of Multimeric Antibody Fab Fragments with Unnatural Amino Acids (2011) J. Mol. Biol. 406:595-603.

International Search Report and Written Opinion in PCT/US2014/046141, dated Jan. 13, 2015, 22 pages.

International Search Report and Written Opinion in PCT/US2014/060169, dated Feb. 4, 2015, 14 pages.

International Search Report and Written Opinion, dated Dec. 20, 2013, in PCT/US2013/057677, 13 pages.

International Search Report and Written Opinion, dated Oct. 24, 2013, in PCT/US2013/047838, 17 pages.

Jeong et al., Site-Specific $^{99m}$Tc-Labeling of Antibody Using Dihydrazinophthalazine (DHZ) Conjugation to Fc Region of Heavy Chain (2004) Arch Pharm Res 27:961-967.

Johansson et al., Azide- and Alkyne-Derivatised α-Amino Acids (2012) Eur. J. Org. Chem. 23:4267-4281.

Jubala et al., CD20 Expression in Normal Canine B Cells and in Canine non-Hodgkin Lymphoma, Vet Pathol, (2005), vol. 42, pp. 468-476.

Kaneko et al., Optimizing Therapeutic Antibody Function (2011) Biodrugs 25:1-11.

Kazane et al., Self-Assembled Antibody Multimers through Peptide Nucleic Acid Conjugation (2013) J. Am. Chem. Soc. 135:340-346.

Kazane et al., Site-specific DNA-antibody conjugates for specific and sensitive immuno-PCR (2012) PNAS 109:3731-3736.

Kiick et al., Incorporation of azides into recombinant proteins for chemoselective modification by the Staudinger ligation (2002) Proc. Nat. Acad. Sci. USA 99:19-24.

Liu et al., Protein evolution with an expanded genetic code (2008) PNAS 105:17688-17693.

Nguyen et al., Genetic Encoding and Labeling of Aliphatic Azides and Alkynes in Recombinant Proteins via a Pyrrolysyl-tRNA Synthetase/tRNA$_{CUA}$ Pair and Click Chemistry (2009) J. Am. Chem. Soc. 131:8720-8721.

Patel et al., Cell-free production of Gaussia princeps luciferase—antibody fragment bioconjugates for ex vivo detection of tumor cells (2009) Biochemical and Biophysical Research Communications 390:971-976.

Reichert, Antibody-based therapeutics to watch in 2011, (2011) mABS 3(1):76-99.

Santi et al., Predictable and tunable half-life extension of therapeutic agents by controlled chemical release from macromolecular conjugates, (2012) PNAS 109(16):6211-6216.

Saxon et al., Cell surface engineering by a modified Staudinger reaction (2000) Science 287:2007-2010.

Schmidt et al., A Need for Speed: Genetic Encoding of Rapid Cycloaddition Chemistries for Protein Labelling in Living Cells (2012) ChemBioChem 13:1553-1557.

Schroeder et al., Structure and function of immunoglobulins, J Allergy Clin Immunol, Feb. 2010, pp. S41-S52.

Scouten, A survey of enzyme coupling techniquesMethods in Enzymology, (1987) Methods in Enzymology 135:30-65.

Seitchik et al., Genetically Encoded Tetrazine Amino Acid Directs Rapid Site-Specific in Vivo Bioorthogonal Ligation with trans-Cyclooctenes (2012) J. Am. Chem. Soc. 134:2898-2901.

(56) References Cited

OTHER PUBLICATIONS

Strohl W., Optimization of Fc-mediated effector functions of monoclonal antibodies (2009) *Current Opinion in Biotechnology* 20:685-691.

Strop et al., Location Matters: Cite of Conjugation Modulates Stability and Pharmacokinetics of Antibody Drug Conjugates (2013) *Chem. & Biol.* 20:161-167.

Vidarsson et al., IgG subclasses and allotypes: from structure to effector functions, *Frontiers in Immunology*; Oct. 2014; vol. 5, article 520, 17 pages.

Wang et al., Bioconjugation by copper(I)-catalyzed azide-alkyne [3+2] cycloaddition, (2003) *J. Am. Chem. Soc.* 125:3192-3193.

Wang et al., Chemistry & Biology 16: 323-336, Mar. 27, 2009.

Winkler et al., Changing the Antigen Binding Specificity by Single Point Mutations of an Anti-p24 (HIV-1) Antibody, *The Journal of Immunology*, (2000), vol. 165, pp. 4505-4514.

Wong et al., Chemical crosslinking and the stabilization of proteins and enzymes (1992) *Enzyme Microb. Technol.* 14:866-874.

Wu et al., J Mol Biol 294: 151-162, 1999.

Yin et al., Aglycosylated antibodies and antibody fragments produced in a scalable in vitro transcription-translation system (2012) *mAbs* 4:217-225.

Young et al., An Evolved Aminoacyl-tRNA Synthetase with Atypical Polysubstrate Specificity (2011) *Biochem.* 50:1894-1900.

Zalevsky et al., Enhanced antibody half-life improves in vivo activity (2010) Nature Biotechnology 28:157-159.

Zalipsky, Functionalized poly(ethylene glycol) for preparation of biologically relevant conjugates (1995) *Bioconjug. Chem.* 6:150-165.

Zawada et al., Microscale to Manufacturing Scale-up of Cell-Free Cytokine Production—A New Approach for Shortening Protein Production Development Timelines (2011) *Biotechnol. Bioeng.* 108(7):1570-1578.

* cited by examiner

Figure 11A: DBCO-MMAF 2

Figure 11B: DBCO-DM4

Figure 11C: DBCO-DM4 2

Figure 11D: DBCO-MMAE

ANTIBODIES COMPRISING SITE-SPECIFIC NON-NATURAL AMINO ACID RESIDUES, METHODS OF THEIR PREPARATION AND METHODS OF THEIR USE

CROSS-REFERENCE TO RELATED APPLICATIONS

This application is a continuation of U.S. application Ser. No. 13/913,345, filed Jun. 7, 2013, and now issued as U.S. Pat. No. 9,738,724, which claims the benefit under 35 U.S.C. § 119(e) of U.S. Provisional Application No. 61/657,556, filed Jun. 8, 2012, and U.S. Provisional Application No. 61/725,433, filed Nov. 12, 2012. The disclosures of each of the foregoing applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jun. 23, 2017, is named Sequence_Listing.txt and is 19,049 bytes in size.

FIELD

Provided herein are antibodies comprising non-natural amino acid residues at site-specific positions, compositions comprising the antibodies, methods of their production and methods of their use.

BACKGROUND

Antibodies are biological molecules with remarkable affinity for their target antigens. Nature provides antibodies as part of a defense system in certain vertebrates for the elimination or destruction of foreign proteins, cells and organisms. If a certain vertebrate is presented with a foreign protein on, for example, an infected cell or an infectious bacterium, an antibody can bind its target foreign protein to direct the foreign entity to its elimination or destruction.

The selective affinity of antibodies can be used by man to target nearly any antigen desired. The antigen can be a protein on an infected cell or infectious microorganism. It can also be, for example, a protein on a cancer cell, a protein on a cell of a target tissue, a protein in the bloodstream, a protein on an inflamed or inflammatory cell or any other protein whose selective binding is useful. Antibodies have thus found use in therapy for conditions such as cancer, inflammatory diseases, autoimmune diseases and transplant rejection. The antibody can signal the immune system to destroy or eliminate a diseased cell, or an engineered antibody can carry a molecular payload to destroy the target. In certain applications therapeutic antibodies are linked to molecular shields to increase their lifetime within an organism. Antibodies have also found use as diagnostics. These antibodies can carry a label to indicate the presence of a target antigen on a cell or in a tissue. These labels are typically linked to the antibodies by covalent bonds.

To date, techniques for linking antibodies molecular entities such as molecular payloads, molecular shields and labels have been limited by their heterogeneity in degree and location of linking to the antibodies, by their low yields and by losses in activity. Typical conjugation sites include random locations on antibody chains, e.g. random amines on amino acid side chains, and the N-terminus of certain antibody chains. In such techniques, some antibodies might be linked to the conjugate at one location while some antibodies are linked to the same conjugate at another location, and some antibodies might not be linked at all.

There is a need for antibodies modified at site-specific positions optimized for uniformity, yield and/or activity to further the promising use of antibodies in, for example, therapy and diagnostics.

SUMMARY

Provided herein are antibodies modified at one or more site-specific positions with one or more non-natural amino acid residues. These site-specific positions are optimal for substitution of a natural amino acid residue with a non-natural amino acid residue. In certain embodiments, substitution at these site-specific positions yields antibodies that are uniform in substitution, i.e. that are substantially modified in the selected position. In certain embodiments, an antibody substituted at one or more of these site-specific positions has advantageous production yield, advantageous solubility, advantageous binding and/or advantageous activity. The properties of these antibodies are described in detail in the sections below.

In one aspect, provided herein are antibodies comprising a polypeptide chain having at least one non-natural amino acid residue at a position in the polypeptide chain that is optimally substitutable. The antibody can be any polypeptide or multimeric polypeptide recognized as an antibody to those of skill in the art. The polypeptide chain can be any polypeptide chain of the antibody, including any heavy chain and any light chain. The position in the polypeptide chain that is optimally substitutable is any position in the polypeptide chain that can provide a substitution with optimal yield, uniformity, solubility, binding and/or activity. The sections below describe in detail the optimally substitutable positions of such polypeptide chains. Also described below are useful antibodies useful non-natural amino acids.

In another aspect, provided herein are compositions comprising said antibodies. Advantageously, such compositions can have high uniformity because of the uniformity of the substitution of the antibodies provided herein. In certain embodiments, the compositions comprise a substantial amount of the antibody when measured by total weight of protein or when measured by total weight of antibody. In certain embodiments, the compositions comprise at least 80% of the antibody, at least 85% of the antibody, at least 90% of the antibody or at least 95% of the antibody by weight.

In another aspect, provided herein are methods of making the antibodies. The antibodies can be made by any technique apparent to those of skill in the art for incorporating non-natural amino acids into site-specific positions of antibody chains. In certain embodiments, the antibodies are made by solid phase synthesis, semi-synthesis, in vivo translation, in vitro translation or cell-free translation.

In another aspect, provided herein are methods of using the antibodies for therapy. Antibodies directed to a therapeutic target can incorporate one or more site-specific non-natural amino acids according to the description herein. These antibodies can be used for treating or preventing a disease or condition associated with the therapeutic target. Advantageously, a site-specific non-natural amino acid can be used to link the antibody to a therapeutic payload to facilitate efficacy. Exemplary antibodies, therapeutic targets and diseases or conditions are described herein.

In another aspect, provided herein are methods of using the antibodies for detection. Antibodies directed to a detection target can incorporate one or more site-specific non-natural amino acids according to the description herein. These antibodies can be used with a label to signal binding to the detection target. Advantageously, a site-specific non-natural amino acid can be used to link the antibody to a label to facilitate detection. Exemplary antibodies, detection targets and labels are described herein.

In another aspect, provided herein are methods of modifying the stability of antibodies. Antibodies can be modified with a non-natural amino acid as described herein to facilitate linking to a molecular entity that can modify the stability of the antibody. For instance, a site-specific non-natural amino acid can facilitate linking to a molecular shield, for example polyethylene glycol, to increase the stability of an antibody. Exemplary non-natural amino acids and linking moieties are described herein.

DESCRIPTION OF EXEMPLARY EMBODIMENTS

Figure 1:
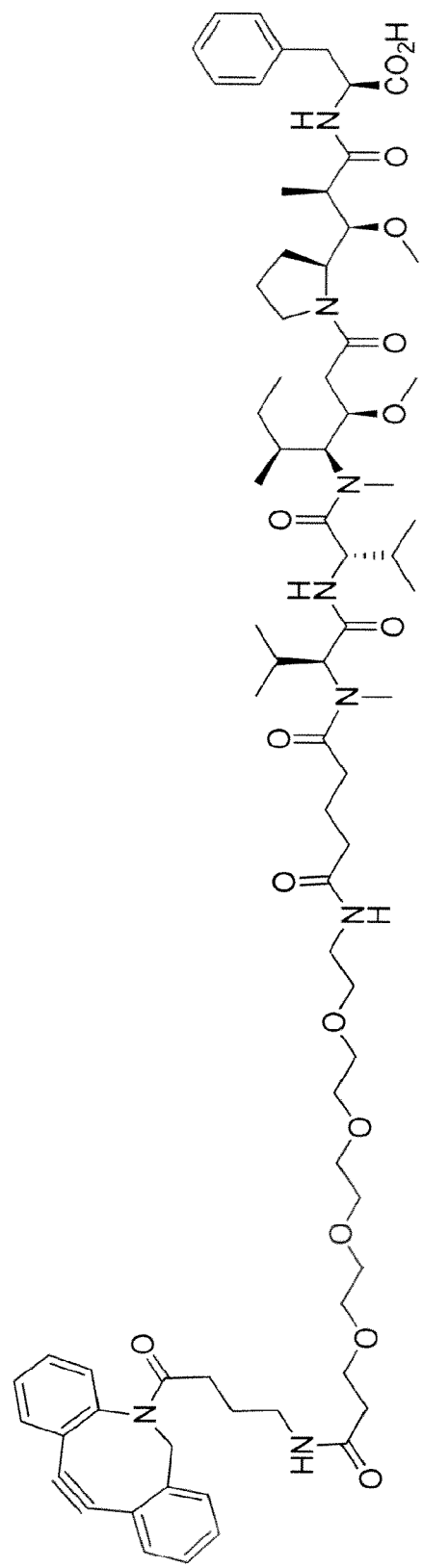
FIG. 1 provides the structure of exemplary cytotoxic reagent DBCO-NIMAF.
Figure 2:
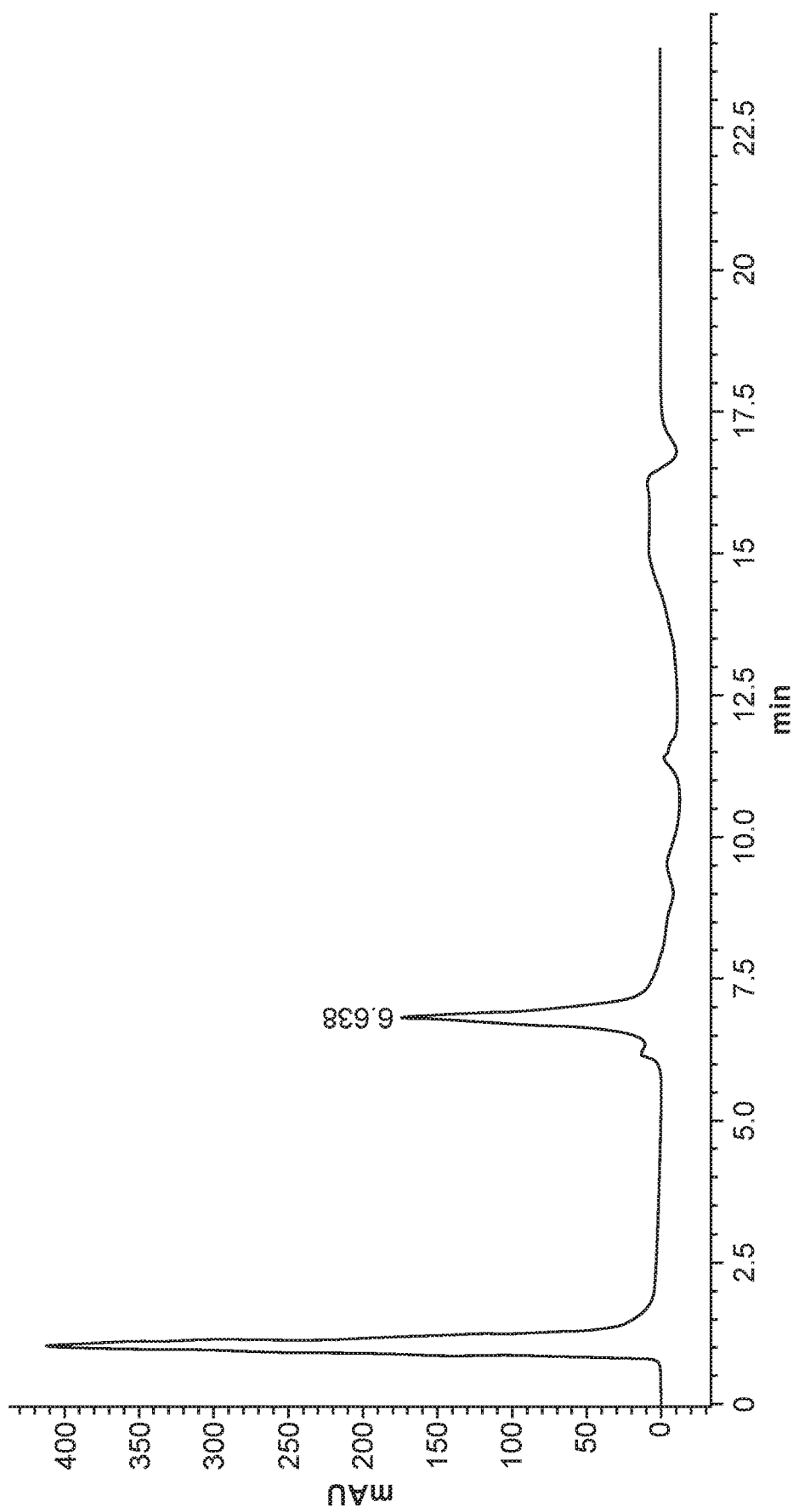
FIG. 2 provides a single peak hydrophobic interaction chromatography (HIC) assay profile.
Figure 3:
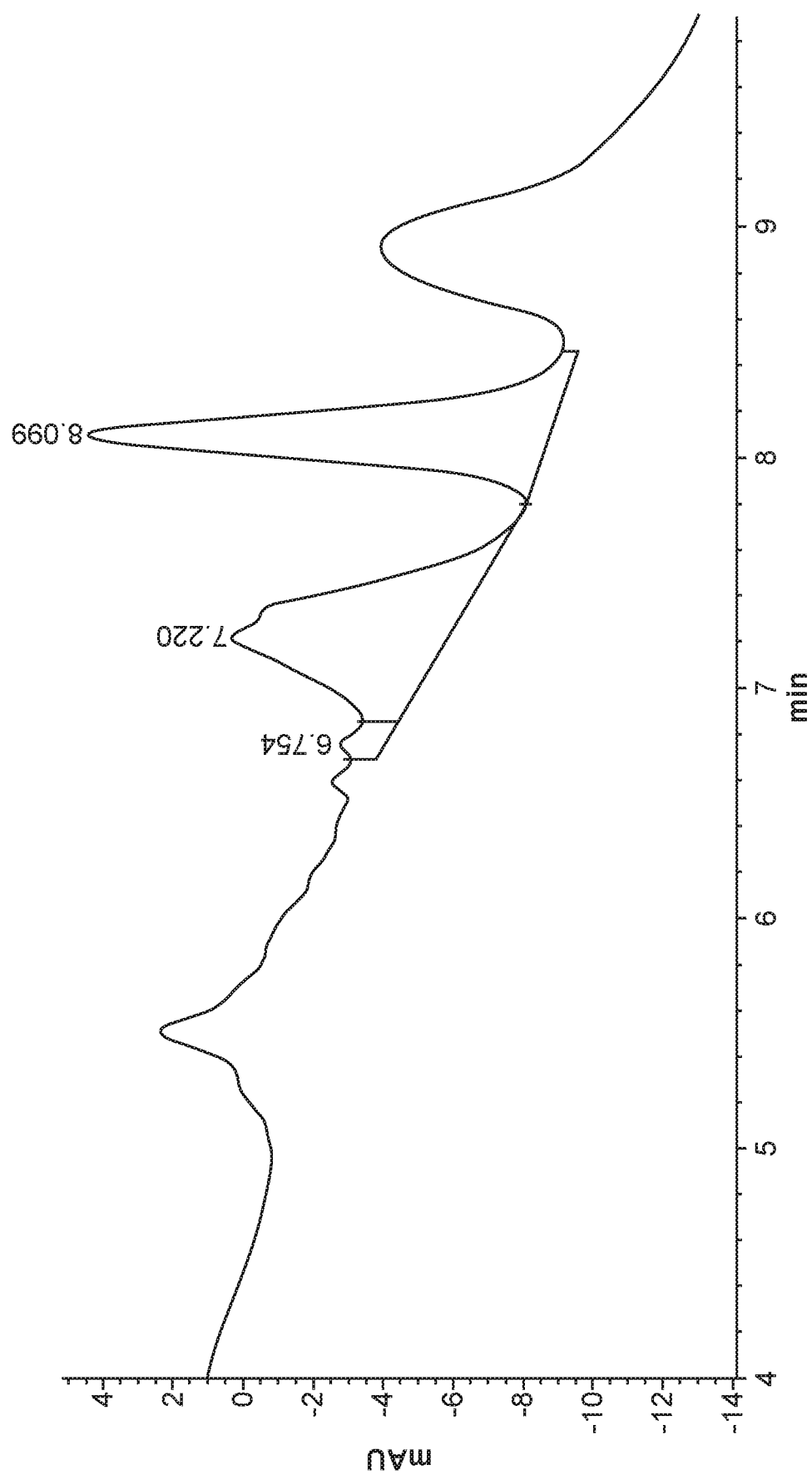
FIG. 3 provides a not-well-resolved (NWR) HIC assay profile.
Figure 4:
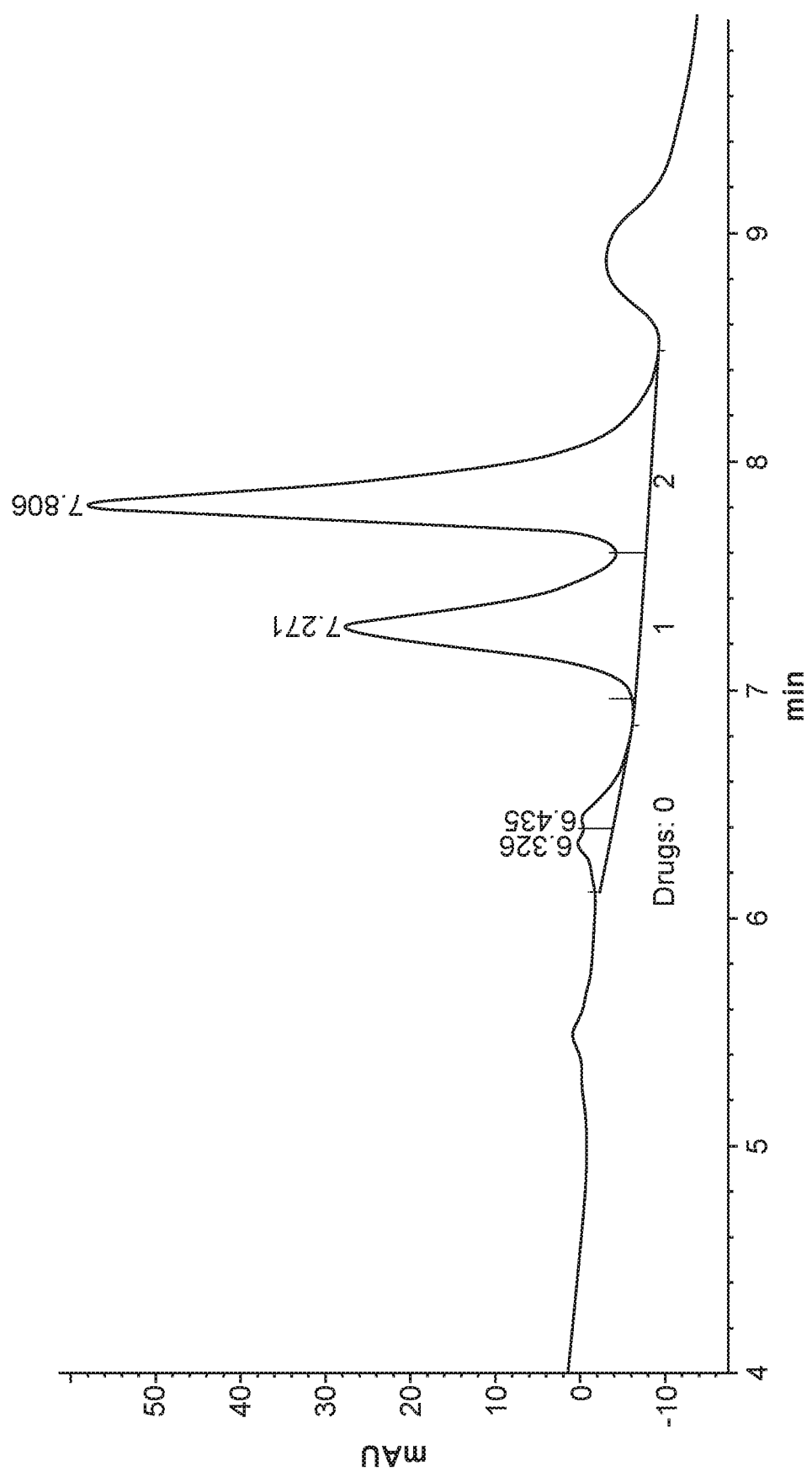
FIG. 4 provides a well-resolved (WR) HIC assay profile.

Provided herein are antibodies having non-natural amino acids at one or more site-specific positions, compositions comprising the antibodies, methods of making the antibodies, and methods of their use.

Definitions

When referring to the antibodies provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

As used herein, the singular forms "a," "an," and "the" include the plural reference unless the context clearly indicates otherwise. Thus, for example, reference to an "antibody" is a reference to one or more such antibodies, etc.

The term "substantially pure" with respect to a composition comprising an antibody refers to a composition that includes at least 80, 85, 90 or 95% by weight or, in certain embodiments, 95, 98, 99 or 100% by weight, e.g. dry weight, of the antibody relative to the remaining portion of the composition. The weight percentage can be relative to the total weight of protein in the composition or relative to the total weight of antibodies in the composition. Purity can be determined by techniques apparent to those of skill in the art, for instance SDS-PAGE.

The term "isolated" refers to an antibody that is substantially or essentially free of components that normally accompany or interact with the antibody as found in its naturally occurring environment or in its production environment, or both. Isolated antibody preparations have less than about 30%, less than about 25%, less than about 20%, less than about 15%, less than about 10%, less than about 5%, less than about 4%, less than about 3%, less than about 2% or less than about 1% of contaminating protein by weight, e.g. dry weight.

The term "antibody" refers to any macromolecule that would be recognized as an antibody by those of skill in the art. Antibodies share common properties including binding and at least one polypeptide chain that is substantially identical to a polypeptide chain that can be encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibodies and antibody fragments recognized by those of skill in the art, and variants thereof. The term further includes glycosylated and aglycosylated antibodies.

The term "antibody fragment" refers to any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, and the like (Maynard & Georgiou, 2000, *Annu. Rev. Biomed. Eng.* 2:339-76; Hudson, 1998, *Curr. Opin. Biotechnol.* 9:395-402).

The term "immunoglobulin (Ig)" refers to a protein consisting of one or more polypeptides substantially encoded by one of the immunoglobulin genes, or a protein substantially identical thereto in amino acid sequence. Immunoglobulins include but are not limited to antibodies. Immunoglobulins may have a number of structural forms, including but not limited to full-length antibodies, antibody fragments, and individual immunoglobulin domains including but not limited to $V_H$, Cγ1, Cγ2, Cγ3, $V_L$, and $C_L$.

The term "immunoglobulin (Ig) domain" refers to a protein domain consisting of a polypeptide substantially encoded by an immunoglobulin gene. Ig domains include but are not limited to $V_H$, Cγ1, Cγ2, Cγ3, $V_L$, and $C_L$.

The term "variable region" of an antibody refers to a polypeptide or polypeptides composed of the $V_H$ immunoglobulin domain, the $V_L$ immunoglobulin domains, or the $V_H$ and $V_L$ immunoglobulin domains. Variable region may refer to this or these polypeptides in isolation, as an Fv fragment, as a scFv fragment, as this region in the context of a larger antibody fragment, or as this region in the context of a full-length antibody or an alternative, non-antibody scaffold molecule.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three or four CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not typically involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ and μ, respectively. Of the various human immunoglobulin classes, only human IgG1, IgG2, IgG3 and IgM are known to activate complement.

The term "variant protein sequence" refers to a protein sequence that has one or more residues that differ in amino acid identity from another similar protein sequence. Said similar protein sequence may be the natural wild type protein sequence, or another variant of the wild type sequence. Variants include proteins that have one or more amino acid insertions, deletions or substitutions. Variants also include proteins that have one or more post-translationally modified amino acids.

The term "parent antibody" refers to an antibody known to those of skill in the art that is modified according to the description provided herein. The modification can be physical, i.e., chemically or biochemically replacing or modifying one or more amino acids of the parent antibody to yield an antibody within the scope of the present description. The modification can also be conceptual, i.e., using the sequence of one or more polypeptide chains of the parent antibody to design an antibody comprising one or more site-specific non-natural amino acids according to the present description. Parent antibodies can be naturally occurring antibodies or antibodies designed or developed in a laboratory. Parent antibodies can also be artificial or engineered antibodies, e.g., chimeric or humanized antibodies.

The term "conservatively modified variant" refers to an antibody that differs from a related antibody by conservative substitutions in amino acid sequence. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins: Structures and Molecular Properties (W H Freeman & Co.; 2nd edition (December 1993)

The terms "identical" or "identity," in the context of two or more polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. The identity can exist over a region that is at least about 50 amino acids or nucleotides in length, or over a region that is 75-100 amino acids or nucleotides in length, or, where not specified, across the entire sequence or a polypeptide. In the case of antibodies, identity can be measured outside the variable CDRs. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Ausubel et al., Current Protocols in Molecular Biology (1995 supplement)).

Examples of algorithms that are suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength (E) of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "amino acid" refers to naturally occurring and non-naturally occurring amino acids, as well as imino acids such as proline, amino acid analogs and amino acid mimetics that function in a manner similar to the naturally occurring amino acids.

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids.

The term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

A "functional Releasing Factor 1 (RF1) protein" refers to RF1 that retains activity equal to or substantially similar to wild-type or unmodified RF1 protein. Functional RF1 activity can be tested, for example, by measuring the growth rate of bacteria expressing the modified RF1 protein, and comparing the growth rate to bacteria expressing wild-type or unmodified RF1. Functional RF1 activity can also be tested, for example, by the ability of the modified RF1 protein to reduce orthogonal tRNA incorporation of a nnAA at a specified position in an mRNA encoding a target protein, thereby increasing the amount of premature chain termination (i.e., increasing the amount of truncated protein).

An "attenuated Releasing Factor 1 (RF1) protein" refers to a modified RF1 that retains reduced activity relative to wild-type or unmodified RF1 protein. RF1 activity can be tested, for example, by measuring the growth rate of bacteria expressing the modified RF1 protein, and comparing the growth rate to bacteria expressing wild-type or unmodified RF1. RF1 activity can also be tested, for example, by the ability of the modified RF1 protein to reduce orthogonal tRNA incorporation of a nnAA at a specified position in an mRNA encoding a target protein, thereby increasing the amount of premature chain termination (i.e., increasing the amount of truncated protein). In some embodiments, the attenuated RF1 protein comprises transcriptional modifications; for example, the expression level of the RF1 protein (wild type or modified) can be reduced to achieve attenuation. The reduction can also achieved by using RNAi technologies. In some embodiments, the attenuated RF1 protein comprises translational modifications; for example, the amount of the synthesized RF1 protein (wild type or modified) can be reduced to achieve attenuation, e.g., by increasing the rate at which the protein is digested by protease via insertion of protease-specific sequence into the RF1 sequence.

Antibodies

Provided herein are antibodies comprising one or more non-natural amino acid residues at site-specific positions in the amino acid sequence of at least one polypeptide chain.

The antibody can share high sequence identity with any antibody recognized by those of skill in the art, i.e. a parent antibody. In certain embodiments, the amino acid sequence of the antibody is identical to the amino acid sequence of the parent antibody, other than the non-natural amino acids at site-specific position. In further embodiments, the antibody provided herein can have one or more insertions, deletions or mutations relative to the parent antibody in addition to the one or more non-natural amino acids at the site-specific positions. In certain embodiments, the antibody provided herein can have a unique primary sequence, so long as it would be recognized as an antibody by those of skill in the art.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e. antigens.

The antibodies provided herein can have any antibody form known to those of skill in the art. They can be full-length, or fragments. Exemplary full length antibodies include IgA, IgA1, IgA2, IgD, IgE, IgG, IgG1, IgG2, IgG3, IgG4, IgM, etc. Exemplary fragments include Fv, Fab, Fc, sFv, etc.

The antibodies provided herein comprise at least one non-natural amino acid. The non-natural amino acid can be any non-natural amino acid known to those of skill in the art. Exemplary non-natural amino acids are described in the sections below.

The non-natural amino acids are positioned at select locations in a polypeptide chain of the antibody. These locations were identified as providing optimum sites for substitution with the non-natural amino acids. Each site is capable of bearing a non-natural amino acid with optimum structure, function and/or methods for producing the antibody.

In certain embodiments, a site-specific position for substitution provides an antibody that is stable. Stability can be measured by any technique apparent to those of skill in the art.

In certain embodiments, a site-specific position for substitution provides an antibody that is has optimal functional properties. For instance, the antibody can show little or no loss of binding affinity for its target antigen compared to an antibody without the site-specific non-natural amino acid. In certain embodiments, the antibody can show enhanced binding compared to an antibody without the site-specific non-natural amino acid.

In certain embodiments, a site-specific position for substitution provides an antibody that can be made advantageously. For instance, in certain embodiments, the antibody shows advantageous properties in its methods of synthesis, discussed below. In certain embodiments, the antibody can show little or no loss in yield in production compared to an antibody without the site-specific non-natural amino acid. In certain embodiments, the antibody can show enhanced yield in production compared to an antibody without the site-specific non-natural amino acid. In certain embodiments, the antibody can show little or no loss of tRNA suppression, described below, compared to an antibody without the site-specific non-natural amino acid. In certain embodiments, the antibody can show enhanced tRNA suppression, described below, in production compared to an antibody without the site-specific non-natural amino acid.

In certain embodiments, a site-specific position for substitution provides an antibody that has advantageous solubility. In certain embodiments, the antibody can show little or no loss in solubility compared to an antibody without the site-specific non-natural amino acid. In certain embodiments, the antibody can show enhanced solubility compared to an antibody without the site-specific non-natural amino acid.

In certain embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In certain embodiments, a site-specific position for substitution provides an antibody that has advantageous folding. In certain embodiments, the antibody can show little or no loss in proper folding compared to an antibody without the site-specific non-natural amino acid. In certain embodiments, the antibody can show enhanced folding compared to an antibody without the site-specific non-natural amino acid.

In certain embodiments, a site-specific position for substitution provides an antibody that is capable of advantageous conjugation. As described below, several non-natural amino acids have side chains or functional groups that facilitate conjugation of the antibody to a second agent, either directly or via a linker. In certain embodiments, the antibody can show enhanced conjugation efficiency compared to an antibody without the same or other non-natural amino acids at other positions. In certain embodiments, the antibody can show enhanced conjugation yield compared to an antibody without the same or other non-natural amino acids at other positions. In certain embodiments, the antibody can show enhanced conjugation specificity compared to an antibody without the same or other non-natural amino acids at other positions.

The one or more non-natural amino acids are located at selected site-specific positions in at least one polypeptide chain of the antibody. The polypeptide chain can be any polypeptide chain of the antibody without limitation, including either light chain or either heavy chain. The site-specific position can be in any domain of the antibody, including any variable domain and any constant domain.

In certain embodiments, the antibodies provided herein comprise one non-natural amino acid at a site-specific position. In certain embodiments, the antibodies provided herein comprise two non-natural amino acids at site-specific positions. In certain embodiments, the antibodies provided herein comprise three non-natural amino acids at site-specific positions. In certain embodiments, the antibodies provided herein comprise more than three non-natural amino acids at site-specific positions.

The site-specific positions for substituting can be described with any antibody nomenclature system known to those of skill in the art. In the Kabat numbering system, these positions are at heavy chain residues H005, H023, H042, H065, H074, and H084. In the EU numbering system, these positions are at heavy chain residues H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H342, H344, H355, H356, H358, H359, H360, H375, H383, H384, H386, H389, H392, H398, H404, H420, H421, H436, and H438. In other words, provided herein are antibodies comprising one or more non-natural amino acids at one or more positions selected from Kabat residues H005, H023, H042, H065, H074, and H084; and EU residues H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H342, H344, H355, H356, H358, H359, H360, H375, H383, H384, H386, H389, H392, H398, H404, H420, H421, H436, and H438.

In certain embodiments, provided herein are antibodies comprising one or more non-natural amino acids at one or more positions selected from Kabat residues H005, H023, H074, and H084; and EU residues H118, H119, H132, H134, H135, H136, H137, H139, H160, H162, H165, H172, H191, H194, H239, H241, H246, H267, H268, H269, H270, H271, H272, H274, H275, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H342, H344, H355, H359, H375, H386, H389, H392, H398, H404, H420, H421, and H438.

In certain embodiments, provided herein are antibodies comprising one or more non-natural amino acids at one or more positions selected from Kabat residues H005, H023, and H084; and EU residues H118, H119, H132, H134, H136, H137, H160, H162, H172, H239, H241, H267, H269, H270, H271, H272, H282, H286, H292, H293, H296, H298, H329, H330, H334, H335, H340, H355, H359, H386, H389, H404, H420, H421, H438, and H342.

In certain embodiments, provided herein are antibodies comprising one or more non-natural amino acids at one or more positions selected from Kabat residues H005 and H084; and EU residues H118, H132, H136, H239, H293, H334, H355, H359, and H389.

In certain embodiments, provided herein are antibodies comprising one or more non-natural amino acids at one or more positions selected from Kabat residues H023 and H074; and EU residues H119, H134, H135, H137, H139, H160, H162, H165, H172, H191, H194, H241, H246, H267, H268, H269, H270, H271, H272, H274, H275, H280, H281, H282, H283, H286, H289, H292, H294, H295, H296, H297, H298, H299, H300, H301, H303, H305, H317, H320, H324, H326, H327, H329, H330, H332, H333, H335, H337, H339, H342, H344, H355, H375, H386, H392, H398, H404, H420, H421, H340 and H438.

In certain embodiments, provided herein are antibodies comprising one or more non-natural amino acids at one or more positions selected from Kabat residues H042 and H065; and EU residues H138, H155, H174, H176, H177, H219, H238, H243, H262, H264, H265, H278, H342, H356, H358, H360, H383, H384 H404, and H436.

In certain embodiments, provided herein are antibodies comprising one or more non-natural amino acids at one or more positions selected from EU residues corresponding to H292-H301, H303, and H305.

In the Chothia numbering system, these positions are at heavy chain residues H005, H023, H042, H065, H074, and H084. In the EU numbering system, these positions are at heavy chain residues H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H342, H344, H355, H356, H358, H359, H360, H375, H383, H384, H386, H389, H392, H398, H404, H420, H421, H436, and H438. In other words, provided herein are antibodies comprising one or more non-natural amino acids at one or more positions selected from Chothia residues H005, H023, H042, H065, H074, and H084; and EU residues H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H342, H344, H355, H356, H358, H359, H360, H375, H383, H384, H386, H389, H392, H398, H404, H420, H421, H436, and H438.

In certain embodiments, provided herein are antibodies comprising one or more non-natural amino acids at one or more positions selected from Chothia residues H005, H023, H074, and H084; and EU residues H118, H119, H132, H134, H135, H136, H137, H139, H160, H162, H165, H172, H191, H194, H239, H241, H246, H267, H268, H269, H270, H271, H272, H274, H275, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H342, H344, H355, H359, H375, H386, H389, H392, H398, H404, H420, H421, and H438.

In certain embodiments, provided herein are antibodies comprising one or more non-natural amino acids at one or more positions selected from Chothia residues H005, and H084; and EU residues H118, H132, H136, H239, H293, H334, H342, H355, H359, H389 and H404.

In certain embodiments, provided herein are antibodies comprising one or more non-natural amino acids at one or more positions selected from EU residues corresponding to H292-H301, H303, and H305.

In certain embodiments, provided herein are antibodies comprising one or more non-natural amino acids at one or more positions selected from Chothia residues H023 and H074; and EU residues H119, H134, H135, H137, H139, H160, H162, H165, H172, H191, H194, H241, H246, H267, H268, H269, H270, H271, H272, H274, H275, H280, H281, H282, H283, H286, H289, H292, H294, H295, H296, H297, H298, H299, H300, H301, H303, H305, H317, H320, H324, H326, H327, H329, H330, H332, H333, H335, H337, H339, H342, H344, H355, H375, H386, H392, H398, H420, H421, H340, H404, and H438.

In certain embodiments, provided herein are antibodies comprising one or more non-natural amino acids at one or more positions selected from Chothia residues H042 and H065; and EU residues H138, H155, H174, H176, H177, H219, H238, H243, H262, H264, H265, H278, H342, H356, H358, H360, H383, H384, H404, and H436.

In certain embodiments, provided herein are antibodies comprising one or more non-natural amino acids at one or more positions selected from residues H005, H023, and H084 according to the Kabat or Chothia numbering scheme; and residues H118, H119, H132, H134, H136, H137, H160, H162, H172, H239, H241, H267, H269, H270, H271, H272, H282, H286, H292, H293, H296, H298, H329, H330, H334, H335, H340, H355, H359, H386, H389, H404, H420, H421, H438, and H342, according to the EU numbering scheme.

In certain embodiments, provided herein are antibodies comprising one or more non-natural amino acids at one or more positions selected from residues L043, L049, L056, L057, L060, L067, and L068, according to the Kabat or Chothia numbering scheme; and residues L109, L112, L114, L144, L153, L156, L157, L168, L184, L202, L203, and L206, according to the EU numbering scheme. In certain embodiments, provided herein are antibodies comprising one or more non-natural amino acids at one or more positions selected from residues L043, L049, L056, L057, L060, L067, and L068, according to the Kabat or Chothia numbering scheme; and residues L109, L112, L114, L144, L153, L156, L168, L184, L202, and L203, according to the EU numbering scheme. In certain embodiments, provided herein are antibodies comprising one or more non-natural amino acids at one or more positions selected from residues L043, L049, L056, L057, L060, L067, and L068, according to the Kabat or Chothia numbering scheme; and residues L109, L144, L153, L156, L184, L202, and L203, according to the EU numbering scheme. In certain embodiments, provided herein are antibodies comprising one or more non-natural amino acids at one or more positions selected from residues L049, L056, L057, L060, and L067, according to the Kabat or Chothia numbering scheme; and residues L109, L153, L202, and L203, according to the EU numbering scheme.

In certain embodiments, provided herein are antibodies comprising one or more non-natural amino acids at one or more positions selected from residues H023 and H084, according to the Kabat or Chothia numbering scheme; and residues H118, H119, H135, H136, H137, H160, H161, H162, H164, H195, H197, H219, H282, H289, H296, H330, H335, H361, H400, H404, H422, H440, H260, H267, H268, H272, H274, H292, H293, H297, H298, H303, H305, H332, H333, H334, H340, H341, H342, H343, H355, H362, H386, H392, H404, H424, H438, H442 and H443, according to the EU numbering scheme. In certain embodiments, provided herein are antibodies comprising one or more non-natural amino acids at one or more positions selected from residues H023 and H084, according to the Kabat or Chothia numbering scheme; and residues H118, H119, H135, H136, H137, H160, H161, H162, H164, H195, H197, H219, H282, H296, H335, H361, H422, H440, H267, H272, H274, H293, H297, H298, H303, H305, H334, H340, H341, H342, H343, H355, H362, H392, H404, H424, H438, H442 and H443, according to the EU numbering scheme. In certain embodiments, provided herein are antibodies comprising one or more non-natural amino acids at one or more positions selected from residues H023 and H084, according to the Kabat or Chothia numbering scheme; and residues H118, H119, H135, H136, H137, H160, H161, H162, H195, H197, H219, H282, H296, H422, H440, H267, H272, H293, H297, H298, H303, H305, H334, H340, H341, H342, H355, H392, H404, H424, H438, H442 and H443, according to the EU numbering scheme. In certain embodiments, provided herein are antibodies comprising one or more non-natural amino acids at one or more positions selected from residues H023 and H084, according to the Kabat or Chothia numbering scheme; and residues H118, H119, H135, H136, H160, H162, H195, H219, H282, H296, H267, H293, H297, H298, H303, H305, H334, H340, H341, H392, and H438, H442, according to the EU numbering scheme.

In certain embodiments, provided herein are antibodies comprising one or more non-natural amino acids at one or more positions selected from residues H042, H003, H007, H014, H016, H019, H025, H040, H043, H051, H052, H053, H056, H070, H082A, H098, H100, H110, and H112, according to the Kabat or Chothia numbering scheme; and residues H121, H180, H184, H190, H192, H214, H216, H221, H222, H225, H227, H230, H231, H232, and H236, according to the EU numbering scheme. In certain embodiments, provided herein are antibodies comprising one or more non-natural amino acids at one or more positions selected from residues H042, H003, H007, H014, H016, H019, H025, H040, H043, H052, H053, H056, H070, H082A, H100, H110, and H112, according to the Kabat or Chothia numbering scheme; and residues H121, H180, H190, H192, H214, H216, H221, H222, H225, H227, H230, H231, H232, and H236, according to the EU numbering scheme. In certain embodiments, provided herein are antibodies comprising one or more non-natural amino acids at one or more positions selected from residues H042, H003, H007, H014, H016, H019, H025, H040, H043, H052, H070, H082A, H100, H110, and H112, according to the Kabat or Chothia numbering scheme; and residues H121, H180, H190, H192, H214, H216, H221, H222, H225, H227, H230, H231, H232, and H236, according to the EU numbering scheme. In certain embodiments, provided herein are antibodies comprising one or more non-natural amino acids at one or more positions selected from residues H007, H014, H019, H025, H040, H043, H052, H070, H100, H110, and H112, according to the Kabat or Chothia numbering scheme; and residues H121, H180, H214, H216, H222, H227, H230, H231, H232, and H236, according to the EU numbering scheme.

In certain embodiments, provided herein are antibodies comprising one or more non-natural amino acids at one or more positions selected from residues (−)L001, L003, L005, L007, L008, L009, L010, L016, L017, L018, L020, L022, L026, L027, L045, L058, L063, L065, L066, L070, L077, L079, and L107, according to the Kabat or Chothia numbering scheme; and residues L138, L142, L143, L152, L171, L182, L188, L199, and L201, according to the EU numbering scheme. In certain embodiments, provided herein are antibodies comprising one or more non-natural amino acids at one or more positions selected from residues minus 1, L003, L005, L007, L008, L009, L010, L016, L017, L018, L020, L022, L026, L027, L045, L058, L063, L065, L066, L070, L077, L079, and L107, according to the Kabat or Chothia numbering scheme; and residues L142, L143, L152, L171, L182, L188, L199, and L201, according to the EU numbering scheme. In certain embodiments, provided herein are antibodies comprising one or more non-natural amino acids at one or more positions selected from residues (−)L001, L003, L005, L007, L008, L009, L016, L017, L018, L020, L022, L026, L027, L045, L058, L063, L065, L066, L070, L077, L079, and L107, according to the Kabat or Chothia numbering scheme; and residues L142, L152, L171, L182, L188, and L199, according to the EU numbering scheme. In certain embodiments, provided herein are antibodies comprising one or more non-natural amino acids at one or more positions selected from residues minus 1, L005, L007, L008, L016, L017, L018, L020, L022, L027, L045, L058, L063, L077, L079, and L107, according to the Kabat or Chothia numbering scheme; and residues L142, L152, L182, L188, and L199, according to the EU numbering scheme. In certain embodiments, provided herein are antibodies comprising one or more non-natural amino acids at one or more positions selected from residues (−)L001, L016, and L063, according to the Kabat or Chothia numbering scheme; and residue L199, according to the EU numbering scheme.

In certain embodiments, provided herein are antibodies comprising one or more non-natural amino acids at one or more positions selected from residues H019, H025, H051, H070, H098, H110, and H112, according to the Kabat or Chothia numbering scheme; and residues H121, H136, H180, H187, H190, H214, H216, H221, and H222, according to the EU numbering scheme.

In certain embodiments, provided herein are antibodies comprising one or more non-natural amino acids at one or more positions selected from residues (−)L001, L007, L008, L016, L022, L063, L014, and L070, according to the Kabat or Chothia numbering scheme; and residues L138, L142, L143 and L152, according to the EU numbering scheme.

In certain embodiments, provided herein are antibodies comprising one or more non-natural amino acids at one or more positions selected from residues H019, H025, H051, H070, H077, H079, H098, H110, and H112, according to the Kabat or Chothia numbering scheme; and residues H121, H136, H180, H187, H190, H214, H216, H221, and H222, according to the EU numbering scheme.

In certain embodiments, provided herein are antibodies comprising one or more non-natural amino acids at one or more positions selected from residues (−)L001, L007, L008, L016, L022, L063, and L070, according to the Kabat or Chothia numbering scheme; and residues L138, L142, L143, L152 and L201, according to the EU numbering scheme.

The site-specific positions can also be identified relative to the amino acid sequences of the polypeptide chains of a reference antibody. For example, the amino acid sequence of a reference heavy chain is provided at SEQ ID NO:1. In the reference heavy chain, the site-specific positions are at residues 5, 23, 42, 66, 75, 88, 121, 122, 135, 137, 138, 139, 140, 141, 142, 158, 163, 165, 168, 175, 177, 179, 180, 194, 197, 222, 241, 242, 244, 246, 249, 265, 267, 268, 270, 271, 272, 273, 274, 275, 277, 278, 281, 283, 284, 285, 286, 289, 292, 295, 296, 297, 298, 299, 300, 301, 302, 303, 304, 306, 308, 320, 323, 327, 329, 330, 332, 333, 335, 336, 337, 338, 340, 342, 343, 345, 347, 358, 359, 361, 362, 363, 378, 386, 387, 389, 392, 395, 401, 407, 423, 424, 439 and 441. In other words, provided herein are antibodies comprising one or more non-natural amino acids at one or more positions selected from those corresponding to 5, 23, 42, 66, 75, 88, 121, 122, 135, 137, 138, 139, 140, 141, 142, 158, 163, 165, 168, 175, 177, 179, 180, 194, 197, 222, 241, 242, 244, 246, 249, 265, 267, 268, 270, 271, 272, 273, 274, 275, 277, 278, 281, 283, 284, 285, 286, 289, 292, 295, 296, 297, 298, 299, 300, 301, 302, 303, 304, 306, 308, 320, 323, 327, 329, 330, 332, 333, 335, 336, 337, 338, 340, 342, 343, 345, 347, 358, 359, 361, 362, 363, 378, 386, 387, 389, 392, 395, 401, 407, 423, 424, 439 and 441 of the representative heavy chain polypeptide according to SEQ ID NO:1.

In certain embodiments, provided herein are antibodies comprising one or more non-natural amino acids at one or more positions selected from those corresponding to 5, 23, 75, 88, 121, 122, 135, 137, 138, 139, 140, 142, 163, 165, 168, 175, 194, 197, 242, 244, 249, 270, 271, 272, 273, 274, 275, 277, 278, 283, 284, 285, 286, 289, 292, 295, 296, 297, 298, 299, 300, 301, 302, 303, 304, 306, 308, 320, 323, 327, 329, 330, 332, 333, 335, 336, 337, 338, 340, 342, 343, 345, 347, 358, 362, 378, 389, 392, 395, 401, 407, 423, 424, and 441 of the representative heavy chain polypeptide according to SEQ ID NO:1.

In certain embodiments, provided herein are antibodies comprising one or more non-natural amino acids at one or more positions selected from those corresponding to 5, 23, 88, 121, 122, 135, 137, 138, 139, 140, 163, 165, 168, 175, 242, 244, 270, 273, 274, 275, 285, 289, 295, 296, 299, 300, 301, 332, 333, 337, 338, 343, 345, 358, 362, 389, 407, 423, 424, and 441 of the representative heavy chain polypeptide according to SEQ ID NO:1.

In certain embodiments, provided herein are antibodies comprising one or more non-natural amino acids at one or more positions selected from those corresponding to 5, 88, 121, 135, 139, 242, 296, 337, 358, 362, and 392 of the representative heavy chain polypeptide according to SEQ ID NO:1.

In certain embodiments, provided herein are antibodies comprising one or more non-natural amino acids at one or more positions selected from those corresponding to 23, 75, 122, 137, 138, 140, 142, 163, 165, 168, 175, 194, 197, 244, 249, 270, 271, 272, 273, 274, 275, 277, 278, 283, 284, 285, 286, 289, 292, 295, 297, 298, 299, 300, 301, 302, 303, 304, 306, 308, 320, 323, 327, 329, 330, 332, 333, 335, 336, 338, 340, 342, 343, 345, 347, 358, 378, 389, 395, 401, 407, 423, 424, and 441 of the representative heavy chain polypeptide according to SEQ ID NO:1.

In certain embodiments, provided herein are antibodies comprising one or more non-natural amino acids at one or more positions selected from those corresponding to 42, 66, 141, 158, 177, 179, 180, 222, 241, 246, 265, 267, 268, 281, 359, 361, 363, 386, 387, 407, and 439 of the representative heavy chain polypeptide according to SEQ ID NO:1.

In certain embodiments, provided herein are antibodies comprising one or more non-natural amino acids at one or more positions selected from those corresponding to 292-301, 303, and 305 of the representative heavy chain polypeptide according to SEQ ID NO:1.

In certain embodiments, provided herein are antibodies comprising one or more non-natural amino acids at one or more positions selected from those corresponding to 23, 88, 121, 122, 138, 139, 140, 163, 164, 165, 167, 198, 200, 222, 285, 292, 299, 333, 338, 364, 403, 407, 425, 443, 263, 270, 271, 275, 277, 295, 296, 300, 301, 306, 308, 335, 336, 337, 343, 344, 345, 346, 358, 365, 389, 395, 407, 427, 441, 445, and 446 of the representative heavy chain polypeptide according to SEQ ID NO:1.

In certain embodiments, provided herein are antibodies comprising one or more non-natural amino acids at one or more positions selected from those corresponding to 23, 88, 121, 122, 138, 139, 140, 163, 164, 165, 167, 198, 200, 222, 285, 299, 338, 364, 425, 443, 270, 275, 277, 295, 296, 300, 301, 306, 308, 337, 343, 344, 345, 346, 358, 365, 395, 407, 427, 441, 445, and 446 of the representative heavy chain polypeptide according to SEQ ID NO:1.

In certain embodiments, provided herein are antibodies comprising one or more non-natural amino acids at one or more positions selected from those corresponding to 23, 88, 121, 122, 138, 139, 140, 163, 164, 165, 167, 198, 200, 222, 285, 299, 364, 425, 443, 270, 275, 296, 300, 301, 306, 308, 337, 343, 344, 345, 358, 365, 395, 407, 427, 441, 445, and 446 of the representative heavy chain polypeptide according to SEQ ID NO:1.

In certain embodiments, provided herein are antibodies comprising one or more non-natural amino acids at one or more positions selected from those corresponding to 23, 88, 121, 122, 138, 139, 140, 163, 164, 165, 198, 200, 222, 285, 299, 425, 443, 270, 275, 296, 300, 301, 306, 308, 337, 343, 344, 345, 358, 395, 407, 427, 441, 445, and 446 of the representative heavy chain polypeptide according to SEQ ID NO:1.

In certain embodiments, provided herein are antibodies comprising one or more non-natural amino acids at one or more positions selected from those corresponding to 23, 88, 121, 122, 138, 139, 163, 165, 198, 222, 285, 299, 270, 296, 300, 301, 306, 308, 337, 343, 344, 395, 407, and 441 of the representative heavy chain polypeptide according to SEQ ID NO:1.

In certain embodiments, provided herein are antibodies comprising one or more non-natural amino acids at one or more positions selected from those corresponding to 42, 3, 7, 14, 16, 19, 25, 40, 43, 51, 52, 54, 57, 71, 84, 102, 104, 114, 119, 124, 183, 187, 193, 195, 217, 219, 224, 225, 228, 230, 233, 234, 235 and 239 of the representative heavy chain polypeptide according to SEQ ID NO:1.

In certain embodiments, provided herein are antibodies comprising one or more non-natural amino acids at one or more positions selected from those corresponding to 42, 3, 7, 14, 16, 19, 25, 40, 43, 52, 54, 57, 71, 84, 104, 114, 119, 124, 183, 193, 195, 217, 219, 224, 225, 228, 230, 233, 234, 235 and 239 of the representative heavy chain polypeptide according to SEQ ID NO:1.

In certain embodiments, provided herein are antibodies comprising one or more non-natural amino acids at one or more positions selected from those corresponding to 7, 14, 19, 25, 40, 43, 52, 71, 104, 114, 119, 124, 183, 195, 217, 219, 230, 233, 234, 235, and 239 of the representative heavy chain polypeptide according to SEQ ID NO:1.

In certain embodiments, provided herein are antibodies comprising one or more non-natural amino acids at one or more positions selected from those corresponding to minus 1, 3, 5, 7, 8, 9, 10, 16, 17, 18, 20, 22, 26, 27, 45, 58, 63, 65, 66, 70, 77, 79, 107, 138, 142, 143, 152, 171, 182, 188, 199, and 201 of the representative light chain polypeptide according to SEQ ID NO:2.

In certain embodiments, provided herein are antibodies comprising one or more non-natural amino acids at one or more positions selected from those corresponding to minus 1, 3, 5, 7, 8, 9, 16, 17, 18, 20, 22, 26, 27, 45, 58, 63, 65, 66, 70, 77, 79, 107, 142, 143, 152, 171, 182, 188, 199, and 201 of the representative light chain polypeptide according to SEQ ID NO:2.

In certain embodiments, provided herein are antibodies comprising one or more non-natural amino acids at one or more positions selected from those corresponding to minus 1, 3, 5, 7, 8, 9, 16, 17, 18, 20, 22, 26, 27, 45, 58, 63, 65, 66, 70, 77, 79, 107, 142, 152, 171, 182, 188, and 199 of the representative light chain polypeptide according to SEQ ID NO:2.

In certain embodiments, provided herein are antibodies comprising one or more non-natural amino acids at one or more positions selected from those corresponding to minus 1, 5, 7, 8, 16, 17, 18, 20, 22, 27, 45, 58, 63, 77, 79, 107, 142, 152, 182, 188, and 199 of the representative light chain polypeptide according to SEQ ID NO:2.

In certain embodiments, provided herein are antibodies comprising one or more non-natural amino acids at one or more positions selected from those corresponding to minus 1, 16, 63, and 199 of the representative light chain polypeptide according to SEQ ID NO:2.

In certain embodiments, provided herein are antibodies comprising one or more non-natural amino acids at one or more positions selected from those corresponding to 19, 25, 51, 71, 102, 114, 119, 124, 139, 183, 187, 193, 217, 219, 224, and 225 of the representative heavy chain polypeptide according to SEQ ID NO:1.

In certain embodiments, provided herein are antibodies comprising one or more non-natural amino acids at one or more positions selected from those corresponding to minus 1, 7, 8, 16, 22, 63, 14, 70, 138, 142, 143 and 152 of the representative light chain polypeptide according to SEQ ID NO:2.

In certain embodiments, provided herein are antibodies comprising one or more non-natural amino acids at one or more positions selected from those corresponding to 19, 25, 51, 71, 78, 80, 102, 114, 119, 124, 139, 183, 187, 193, 217, 219, 224, and 225 of the representative heavy chain polypeptide according to SEQ ID NO:1.

In certain embodiments, provided herein are antibodies comprising one or more non-natural amino acids at one or more positions selected from those corresponding to minus 1, 7, 8, 16, 22, 63, 70, 138, 142, 143, 152, and 201 of the representative light chain polypeptide according to SEQ ID NO:2.

In certain embodiments, provided herein are antibodies comprising one or more non-natural amino acids at one or more positions selected from those corresponding to 43, 49, 56, 57, 60, 67, 68, 109, 112, 114, 144, 153, 156, 157, 168, 184, 202, 203, and 206 of the representative light chain polypeptide according to SEQ ID NO:2.

In certain embodiments, provided herein are antibodies comprising one or more non-natural amino acids at one or more positions selected from those corresponding to 43, 49, 56, 57, 60, 67, 68, 109, 112, 144, 153, 156, 168, 184, 202, and 203 of the representative light chain polypeptide according to SEQ ID NO:2.

In certain embodiments, provided herein are antibodies comprising one or more non-natural amino acids at one or more positions selected from those corresponding to 43, 49, 56, 57, 60, 67, 68, 109, 144, 153, 156, 184, 202, and 203 of the representative light chain polypeptide according to SEQ ID NO:2.

In certain embodiments, provided herein are antibodies comprising one or more non-natural amino acids at one or more positions selected from those corresponding to 49, 56, 57, 60, 67, 109, 153, 202, and 203 of the representative light chain polypeptide according to SEQ ID NO:2.

In certain embodiments, the antibody comprises a polypeptide chain that can be described by the following formula (I):

$$Xaa^1- \ldots -(Naa^{p(i)})_n- \ldots -Xaa^q \qquad (I).$$

In Formula (I), each Xaa represents an amino acid in the polypeptide chain of any identity. In other words, each Xaa can be any amino acid, typically any naturally occurring amino acid, or a variant thereof. The superscript to the right of each Xaa represents the position of the amino acid within the primary sequence of the polypeptide chain. $Xaa^1$ represents the first, or N-terminal, amino acid in the polypeptide chain, and $Xaa^q$ represents the last, or C-terminal, amino acid in the polypeptide chain. The variable q is an integer that is equal to the total number of amino acids in the polypeptide chain. Each Naa represents a non-natural amino acid within the polypeptide chain. Useful non-natural amino acids are described in the sections below. The integer n represents the number of non-natural amino acids in the polypeptide chain. In typical embodiments, n is an integer greater than 1. Each integer p(i) is greater than 1 and less than q, and the variable i is an integer that varies from 1 to n. Each integer p(i) represents a site-specific location in the amino acid sequence for the corresponding Naa. Each site specific location p(i) is optimal for substitution of a naturally occurring amino acid with a non-natural amino acid, such as $Naa^{p(i)}$, according to the techniques described herein.

Analysis of the data from TAG screening as presented in the Examples allowed selection of sites which are ideal candidates for making ADCs on the basis of cell killing, expression levels, drug-to-antibody ratio, solvent accessibility and (where available) thermal stability. The most preferred sites have lower solvent accessibility, and higher thermostability than the other tested variants. The preferred sites for nnAA incorporation are listed in Table I, below.

TABLE I

Preferred Sites for nnAA Incorporation

| Site of nnAA | Preference |
| --- | --- |
| HC-F404 | Most Preferred |
| HC-K121 | Most Preferred |
| HC-S136 | Most Preferred |
| HC-Y180 | Most Preferred |
| HC-F241 | Most Preferred |
| LC-T22 | Most Preferred |
| LC-S7 | Most Preferred |
| LC-N152 | Most Preferred |
| HC-S25 | More Preferred |
| HC-A40 | More Preferred |
| HC-S119 | More Preferred |
| HC-S190 | More Preferred |
| HC-K222 | More Preferred |
| HC-R19 | Preferred |
| HC-Y52 | Preferred |
| HC-S70 | Preferred |

Accordingly, in certain embodiments, provided herein are antibodies comprising one or more non-natural amino acids at one or more positions selected from the group consisting of heavy chain or light chain residues EU HC-F404, EU HC-K121, EU HC-F241, EU HC-Y180, Kabat or Chothia LC-T22, Kabat or Chothia LC-S7, EU LC-N152, EU HC-S136, Kabat or Chothia HC-S25, Kabat or Chothia HC-A40, EU HC-S119, EU HC-S190, EU HC-K222, Kabat or Chothia HC-R19, Kabat or Chothia HC-Y52, or Kabat or Chothia HC-S70, or a post-translationally modified variant thereof.

In certain embodiments, provided herein are antibodies comprising one or more non-natural amino acids at one or more positions selected from the group consisting of heavy chain or light chain residues EU HC-F404, EU HC-K121, EU HC-Y180, EU HC-F241, Kabat or Chothia LC-T22, Kabat or Chothia LC-S7, EU LC-N152, EU HC-S136, Kabat or Chothia HC-S25, Kabat or Chothia HC-A40, EU HC-S119, EU HC-S190, and EU HC-K222, or a post-translationally modified variant thereof.

In certain embodiments, provided herein are antibodies comprising one or more non-natural amino acids at one or more positions selected from the group consisting of heavy chain or light chain residues EU HC-F404, EU HC-K121, EU HC-Y180, EU HC-F241, Kabat or Chothia LC-T22, Kabat or Chothia LC-S7, EU LC-N152, and EU HC-S136, or a post-translationally modified variant thereof.

In certain embodiments, further provided herein are conservatively modified variants of the above antibodies. Conservatively modified variants of an antibody include one or more insertions, deletions or substitutions that do not disrupt the structure and/or function of the antibody when evaluated by one of skill in the art. In certain embodiments, conservatively modified variants include 20 or fewer amino acid insertions, deletions or substitutions. In certain embodiments, conservatively modified variants include 15 or fewer amino acid insertions, deletions or substitutions. In certain embodiments, conservatively modified variants include 10 or fewer amino acid insertions, deletions or substitutions. In certain embodiments, conservatively modified variants include 9 or fewer amino acid insertions, deletions or substitutions. In certain embodiments, conservatively modified variants include 8 or fewer amino acid insertions, deletions or substitutions. In certain embodiments, conservatively modified variants include 7 or fewer amino acid insertions, deletions or substitutions. In certain embodiments, conservatively modified variants include 6 or fewer amino acid insertions, deletions or substitutions. In certain embodiments, conservatively modified variants include 5 or fewer amino acid insertions, deletions or substitutions. In certain embodiments, conservatively modified variants include 4 or fewer amino acid insertions, deletions or substitutions. In certain embodiments, conservatively modified variants include 3 or fewer amino acid insertions, deletions or substitutions. In certain embodiments, conservatively modified variants include 2 or fewer amino acid insertions, deletions or substitutions. In certain embodiments, conservatively modified variants include 1 amino acid insertion, deletion or substitution. In particular embodiments the substitutions are conservative, substituting an amino acid within the same class, as described above.

In certain embodiments, the antibodies can be modified to modulate structure, stability and/or activity. In such embodiments, the modifications can be conservative or other than conservative. The modifications need only be suitable to the practitioner carrying out the methods and using the compositions described herein. In certain embodiments, the modifications decrease but do not eliminate antigen binding affinity. In certain embodiments, the modifications increase antigen binding affinity. In certain embodiments, the modifications enhance structure or stability of the antibody. In certain embodiments, the modifications reduce but do not eliminate structure or stability of the antibody. In certain embodiments, modified variants include 20 or fewer amino acid insertions, deletions or substitutions. In certain embodiments, modified variants include 15 or fewer amino acid insertions, deletions or substitutions. In certain embodiments, modified variants include 10 or fewer amino acid insertions, deletions or substitutions. In certain embodiments, modified variants include 9 or fewer amino acid insertions, deletions or substitutions. In certain embodiments, modified variants include 8 or fewer amino acid insertions, deletions or substitutions. In certain embodiments, modified variants include 7 or fewer amino acid insertions, deletions or substitutions. In certain embodiments, modified variants include 6 or fewer amino acid insertions, deletions or substitutions. In certain embodiments, modified variants include 5 or fewer amino acid insertions, deletions or substitutions. In certain embodiments, modified variants include 4 or fewer amino acid insertions, deletions or substitutions. In certain embodiments, modified variants include 3 or fewer amino acid insertions, deletions or substitutions. In certain embodiments, modified variants include 2 or fewer amino acid insertions, deletions or substitutions. In certain embodiments, modified variants include 1 amino acid insertion, deletion or substitution.

Also within the scope are post-translationally modified variants. Any of the antibodies provided herein can be post-translationally modified in any manner recognized by those of skill in the art. Typical post-translational modifications for antibodies include interchain disulfide bonding, intrachain disulfide bonding, N-linked glycosylation and proteolysis. Also provided herein are other post-translationally modified antibodies having modifications such as phosphorylation, O-linked glycosylation, methylation, acetylation, lipidation, GPI anchoring, myristoylation and prenylation. The post-translational modification can occur during production, in vivo, in vitro or otherwise. In certain embodiments, the post-translational modification can be an intentional modification by a practitioner, for instance, using the methods provided herein.

Further included within the scope are antibodies fused to further peptides or polypeptides. Exemplary fusions include, but are not limited to, e.g., a methionyl antibody in which a methionine is linked to the N-terminus of the antibody resulting from the recombinant expression, fusions for the purpose of purification (including but not limited to, to poly-histidine or affinity epitopes), fusions for the purpose of linking to other biologically active molecules, fusions with serum albumin binding peptides, and fusions with serum proteins such as serum albumin. The antibodies may comprise protease cleavage sequences, reactive groups, antibody-binding domains (including but not limited to, FLAG or poly-His) or other affinity based sequences (including but not limited to, FLAG, poly-His, GST, etc.). The antibodies may also comprise linked molecules (including but not limited to, biotin) that improve detection (including but not limited to, GFP), purification or other features of the antibody. In certain embodiments, the antibodies comprise a C-terminal affinity sequence that facilitates purification of full length antibodies. In certain embodiments, such C-terminal affinity sequence is a poly-His sequence, e.g., a 6-His sequence.

The antibody can have any antibody form recognized by those of skill in the art. The antibody can comprise a single polypeptide chain a single heavy chain or a single light chain. The antibody can also form multimers that will be recognized by those of skill in the art including homodimers, heterodimers, homomultimers, and heteromultimers. These multimers can be linked or unlinked. Useful linkages include interchain disulfide bonds typical for antibody molecules. The multimers can also be linked by other amino acids, including the non-natural amino acids introduced according to the present description. The antibody can be an immunoglobulin such as of any class or subclass including IgA, IgA1, IgA2, IgD, IgE, IgG, IgG1, IgG2, IgG3, IgG4 and IgM. The antibody can be of the form of any antibody fragment including Fv, Fc, Fab, and (Fab')$_2$ and scFv.

The antibody may further be glycosylated or aglycosyated. Accordingly, in certain embodiments, the antibody is glycosylated. In certain embodiments, the antibody is aglycosylated. Agylcosylated antibodies comprising a non-natural amino acid may be made, for example, as described in the Examples provided herein or through bacterial expression systems known to those skilled in the art. Glycosylated antibodies comprising a non-natural amino acid may be made, for example, as described by Axup et al., 2012, *Proc. Nat. Acad. Sci.* USA 109(40):16101-16106.

Also provided herein are antibodies that are conjugated to one or more conjugation moieties. The conjugation moiety can be any conjugation moiety deemed useful to one of skill in the art. For instance, the conjugation moiety can be a polymer, such as polyethylene glycol, that can improve the stability of the antibody in vitro et in vivo. The conjugation moiety can have therapeutic activity, thereby yielding an antibody-drug conjugate. The conjugation moiety can be a molecular payload that is harmful to target cells. The conjugation moiety can be a label useful for detection or diagnosis. In certain embodiments, the conjugation moiety is linked to the antibody via a direct covalent bond. In certain embodiments, the conjugation moiety is linked to the antibody via a linker. In advantageous embodiments, the conjugation moiety or the linker is attached via one of the non-natural amino acids of the antibody. Exemplary conjugation moieties and linkers are discussed in the sections below.

Non-natural Amino Acids

The non-natural amino acid can be any non-natural amino acid known to those of skill in the art. In some embodiments, the non-naturally encoded amino acid comprises a functional group. The functional group can be any functional group known to those of skill in the art. In certain embodiments the functional group is a label, a polar group, a non-polar group or a reactive group.

Reactive groups are particularly advantageous for linking further functional groups to the antibody at the site-specific position of the antibody chain. In certain embodiments, the reactive group is selected from the group consisting of amino, carboxy, acetyl, hydrazino, hydrazido, semicarbazido, sulfanyl, azido and alkynyl.

In certain embodiments, the amino acid residue is according to any of the following formulas:

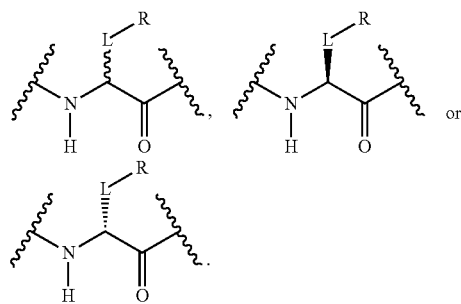

Those of skill in the art will recognize that antibodies are generally comprised of L-amino acids. However, with non-natural amino acids, the present methods and compositions provide the practitioner with the ability to use L-, D- or racemic non-natural amino acids at the site-specific positions. In certain embodiments, the non-natural amino acids described herein include D-versions of the natural amino acids and racemic versions of the natural amino acids.

In the above formulas, the wavy lines indicate bonds that connect to the remainder of the polypeptide chains of the antibodies. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas.

In the above formulas R designates any functional group without limitation, so long as the amino acid residue is not identical to a natural amino acid residue. In certain embodiments, R can be a hydrophobic group, a hydrophilic group, a polar group, an acidic group, a basic group, a chelating group, a reactive group, a therapeutic moiety or a labeling moiety. In certain embodiments, R is selected from the group consisting of $R^1NR^2R^3$, $R^1C(=O)R^2$, $R^1C(=O)OR^2$, $R^1N_3$, $R^1C(\equiv CH)$. In these embodiments, $R^1$ is selected from the group consisting of a bond, alkylene, heteroalkylene, arylene, heteroarylene. $R^2$ and $R^3$ are each independently selected from the group consisting of hydrogen, alkyl and heteroalkyl.

In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

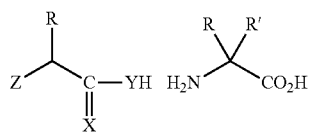

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, P and y amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, for additional methionine analogs.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 1989:1859-1866; Barton et al., (1987) Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

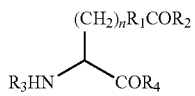

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Cornish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

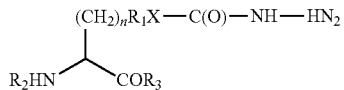

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the aliphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J. Am. Chem. Soc. 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

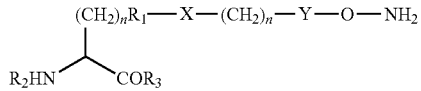

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, J. Org. Chem. 68: 8853-8858 (2003). Certain aminooxy-containing amino acids, such as L-2-amino-4-(aminooxy)butyric acid, have been isolated from natural sources (Rosenthal, G. et al., Life Sci. 60: 1635-1641 (1997). Other aminooxy-containing amino acids can be prepared by one skilled in the art.

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing antibody can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tornoe, C. W., et al., J. Org. Chem. 67:3057-3064 (2002); Rostovtsev, et al., Angew. Chem. Int. Ed. 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the antigen-binding polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

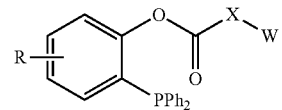

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2R'$, —$S(O)_2NR'R"$, —CN and —$NO_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

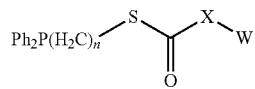

wherein n is 1-10; X can be O, N, S or not present, Ph is phenyl, and W is a water soluble polymer.

Exemplary alkyne-containing amino acids can be represented as follows:

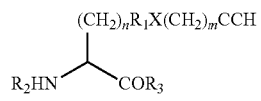

wherein n is 0-10; $R_1$ is an alkyl, aryl, substituted alkyl, or substituted aryl or not present; X is O, N, S or not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., J. Am. Chem. Soc. 125: 11782-11783 (2003), and 4-alkynyl-L-phenylalanine can be synthesized as described in Kayser, B., et al., Tetrahedron 53(7): 2475-2484 (1997). Other alkyne-containing amino acids can be prepared by one skilled in the art.

Exemplary azide-containing amino acids can be represented as follows:

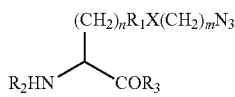

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the azide moiety is positioned para to the alkyl side chain. In some embodiments, n is 0-4 and $R_1$ and X are not present, and m=0. In some embodiments, n is 1, $R_1$ is phenyl, X is O, m is 2 and the P-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, J. Am. Chem. Soc. 1995, 117 (14) 3893-3899. In some embodiments, beta-substituted aminothiol amino acids can be incorporated into antibodies and then reacted with water soluble polymers comprising an aldehyde functionality. In some embodiments, a water soluble polymer, drug conjugate or other payload can be coupled to an antibody polypeptide comprising a beta-substituted aminothiol amino acid via formation of the thiazolidine.

Particular examples of useful non-natural amino acids include, but are not limited to, p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc b-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine. Further useful examples include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine.

In particular embodiments, the non-natural amino acids are selected from p-acetyl-phenylalanine, p-ethynyl-phenylalanine, p-propargyloxyphenylalanine, and p-azido-phenylalanine. One particularly useful non-natural amino acid is p-azido phenylalanine. This amino acid residue is known to those of skill in the art to facilitate Huisgen [3+2] cyloaddition reactions (so-called "click" chemistry reactions) with, for example, compounds bearing alkynyl groups. This reaction enables one of skill in the art to readily and rapidly conjugate to the antibody at the site-specific location of the non-natural amino acid.

In certain embodiments, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry can be used. In certain embodiments, the first reactive group is the azido moiety (including but not limited to, in the unnatural amino acid p-azido-L-phenylalanine) and the second reactive group is the alkynyl moiety.

In the above formulas, each L represents a divalent linker. The divalent linker can be any divalent linker known to those of skill in the art. Generally, the divalent linker is capable of forming covalent bonds to the functional moiety R and the alpha carbon of the non-natural amino acid. Useful divalent linkers include a bond, alkylene, substituted alkylene, heteroalkylene, substituted heteroalkylene, arylene, substituted arylene, heteroarlyene and substituted heteroarylene. In certain embodiments, L is $C_{1-10}$ alkylene or $C_{1-10}$ heteroalkylene.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Illustrative, non-limiting examples of amino acids that satisfy these four properties for non-natural amino acids that can be used with the compositions and methods described herein are presented in FIGS. 1-13. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

In further embodiments, non-natural amino acids that may be used in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or non-covalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

The chemical moieties incorporated into antibodies via incorporation of non-natural amino acids offer a variety of advantages and manipulations of polypeptides. For example, the unique reactivity of a carbonyl or dicarbonyl functional group (including a keto- or aldehyde-functional group) allows selective modification of antibodies with any of a number of hydrazine- or hydroxylamine-containing reagents in vivo and in vitro. A heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photocrosslinking of polypeptides. Examples of photoreactive non-natural amino acids include, but are not limited to, p-azido-phenylalanine and p-benzoyl-phenylalanine. The antibodies with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

Amino acids with an electrophilic reactive group allow for a variety of reactions to link molecules via various chemical reactions, including, but not limited to, nucleophilic addition reactions. Such electrophilic reactive groups include a carbonyl- or dicarbonyl-group (including a keto- or aldehyde group), a carbonyl-like- or dicarbonyl-like-group (which has reactivity similar to a carbonyl- or dicarbonyl-group and is structurally similar to a carbonyl- or dicarbonyl-group), a masked carbonyl- or masked dicarbonyl-group (which can be readily converted into a carbonyl- or dicarbonyl-group), or a protected carbonyl- or protected dicarbonyl-group (which has reactivity similar to a carbonyl- or dicarbonyl-group upon deprotection). Such amino acids include amino acids having the structure of Formula (I):

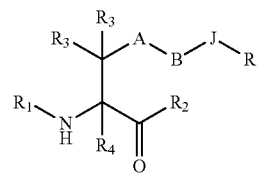

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; J is

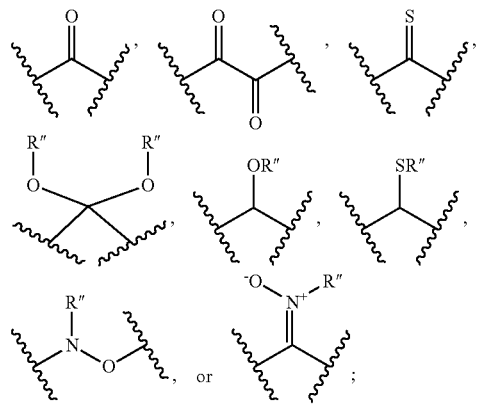

R is H, alkyl, substituted alkyl, cycloalkyl, or substituted cycloalkyl; each R" is independently H, alkyl, substituted alkyl, or a protecting group, or when more than one R" group is present, two R" optionally form a heterocycloalkyl; $R_1$ is H, an amino protecting group, resin, amino acid, polypeptide, or polynucleotide; and $R_2$ is OH, an ester protecting group, resin, amino acid, polypeptide, or polynucleotide; each of $R_3$ and $R_4$ is independently H, halogen, lower alkyl, or substituted lower alkyl, or $R_3$ and $R_4$ or two $R_3$ groups optionally form a cycloalkyl or a heterocycloalkyl; or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group; or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group; with a proviso that when A is phenylene and each $R_3$ is H, B is present; and that when A is —(CH$_2$)$_4$— and each $R_3$ is H, B is not —NHC(O)(CH$_2$CH$_2$)—; and that when A and B are absent and each $R_3$ is H, R is not methyl. Such non-natural amino acids may be in the form of a salt, or may be incorporated into a non-natural amino acid polypeptide, polymer, polysaccharide, or a polynucleotide and optionally post translationally modified.

In certain embodiments, compounds of Formula (I) are stable in aqueous solution for at least 1 month under mildly acidic conditions. In certain embodiments, compounds of Formula (I) are stable for at least 2 weeks under mildly acidic conditions. In certain embodiments, compound of Formula (I) are stable for at least 5 days under mildly acidic conditions. In certain embodiments, such acidic conditions are pH 2 to 8.

In certain embodiments of compounds of Formula (I), B is lower alkylene, substituted lower alkylene, —O-(alkylene or substituted alkylene)-, —C(R')=N—N(R')—, —N(R')CO—, —C(O)—, —C(R')=N—, —C(O)-(alkylene or substituted alkylene)-, —CON(R')-(alkylene or substituted alkylene)-, —S(alkylene or substituted alkylene)-, —S(O)(alkylene or substituted alkylene)-, or —S(O)$_2$(alkylene or substituted alkylene)-. In certain embodiments of compounds of Formula (I), B is —O(CH$_2$)—, —CH=N—, —CH=N—NH—, —NHCH$_2$—, —NHCO—, —C(O)—, —C(O)—(CH$_2$)—, —CONH—(CH$_2$)—, —SCH$_2$—, —S(=O)CH$_2$—, or —S(O)$_2$CH$_2$—. In certain embodiments of compounds of Formula (I), R is C$_1$-6 alkyl or cycloalkyl. In certain embodiments of compounds of Formula (I) R is —CH$_3$, —CH(CH$_3$)$_2$, or cyclopropyl. In certain embodiments of compounds of Formula (I), $R_1$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (I), $R_1$ is a resin, amino acid, polypeptide, or polynucleotide. In certain embodiments of compounds of Formula (I), $R_2$ is OH, O-methyl, O-ethyl, or O-t-butyl. In certain embodiments of compounds of Formula (I), $R_2$ is a resin, amino acid, polypeptide, or polynucleotide. In certain embodiments of compounds of Formula (I), $R_2$ is a polynucleotide. In certain embodiments of compounds of Formula (I), $R_2$ is ribonucleic acid (RNA). In certain embodiments of compounds of Formula (I), $R_2$ is tRNA. In certain embodiments of compounds of Formula (I), the tRNA specifically recognizes a selector codon. In certain embodiments of compounds of Formula (I) the selector codon is selected from the group consisting of an amber codon, ochre codon, opal codon, a unique codon, a rare codon, an unnatural codon, a five-base codon, and a four-base codon. In certain embodiments of compounds of Formula (I), $R_2$ is a suppressor tRNA.

In certain embodiments of compounds of Formula (I),

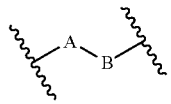

is selected from the group consisting of: (i) A is substituted lower alkylene, C$_4$-arylene, substituted arylene, heteroarylene, substituted heteroarylene, alkarylene, substituted alkarylene, aralkylene, or substituted aralkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)$_2$—, —NS(O)$_2$—, —OS(O)$_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)$_2$N(R'), —N(R')C(O)N(R')—, —N(R')C(S)N(R')—, —N(R')S(O)N(R')—, —N(R')S(O)$_2$N(R')—, —N(R')—N=, —C(R')=N—N(R')—, —C(R')=N—N=, —C(R')$_2$—N=N—, and —C(R')$_2$—N(R')—N(R')—; (ii) A is optional, and when present is substituted lower alkylene, C$_4$-arylene, substituted arylene, heteroarylene, substituted heteroarylene, alkarylene, substituted alkarylene, aralkylene, or substituted aralkylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)$_2$—, —NS(O)$_2$—, —OS(O)$_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)$_2$N(R'), —N(R')C(O)N(R')—, —N(R')C(S)N(R')—, —N(R')S(O)N(R')—, —N(R')S(O)$_2$N(R')—, —N(R')—N═, —C(R')═N—N(R')—, —C(R')═N—N═, —C(R')$_2$—N═N—, and —C(R')$_2$—N(R')—N(R')—; (iii) A is lower alkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)$_2$—, —NS(O)$_2$—, —OS(O)$_2$—, —C(O)—, —C(O)-(alkylene or substituted alkylene)-, —C(S)—, —N(R')—, —C(O)N(R')—, —CSN(R')—, —CON(R')-(alkylene or substituted alkylene)-, —N(R')C(O)O—, —N(R')C(S)—, —S(O)N(R'), —S(O)$_2$N(R'), —N(R')C(O)N(R')—, —N(R')C(S)N(R')—, —N(R')S(O)N(R')—, —N(R')S(O)$_2$N(R')—, —N(R')—N═, —C(R')═N—N(R')—, —C(R')═N—N═, —C(R')$_2$—N═N—, and —C(R')$_2$—N(R')—N(R')—; and (iv) A is phenylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)$_2$—, —NS(O)$_2$—, —OS(O)$_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)$_2$N(R'), —N(R')C(O)N(R')—, —N(R')C(S)N(R')—, —N(R')S(O)N(R')—, —N(R')S(O)$_2$N(R')—, —N(R')—N═, —C(R')'N═N(R')—, —C(R')═N—N═, —C(R')$_2$—N═N—, and —C(R')$_2$—N(R')—N(R')—; J is

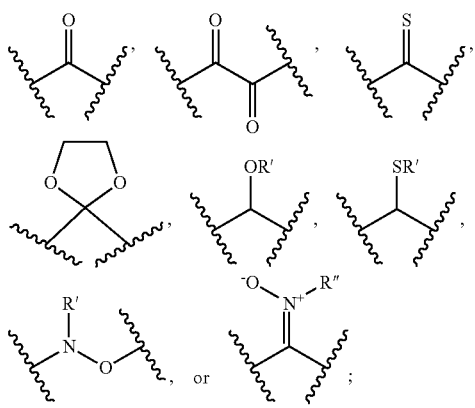

each R' is independently H, alkyl, or substituted alkyl; R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide; and each R$_3$ and R$_4$ is independently H, halogen, lower alkyl, or substituted lower alkyl; and R is H, alkyl, substituted alkyl, cycloalkyl, or substituted cycloalkyl.

In addition, amino acids having the structure of Formula (II) are included:

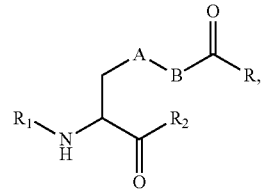

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; R is H, alkyl, substituted alkyl, cycloalkyl, or substituted cycloalkyl; R$_1$ is H, an amino protecting group, resin, amino acid, polypeptide, or polynucleotide; and R$_2$ is OH, an ester protecting group, resin, amino acid, polypeptide, or polynucleotide. In certain embodiments, when A is phenylene, B is present; and that when A is —(CH$_2$)$_4$—, B is not —NHC(O)(CH$_2$CH$_2$)—; and that when A and B are absent, R is not methyl. Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (III) are included:

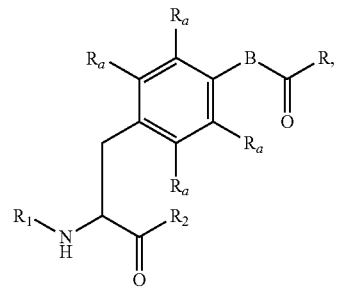

wherein: B is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; R is H, alkyl, substituted alkyl, cycloalkyl, or substituted cycloalkyl; R$_1$ is H, an amino protecting group, resin, amino acid, polypeptide, or polynucleotide; and R$_2$ is OH, an ester protecting group, resin, amino acid, polypeptide, or polynucleotide; each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

In addition, the following amino acids are included:

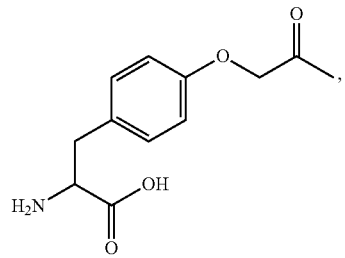 [SMILES: CC(=O)CCc1ccc(CC(N)C(=O)O)cc1]

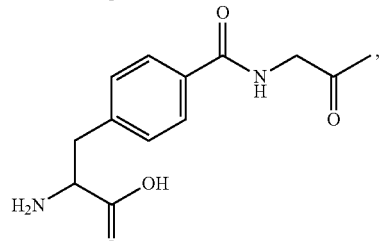

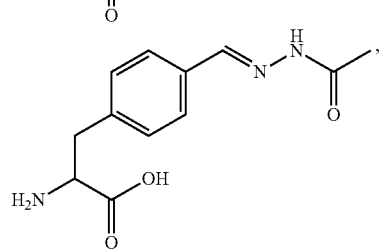

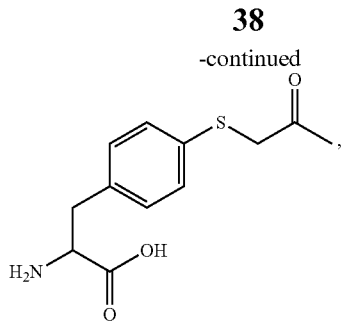

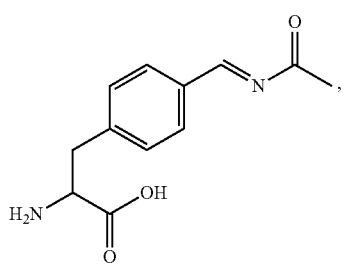

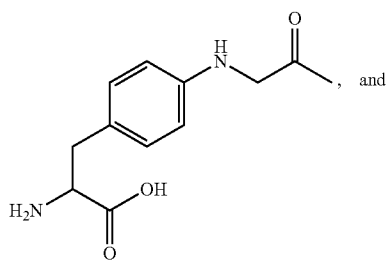

Such non-natural amino acids may be are optionally amino protected group, carboxyl protected and/or in the form of a salt, or may be incorporated into a non-natural amino acid polypeptide, polymer, polysaccharide, or a polynucleotide and optionally post translationally modified.

In addition, the following amino acids having the structure of Formula (IV) are included:

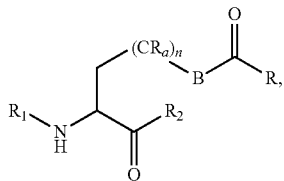

wherein —NS(O)₂—, —OS(O)₂—, optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')₂—N=N—, and —C(R')₂—N(R')—N(R')—, where each R' is independently H, alkyl, or substituted alkyl; R is H, alkyl, substituted alkyl, cycloalkyl, or substituted cycloalkyl; R₁ is H, an amino protecting group, resin, amino acid, polypeptide, or polynucleotide; and R₂ is OH, an ester protecting group, resin, amino acid, polypeptide, or polynucleotide; each R$_a$ is independently selected from the group consisting of H, halogen, alkyl, substituted alkyl, —N(R')₂, —C(O)$_k$R' where k is 1, 2, or 3, —C(O)N(R')₂, —OR', and —S(O)$_k$R', where each R' is independently H, alkyl, or substituted alkyl; and n is 0 to 8. In certain embodiments, when A is —(CH₂)₄—, B is not —NHC(O)(CH₂CH₂)—. Such non-natural amino acids may be in the form of a salt, or may be incorporated into a non-natural amino acid polypeptide, polymer, polysaccharide, or a polynucleotide and optionally post translationally modified.

In addition, the following amino acids are included:

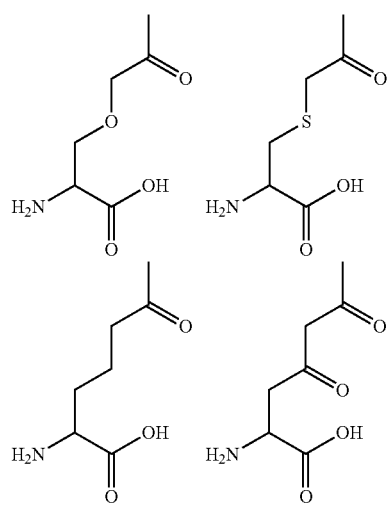

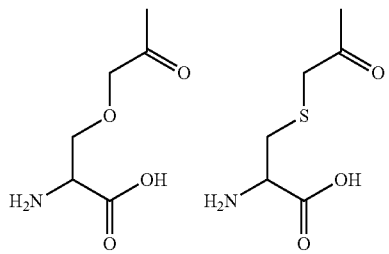

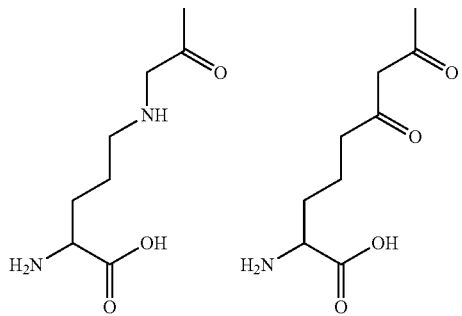

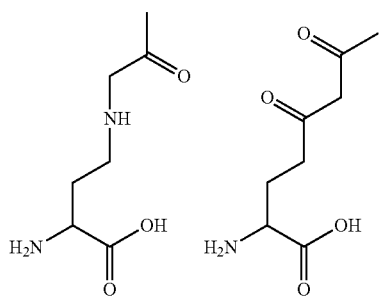

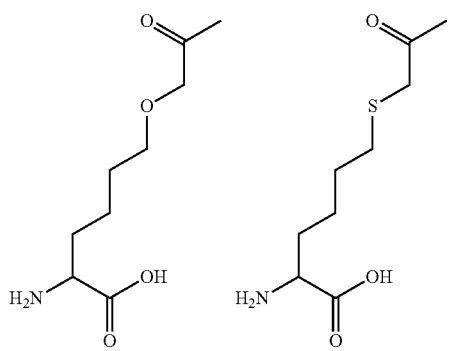

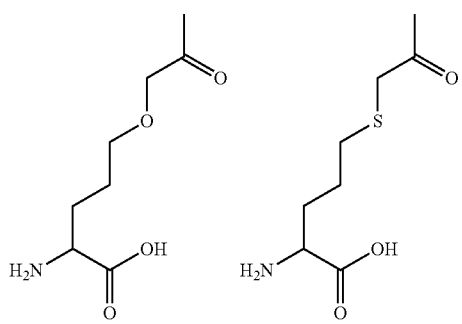

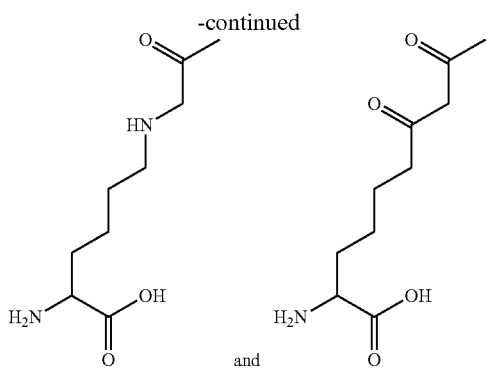 and wherein such compounds are optionally amino protected, optionally carboxyl protected, optionally amino protected and carboxyl protected, or a salt thereof, or may be incorporated into a non-natural amino acid polypeptide, polymer, polysaccharide, or a polynucleotide and optionally post translationally modified.

In addition, the following amino acids having the structure of Formula (VIII) are included:

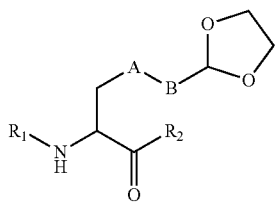

wherein, A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; R$_1$ is H, an amino protecting group, resin, amino acid, polypeptide, or polynucleotide; and R$_2$ is OH, an ester protecting group, resin, amino acid, polypeptide, or polynucleotide. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (IX) are included:

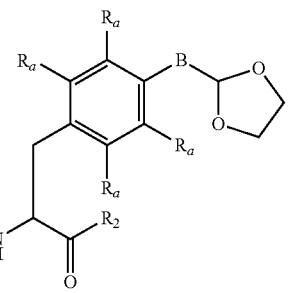

wherein, B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; R is H, alkyl, substituted alkyl, cycloalkyl, or substituted cycloalkyl; R$_1$ is H, an amino protecting group, resin, amino acid, polypeptide, or polynucleotide; and R$_2$ is OH, an ester protecting group, resin, amino acid, polypeptide, or polynucleotide; wherein each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

In addition, the following amino acids are included:

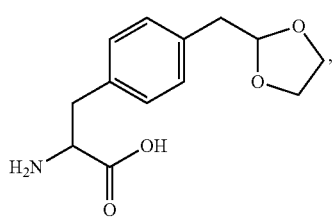

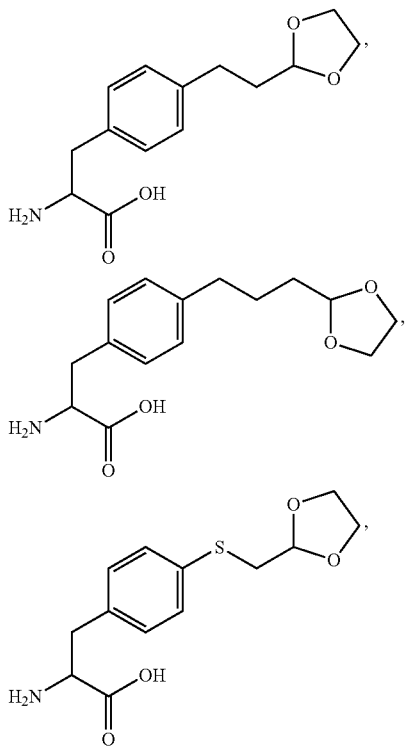

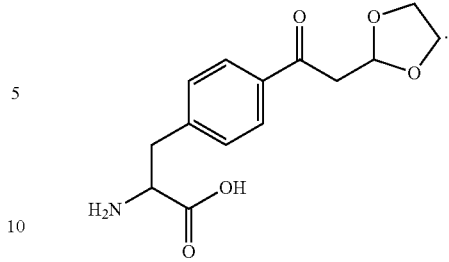

wherein such compounds are optionally amino protected, optionally carboxyl protected, optionally amino protected and carboxyl protected, or a salt thereof, or may be incorporated into a non-natural amino acid polypeptide, polymer, polysaccharide, or a polynucleotide and optionally post translationally modified.

In addition, the following amino acids having the structure of Formula (X) are included:

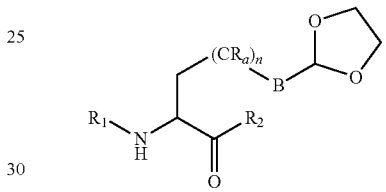

wherein, B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; R is H, alkyl, substituted alkyl, cycloalkyl, or substituted cycloalkyl; R$_1$ is H, an amino protecting group, resin, amino acid, polypeptide, or polynucleotide; and R$_2$ is OH, an ester protecting group, resin, amino acid, polypeptide, or polynucleotide; each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8. Such non-natural amino acids may be in the form of a salt, or may be incorporated into a non-natural amino acid polypeptide, polymer, polysaccharide, or a polynucleotide and optionally post translationally modified.

In addition, the following amino acids are included:

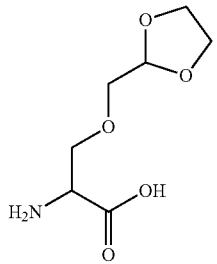
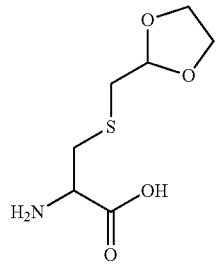
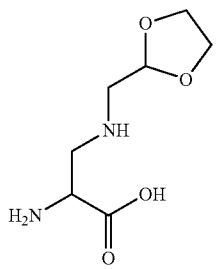
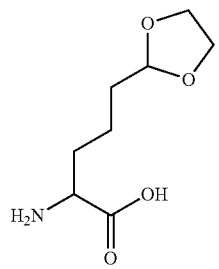
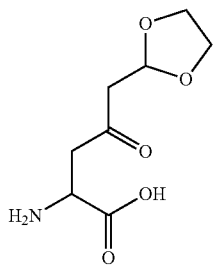
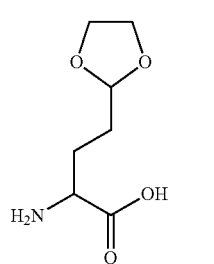
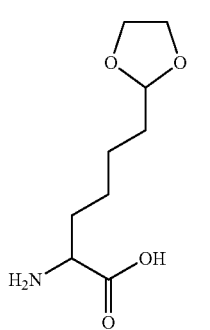 and 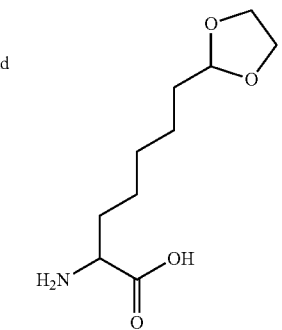

wherein such compounds are optionally amino protected, optionally carboxyl protected, optionally amino protected and carboxyl protected, or a salt thereof, or may be incorporated into a non-natural amino acid polypeptide, polymer, polysaccharide, or a polynucleotide and optionally post translationally modified.

In addition to monocarbonyl structures, the non-natural amino acids described herein may include groups such as dicarbonyl, dicarbonyl like, masked dicarbonyl and protected dicarbonyl groups. For example, the following amino acids having the structure of Formula (V) are included:

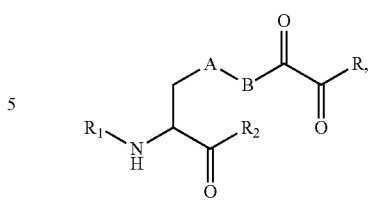

wherein, A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (VI) are included:

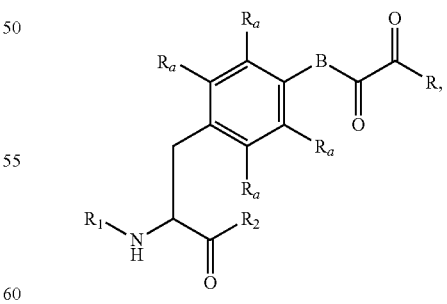

wherein, B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; R is H, alkyl, substituted alkyl, cycloalkyl, or substituted cycloalkyl; R$_1$ is H, an amino protecting group, resin, amino acid, polypeptide, or polynucleotide; and R$_2$ is OH, an ester protecting group, resin, amino acid, polypeptide, or polynucleotide; wherein each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

In addition, the following amino acids are included:

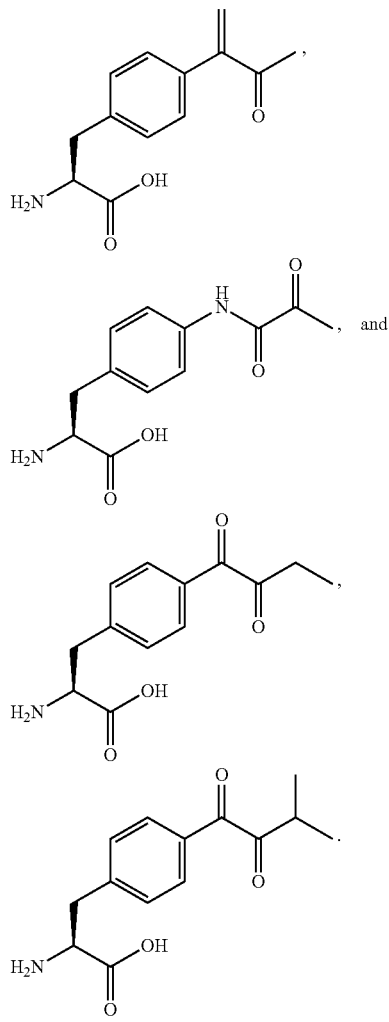

wherein such compounds are optionally amino protected and carboxyl protected, or a salt thereof. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (VII) are included:

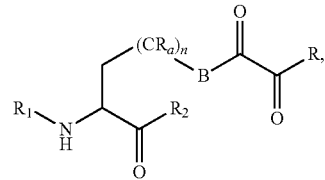

wherein, B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; R is H, alkyl, substituted alkyl, cycloalkyl, or substituted cycloalkyl; R$_1$ is H, an amino protecting group, resin, amino acid, polypeptide, or polynucleotide; and R$_2$ is OH, an ester protecting group, resin, amino acid, polypeptide, or polynucleotide; each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8. Such non-natural amino acids may be in the form of a salt, or may be incorporated into a non-natural amino acid polypeptide, polymer, polysaccharide, or a polynucleotide and optionally post translationally modified.

In addition, the following amino acids are included:

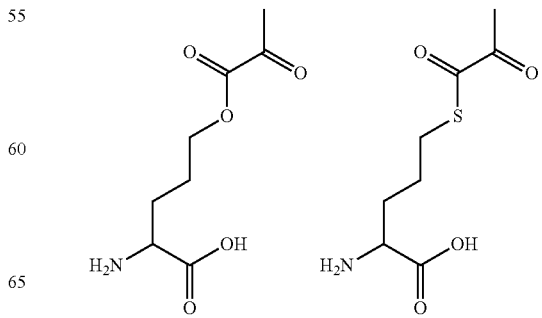

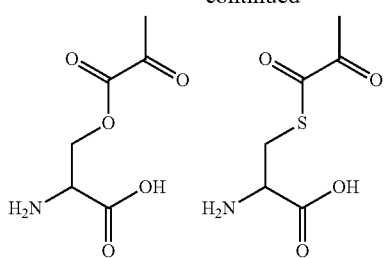
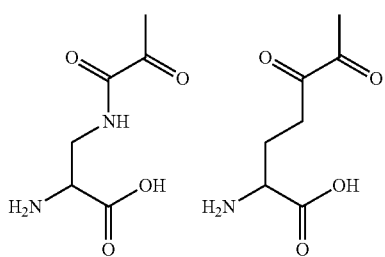
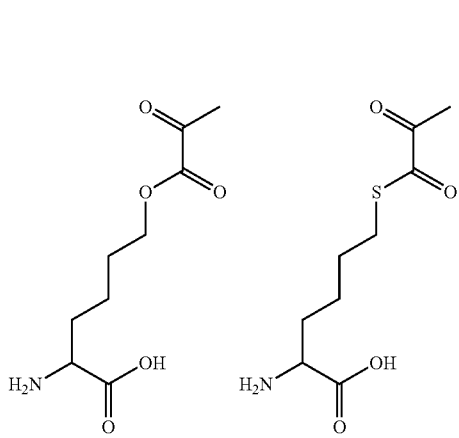
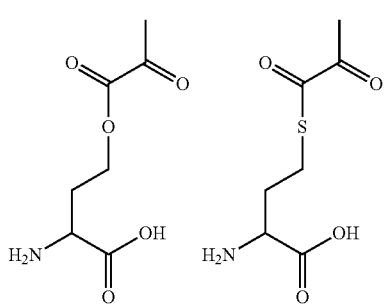
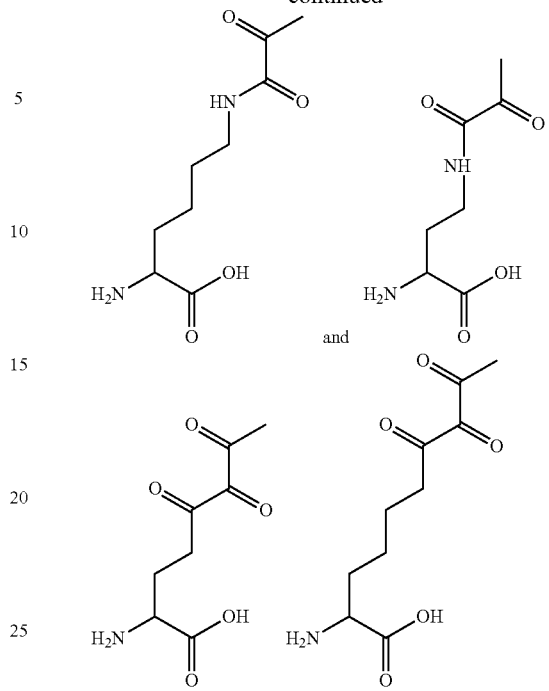

wherein such compounds are optionally amino protected and carboxyl protected, or a salt thereof, or may be incorporated into a non-natural amino acid polypeptide, polymer, polysaccharide, or a polynucleotide and optionally post translationally modified.

In addition, the following amino acids having the structure of Formula (XXX) are included:

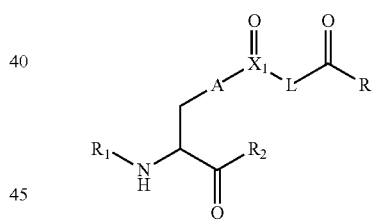

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; $X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXX-A) are included:

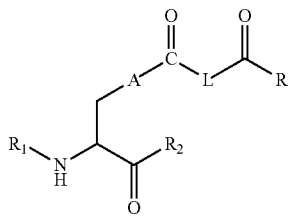

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; L is alkylene, substituted alkylene, N(R')(alkylene) or N(R')(substituted alkylene), where R' is H, alkyl, substituted alkyl, cycloalkyl, or substituted cycloalkyl. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXX-B) are included:

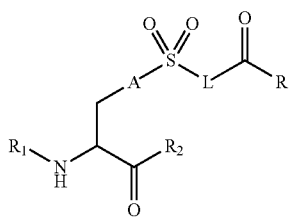

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; L is alkylene, substituted alkylene, N(R')(alkylene) or N(R')(substituted alkylene), where R' is H, alkyl, substituted alkyl, cycloalkyl, or substituted cycloalkyl. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXI) are included:

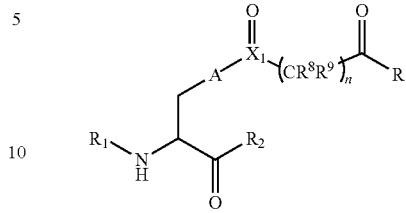

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; $X_1$ is C, S, or S(O); and n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXI-A) are included:

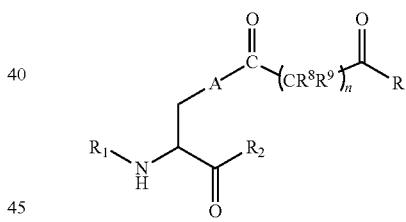

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXI-B) are included:

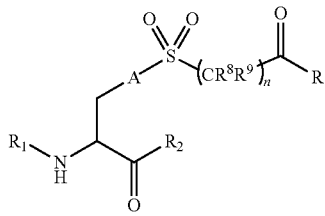

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXII) are included:

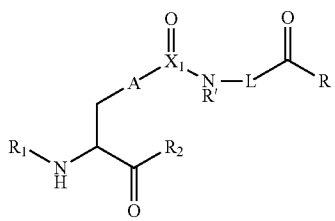

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; $X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl. Such non-natural amino acids may be in the form of a salt, or may be incorporated into a non-natural amino acid polypeptide, polymer, polysaccharide, or a polynucleotide and optionally post translationally modified.

The In addition, the following amino acids having the structure of Formula (XXXII-A) are included:

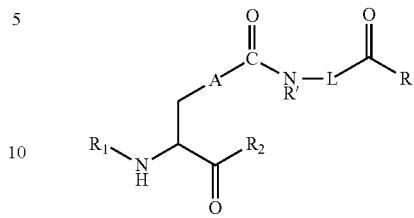

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; L is alkylene, substituted alkylene, N(R')(alkylene) or N(R')(substituted alkylene), where R' is H, alkyl, substituted alkyl, cycloalkyl, or substituted cycloalkyl. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXII-B) are included:

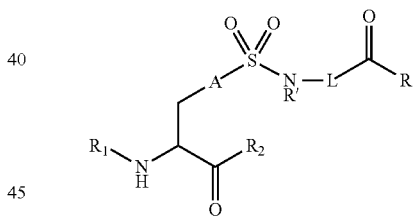

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; L is alkylene, substituted alkylene, N(R')(alkylene) or N(R')(substituted alkylene), where R' is H, alkyl, substituted alkyl, cycloalkyl, or substituted cycloalkyl. Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXX) are included:

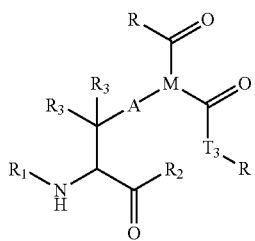

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

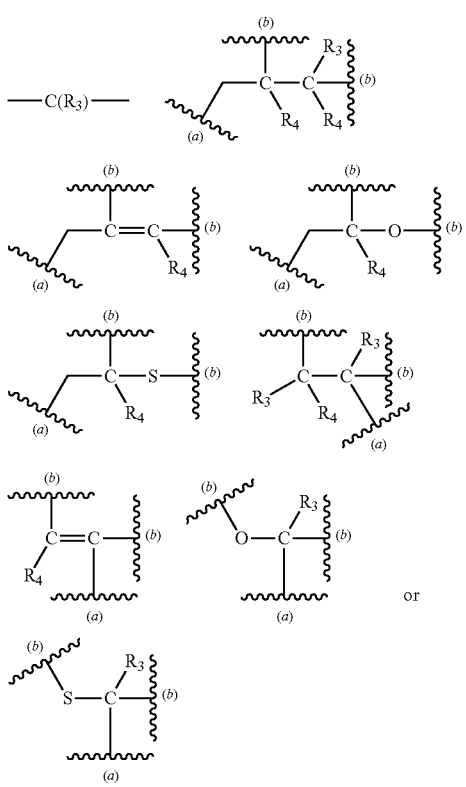

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl; R is H, halogen, alkyl, substituted alkyl, cycloalkyl, or substituted cycloalkyl; $T_3$ is a bond, C(R)(R), O, or S, and R is H, halogen, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide. Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXXI) are included:

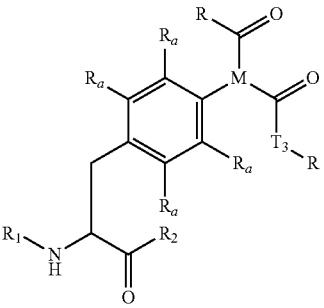

wherein:

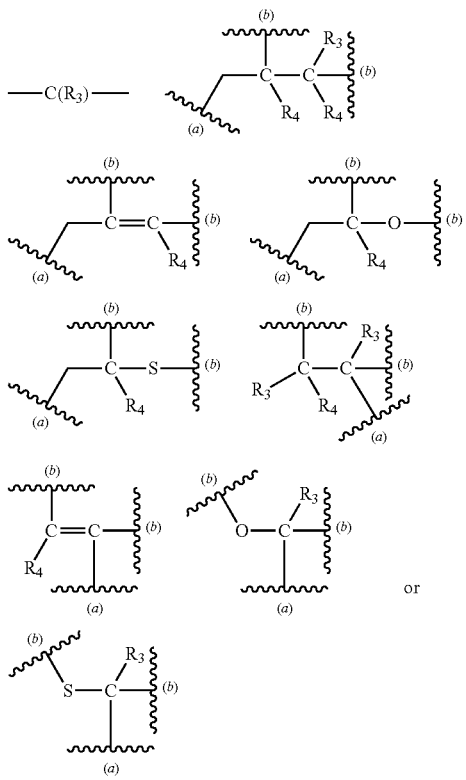

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl; R is H, halogen, alkyl, substituted alkyl, cycloalkyl, or substituted cycloalkyl; $T_3$ is a bond, C(R)(R), O, or S, and R is H, halogen, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXXII) are included:

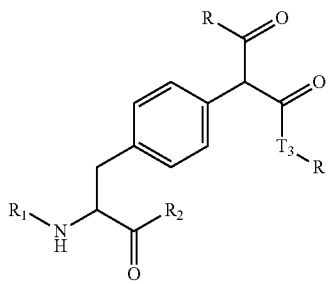

wherein: R is H, halogen, alkyl, substituted alkyl, cycloalkyl, or substituted cycloalkyl; and $T_3$ is O, or S. Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXXIII) are included:

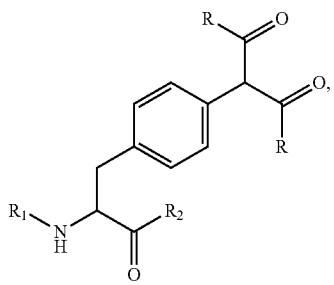

wherein: R is H, halogen, alkyl, substituted alkyl, cycloalkyl, or substituted cycloalkyl.

In addition, the following amino acids having structures of Formula (XXXXIII) are included:

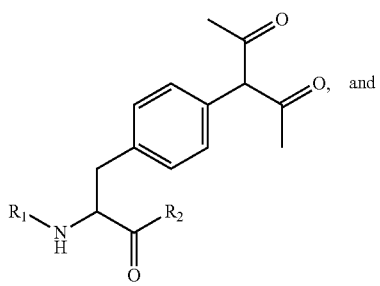

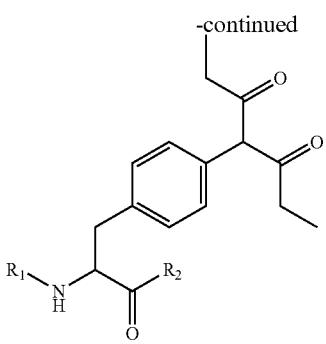

Such non-natural amino acids may be in the form of a salt, or may be incorporated into a non-natural amino acid polypeptide, polymer, polysaccharide, or a polynucleotide and optionally post translationally modified.

Non-natural amino acids containing a hydroxylamine (also called an aminooxy) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain carbonyl- or dicarbonyl-groups, including but not limited to, ketones, aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34(9): 727-736 (2001). Whereas the result of reaction with a hydrazine group is the corresponding hydrazone, however, an oxime results generally from the reaction of an aminooxy group with a carbonyl- or dicarbonyl-containing group such as, by way of example, a ketones, aldehydes or other functional groups with similar chemical reactivity.

Thus, in certain embodiments described herein are non-natural amino acids with sidechains comprising a hydroxylamine group, a hydroxylamine-like group (which has reactivity similar to a hydroxylamine group and is structurally similar to a hydroxylamine group), a masked hydroxylamine group (which can be readily converted into a hydroxylamine group), or a protected hydroxylamine group (which has reactivity similar to a hydroxylamine group upon deprotection). Such amino acids include amino acids having the structure of Formula (XIV):

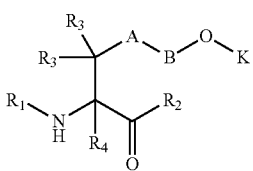

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; K is —NR$_6$R$_7$ or —N=CR$_6$R$_7$; R$_1$ is H, an amino protecting group, resin, amino acid, polypeptide, or polynucleotide; and R$_2$ is OH, an ester protecting group, resin, amino acid, polypeptide, or polynucleotide; each of R$_3$ and R$_4$ is independently H, halogen, lower alkyl, or substituted lower alkyl, or R$_3$ and R$_4$ or two R$_3$ groups optionally form a cycloalkyl or a heterocycloalkyl; each of R$_6$ and R$_7$ is independently selected from the group consisting of H, alkyl, substituted alkyl, alkenyl, substituted alkenyl, alkoxy, substituted alkoxy, polyalkylene oxide, substituted polyalkylene oxide, aryl, substituted aryl, heteroaryl, substituted heteroaryl, alkaryl, substituted alkaryl, aralkyl, and substituted aralkyl, —C(O)R", —C(O)$_2$R", —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or R$_6$ or R$_7$ is L-X, where X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination thereof; and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

In certain embodiments of compounds of Formula (XIV), A is phenylene or substituted phenylene. In certain embodiments of compounds of Formula (XIV), B is -(alkylene or substituted alkylene)-, —O-(alkylene or substituted alkylene)-, —S-(alkylene or substituted alkylene)-, or —C(O)-(alkylene or substituted alkylene)-. In certain embodiments of compounds of Formula (XIV), B is —O(CH$_2$)$_2$—, —S(CH$_2$)$_2$—, —NH(CH$_2$)$_2$—, —CO(CH$_2$)$_2$—, or —(CH$_2$)$_n$— where n is 1 to 4. In certain embodiments of compounds of Formula (XIV), R$_1$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (XIV), R$_1$ is a resin, amino acid, polypeptide, or polynucleotide. In certain embodiments of compounds of Formula (XIV), wherein R$_2$ is OH, O-methyl, O-ethyl, or O-t-butyl. In certain embodiments of compounds of Formula (XIV), R$_2$ is a resin, amino acid, polypeptide, or polynucleotide. In certain embodiments of compounds of Formula (XIV), R$_2$ is a polynucleotide. In certain embodiments of compounds of Formula (XIV), R$_2$ is ribonucleic acid (RNA). In certain embodiments of compounds of Formula (XIV), R$_2$ is tRNA. In certain embodiments of compounds of Formula (XIV), the tRNA specifically recognizes a codon selected from the group consisting of an amber codon, ochre codon, opal codon, a unique codon, a rare codon, an unnatural codon, a five-base codon, and a four-base codon. In certain embodiments of compounds of Formula (XIV), R$_2$ is a suppressor tRNA. In certain embodiments of compounds of Formula (XIV), each of R$_6$ and R$_7$ is independently selected from the group consisting of H, alkyl, substituted alkyl, alkoxy, substituted alkoxy, polyalkylene oxide, substituted polyalkylene oxide, aryl, substituted aryl, heteroaryl, substituted heteroaryl, alkaryl, substituted alkaryl, aralkyl, and substituted aralkyl. In certain embodiments of compounds of Formula (XIV), each of R$_6$ and R$_7$ is independently selected from the group consisting of H, methyl, phenyl, and -[(alkylene or substituted alkylene)-O-(hydrogen, alkyl, or substituted alkyl)]$_x$, wherein x is from 1-50. In certain embodiments of compounds of Formula (XIV), K is —NR$_6$R$_7$.

In certain embodiments of compounds of Formula (XIV), X is a biologically active agent selected from the group consisting of a peptide, protein, enzyme, antibody, drug, dye, lipid, nucleosides, oligonucleotide, cell, virus, liposome, microparticle, and micelle. In certain embodiments of compounds of Formula (XIV), X is a drug selected from the group consisting of an antibiotic, fungicide, anti-viral agent, anti-inflammatory agent, anti-tumor agent, cardiovascular agent, anti-anxiety agent, hormone, growth factor, and steroidal agent. In certain embodiments of compounds of Formula (XIV), X is an enzyme selected from the group consisting of horseradish peroxidase, alkaline phosphatase, β-galactosidase, and glucose oxidase. In certain embodiments of compounds of Formula (XIV), X is a detectable label selected from the group consisting of a fluorescent, phosphorescent, chemiluminescent, chelating, electron dense, magnetic, intercalating, radioactive, chromophoric, and energy transfer moiety.

In certain embodiments, compounds of Formula (XIV) are stable in aqueous solution for at least 1 month under mildly acidic conditions. In certain embodiments, compounds of Formula (XIV) are stable for at least 2 weeks under mildly acidic conditions. In certain embodiments, compound of Formula (XIV) are stable for at least 5 days under mildly acidic conditions. In certain embodiments, such acidic conditions are pH 2 to 8.

Such amino acids include amino acids having the structure of Formula (XV):

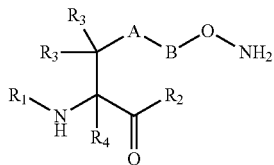

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; $R_1$ is H, an amino protecting group, resin, amino acid, polypeptide, or polynucleotide; and $R_2$ is OH, an ester protecting group, resin, amino acid, polypeptide, or polynucleotide; each of $R_3$ and $R_4$ is independently H, halogen, lower alkyl, or substituted lower alkyl, or $R_3$ and $R_4$ or two $R_3$ groups optionally form a cycloalkyl or a heterocycloalkyl. Such non-natural amino acids may be in the form of a salt, or may be incorporated into a non-natural amino acid polypeptide, polymer, polysaccharide, or a polynucleotide and optionally post translationally modified.

A non-limiting, representative amino acid has the following structure:

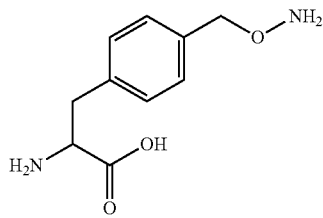 [SMILES: NOCc1ccc(CC(N)C(=O)O)cc1]

Such a non-natural amino acid may be in the form of a salt, or may be incorporated into a non-natural amino acid polypeptide, polymer, polysaccharide, or a polynucleotide and optionally post translationally modified.

Non-natural amino acids containing an oxime group allow for reaction with a variety of reagents that contain certain reactive carbonyl- or dicarbonyl-groups (including but not limited to, ketones, aldehydes, or other groups with similar reactivity) to form new non-natural amino acids comprising a new oxime group. Such an oxime exchange reaction allow for the further functionalization of non-natural amino acid polypeptides. Further, the original non-natural amino acids containing an oxime group may be useful in their own right as long as the oxime linkage is stable under conditions necessary to incorporate the amino acid into a polypeptide (e.g., the in vivo, in vitro and chemical synthetic methods described herein).

Thus, in certain embodiments described herein are non-natural amino acids with sidechains comprising an oxime group, an oxime-like group (which has reactivity similar to an oxime group and is structurally similar to an oxime group), a masked oxime group (which can be readily converted into an oxime group), or a protected oxime group (which has reactivity similar to an oxime group upon deprotection). Such amino acids include amino acids having the structure of Formula (XI):

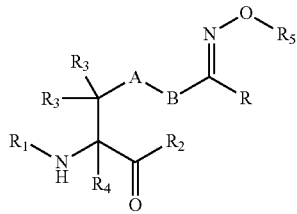

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; R is H, alkyl, substituted alkyl, cycloalkyl, or substituted cycloalkyl; $R_1$ is H, an amino protecting group, resin, amino acid, polypeptide, or polynucleotide; and $R_2$ is OH, an ester protecting group, resin, amino acid, polypeptide, or polynucleotide; each of $R_3$ and $R_4$ is independently H, halogen, lower alkyl, or substituted lower alkyl, or $R_3$ and $R_4$ or two $R_3$ optionally form a cycloalkyl or a heterocycloalkyl; $R_5$ is H, alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, substituted aralkyl, -(alkylene or substituted alkylene)-ON(R")$_2$, -(alkylene or substituted alkylene)-C(O)SR", -(alkylene or substituted alkylene)-S—S-(aryl or substituted aryl), —C(O)R", —C(O)$_2$R", or —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or $R_5$ is L-X, where X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination thereof; and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; with a proviso that when A and B are absent, R is not methyl. Such non-natural amino acids may be in the form of a salt, or may be incorporated into a non-natural amino acid polypeptide, polymer, polysaccharide, or a polynucleotide and optionally post translationally modified.

In certain embodiments of compounds of Formula (XI), B is —O-(alkylene or substituted alkylene)-. In certain embodiments of compounds of Formula (XI), B is —O(CH$_2$)—. In certain embodiments of compounds of Formula (XI), R is C$_{1-4}$ alkyl. In certain embodiments of compounds of Formula (XI), R is —CH$_3$. In certain embodiments of compounds of Formula (XI), $R_1$ is H, tert-butyloxycarbonyl (Boc), 9-fluorenylmethoxycarbonyl (Fmoc), N-acetyl, tetrafluoroacetyl (TFA), or benzyloxycarbonyl (Cbz). In certain embodiments of compounds of Formula (XI), $R_1$ is a resin, amino acid, polypeptide, or polynucleotide. In certain embodiments of compounds of Formula (XI), $R_2$ is OH, O-methyl, O-ethyl, or O-t-butyl. In certain embodiments of compounds of Formula (XI), $R_2$ is a resin, amino acid, polypeptide, or polynucleotide. In certain embodiments of compounds of Formula (XI), $R_2$ is a polynucleotide. In certain embodiments of compounds of Formula (XI), $R_2$ is ribonucleic acid (RNA). In certain embodiments of compounds of Formula (XI), $R_2$ is tRNA. In certain embodiments of compounds of Formula (XI), the tRNA specifically recognizes a selector codon. In certain embodiments of compounds of Formula (XI), the selector codon is selected from the group consisting of an amber codon, ochre codon, opal codon, a unique codon, a rare codon, an unnatural codon, a five-base codon, and a four-base codon. In certain embodiments of compounds of Formula (XI), $R_2$ is a suppressor tRNA. In certain embodiments of compounds of Formula (XI), $R_5$ is alkylalkoxy, substituted alkylalkoxy, polyalkylene oxide, substituted polyalkylene oxide, or —C(O)$_2$R". In certain embodiments of compounds of Formula (XI), $R_5$ is -[(alkylene or substituted alkylene)-O-(hydrogen, alkyl, or substituted alkyl)]$_x$, wherein x is from 1-50. In certain embodiments of compounds of Formula (XI), $R_5$ is —(CH$_2$CH$_2$)—O—CH$_3$ or —COOH.

In certain embodiments, compounds of Formula (XI) are stable in aqueous solution for at least 1 month under mildly acidic conditions. In certain embodiments, compounds of Formula (XI) are stable for at least 2 weeks under mildly acidic conditions. In certain embodiments, compound of Formula (XI) are stable for at least 5 days under mildly acidic conditions. In certain embodiments, such acidic conditions are pH 2 to 8.

Amino acids of Formula (XI) include amino acids having the structure of Formula (XII):

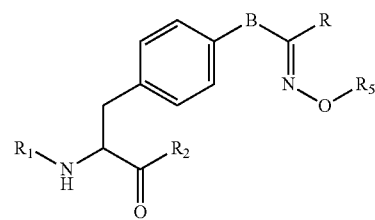

wherein, B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')═N—, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; R is H, alkyl, substituted alkyl, cycloalkyl, or substituted cycloalkyl; R$_1$ is H, an amino protecting group, resin, amino acid, polypeptide, or polynucleotide; and R$_2$ is OH, an ester protecting group, resin, amino acid, polypeptide, or polynucleotide; R$_5$ is H, alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, substituted aralkyl, -(alkylene or substituted alkylene)-ON(R")$_2$, -(alkylene or substituted alkylene)-C(O)SR", -(alkylene or substituted alkylene)-S—S-(aryl or substituted aryl), —C(O)R", —C(O)$_2$R", or —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or R$_5$ is L-X, where X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination thereof; and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

Such amino acids include amino acids having the structure of Formula (XIII):

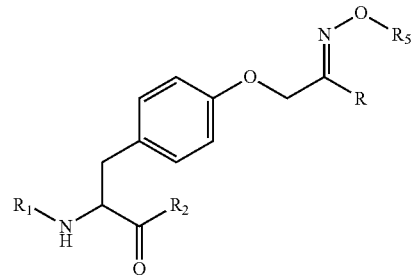

wherein, R is H, alkyl, substituted alkyl, cycloalkyl, or substituted cycloalkyl; R$_1$ is H, an amino protecting group, resin, amino acid, polypeptide, or polynucleotide; and R$_2$ is OH, an ester protecting group, resin, amino acid, polypeptide, or polynucleotide; R$_5$ is H, alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, substituted aralkyl, -(alkylene or substituted alkylene)-ON(R")$_2$, -(alkylene or substituted alkylene)-C(O)SR", -(alkylene or substituted alkylene)-S—S-(aryl or substituted aryl), —C(O)R", —C(O)$_2$R", or —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or R$_5$ is L-X, where X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group;

a magnetic group; an intercalating group; a chromophore; an energy transfer agent; a biologically active agent; a detectable label; and any combination thereof; and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

Further non-limiting examples of such amino acids include amino acids having the following structures:

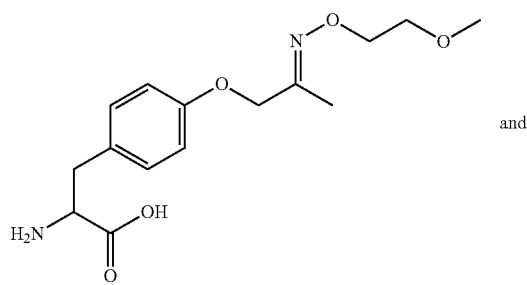

and

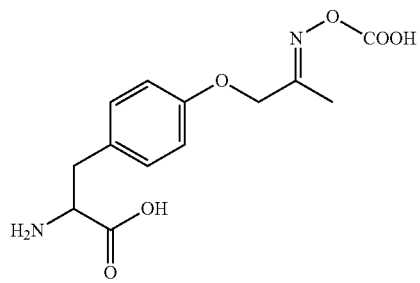

Such non-natural amino acids may be in the form of a salt, or may be incorporated into a non-natural amino acid polypeptide, polymer, polysaccharide, or a polynucleotide and optionally post translationally modified.

In addition, such amino acids include amino acids having the structure of Formula (XIV):

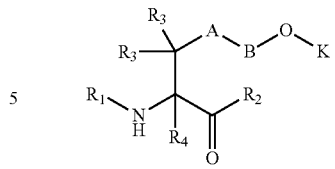

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; K is —NR$_6$R$_7$ or —N=CR$_6$R$_7$; R$_1$ is H, an amino protecting group, resin, amino acid, polypeptide, or polynucleotide; and R$_2$ is OH, an ester protecting group, resin, amino acid, polypeptide, or polynucleotide; each of R$_3$ and R$_4$ is independently H, halogen, lower alkyl, or substituted lower alkyl, or R$_3$ and R$_4$ or two R$_3$ groups optionally form a cycloalkyl or a heterocycloalkyl; each of R$_6$ and R$_7$ is independently selected from the group consisting of H, alkyl, substituted alkyl, alkenyl, substituted alkenyl, alkoxy, substituted alkoxy, polyalkylene oxide, substituted polyalkylene oxide, aryl, substituted aryl, heteroaryl, substituted heteroaryl, alkaryl, substituted alkaryl, aralkyl, and substituted aralkyl, —C(O)R", —C(O)$_2$R", —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or R$_6$ or R$_7$ is L-X, where X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination thereof; and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

Such amino acids further include amino acids having the structure of Formula (XVI):

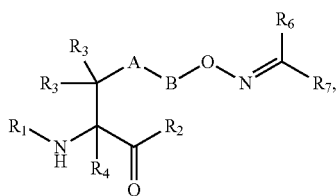

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; $R_1$ is H, an amino protecting group, resin, amino acid, polypeptide, or polynucleotide; and $R_2$ is OH, an ester protecting group, resin, amino acid, polypeptide, or polynucleotide; each of $R_3$ and $R_4$ is independently H, halogen, lower alkyl, or substituted lower alkyl, or $R_3$ and $R_4$ or two $R_3$ optionally form a cycloalkyl or a heterocycloalkyl; each of $R_6$ and $R_7$ is independently selected from the group consisting of H, alkyl, substituted alkyl, alkenyl, substituted alkenyl, alkoxy, substituted alkoxy, polyalkylene oxide, substituted polyalkylene oxide, aryl, substituted aryl, heteroaryl, substituted heteroaryl, alkaryl, substituted alkaryl, aralkyl, and substituted aralkyl, —C(O)R", —C(O)$_2$R", —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or $R_6$ or $R_7$ is L-X, where X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination thereof, and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.

Further, such amino acids include amino acids having the structure of Formula (XVII):

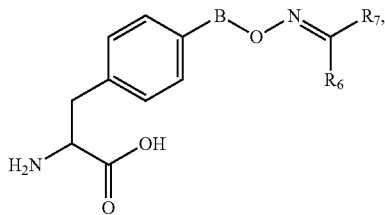

wherein: B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; $R_1$ is H, an amino protecting group, resin, amino acid, polypeptide, or polynucleotide; and $R_2$ is OH, an ester protecting group, resin, amino acid, polypeptide, or polynucleotide; each of $R_6$ and $R_7$ is independently selected from the group consisting of H, alkyl, substituted alkyl, alkenyl, substituted alkenyl, alkoxy, substituted alkoxy, polyalkylene oxide, substituted polyalkylene oxide, aryl, substituted aryl, heteroaryl, substituted heteroaryl, alkaryl, substituted alkaryl, aralkyl, and substituted aralkyl, —C(O)R", —C(O)$_2$R", —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or $R_6$ or $R_7$ is L-X, where X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination thereof; and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl.

Non-limiting examples of such amino acids include amino acids having the following structures:

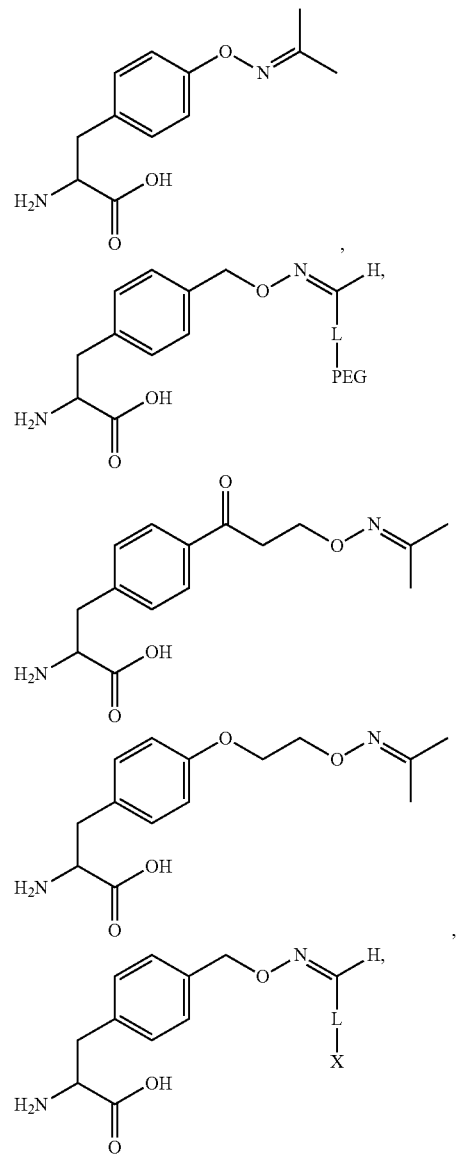

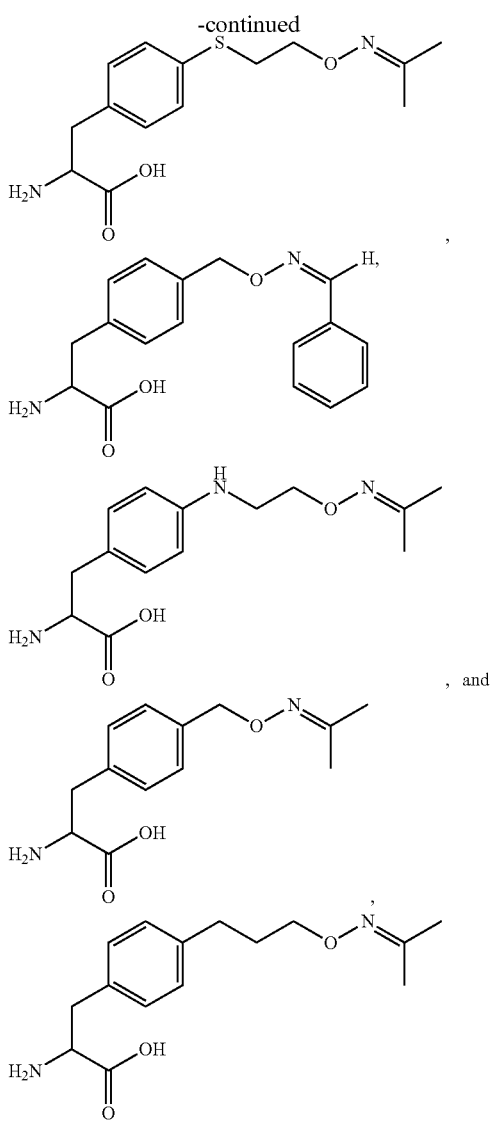

Such non-natural amino acids may be in the form of a salt, or may be incorporated into a non-natural amino acid polypeptide, polymer, polysaccharide, or a polynucleotide and optionally post translationally modified.

Additionally, such amino acids include amino acids having the structure of Formula (XVIII):

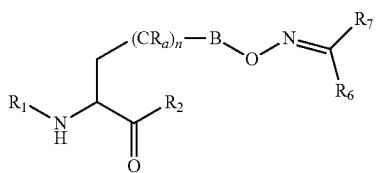

wherein: B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; $R_1$ is H, an amino protecting group, resin, amino acid, polypeptide, or polynucleotide; and $R_2$ is OH, an ester protecting group, resin, amino acid, polypeptide, or polynucleotide; each of $R_6$ and $R_7$ is independently selected from the group consisting of H, alkyl, substituted alkyl, alkenyl, substituted alkenyl, alkoxy, substituted alkoxy, polyalkylene oxide, substituted polyalkylene oxide, aryl, substituted aryl, heteroaryl, substituted heteroaryl, alkaryl, substituted alkaryl, aralkyl, and substituted aralkyl, —C(O)R", —C(O)$_2$R", —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or $R_6$ or $R_7$ is L-X, where X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination thereof; and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; and each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R'; where each R' is independently H, alkyl, or substituted alkyl and n is 0 to 8. Such non-natural amino acids may be in the form of a salt, or may be incorporated into a non-natural amino acid polypeptide, polymer, polysaccharide, or a polynucleotide and optionally post translationally modified.

Non-limiting examples of such amino acids include amino acids having the following structures:

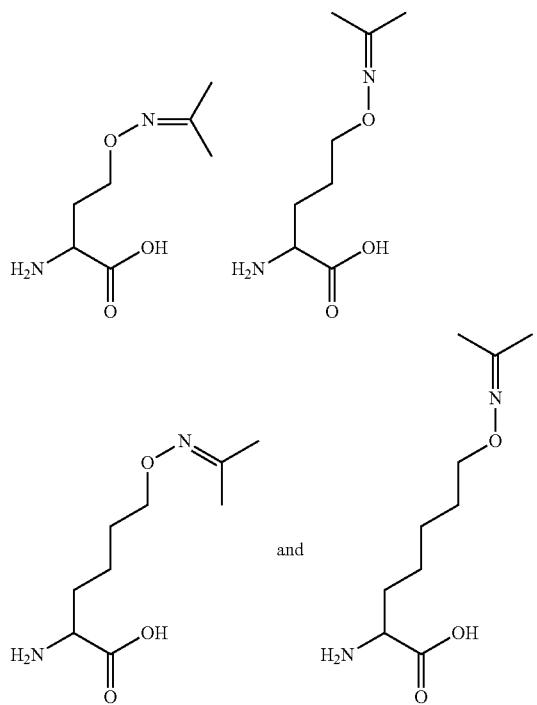

and

Such non-natural amino acids may be in the form of a salt, or may be incorporated into a non-natural amino acid polypeptide, polymer, polysaccharide, or a polynucleotide and optionally post translationally modified.

In certain embodiments, the non-natural amino acid can be according to formula XIX:

Formula XIX

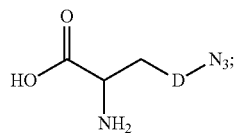

or a salt thereof, wherein: D is —Ar—$W_3$— or —$W_1$—$Y_1$—C(O)—$Y_2$—$W_2$—; Ar is

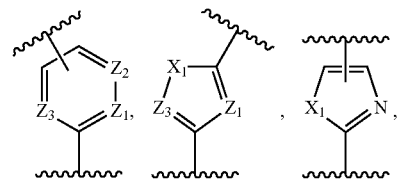

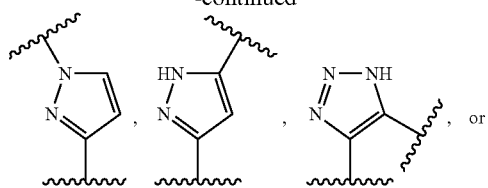

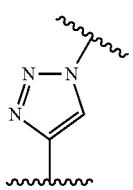

each of $W_1$, $W_2$, and $W_3$ is independently a single bond or lower alkylene; each $X_1$ is independently —NH—, —O—, or —S—; each $Y_1$ is independently a single bond, —NH—, or —O—; each $Y_2$ is independently a single bond, —NH—, —O—, or an N-linked or C-linked pyrrolidinylene; and one of $Z_1$, $Z_2$, and $Z_3$ is —N— and the others of $Z_1$, $Z_2$, and $Z_3$ are independently —CH—. In certain embodiments, the non-natural amino acid is according to formula XIXa:

Formula XIXa

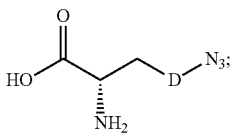

where D is a defined in the context of formula XIX. In certain embodiments, the non-natural amino acid is according formula XIXb:

Formula XIXb

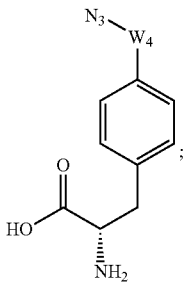

or a salt thereof, wherein $W_4$ is $C_1$-$C_{10}$ alkylene. In a further embodiment, $W_4$ is $C_1$-$C_5$ alkylene. In an embodiment, $W_4$ is $C_1$-$C_3$ alkylene. In an embodiment, $W_4$ is $C_1$ alkylene. In particular embodiments, the non-natural amino acid is selected from the group consisting of:

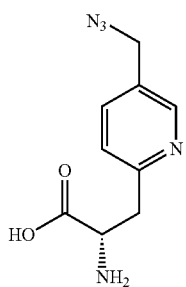
(1)
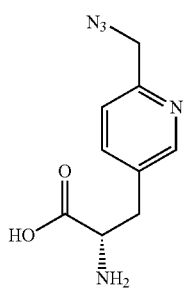
(2)
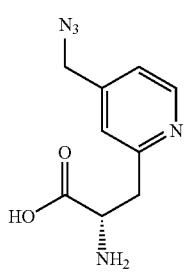
(3)
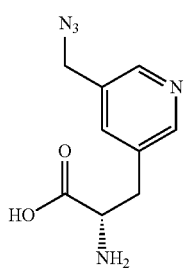
(4)
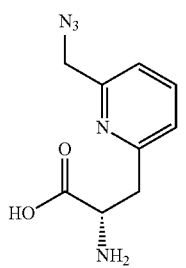
(5)
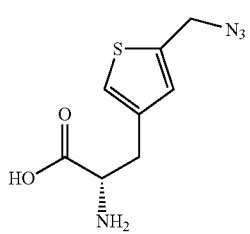
(6)
-continued
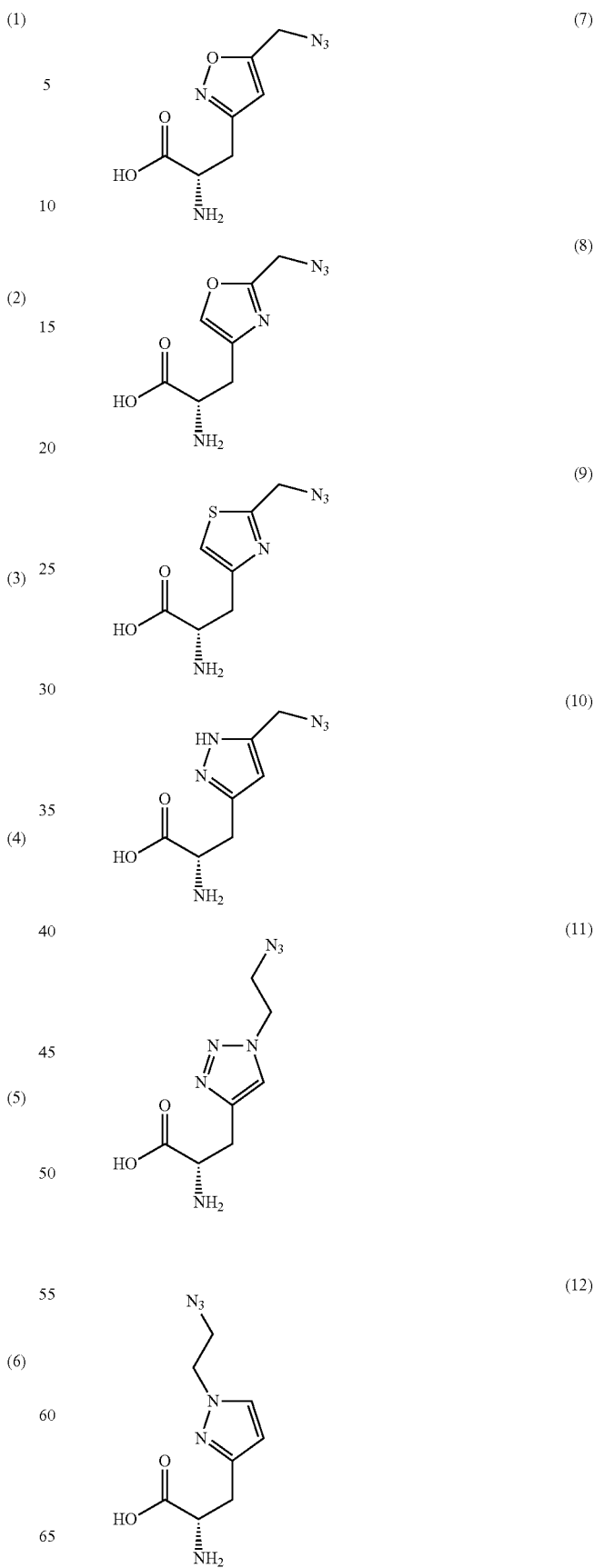

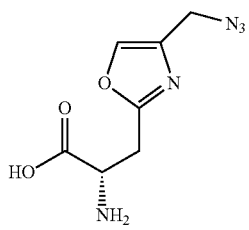
(13)
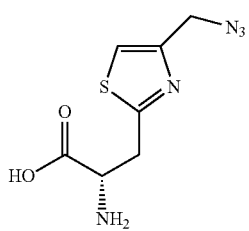
(14)
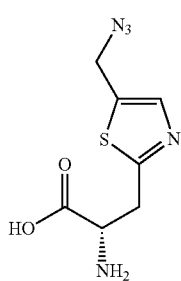
(15)
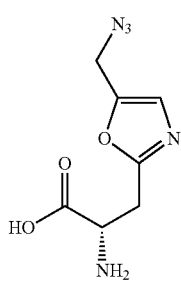
(16)
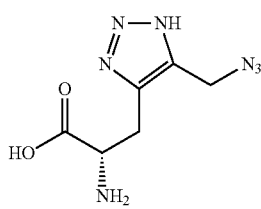
(17)
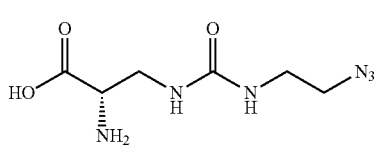
(18)
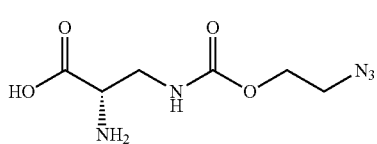
(19)

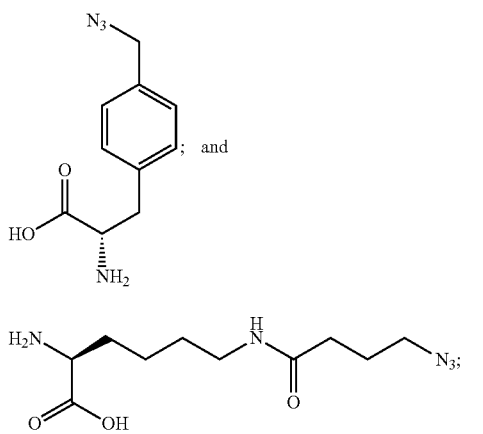

or a salt thereof. Such non-natural amino acids may be in the form of a salt, or may be incorporated into a non-natural amino acid polypeptide, polymer, polysaccharide, or a polynucleotide and optionally post translationally modified.

Linkers and Payloads

In certain embodiments, the antibody comprises a non-natural amino acid having a reactive group, as described above. One of skill in the art can use the reactive group to link the antibody to any molecular entity capable of forming a covalent bond to the non-natural amino acid, directly or indirectly via a linker.

Useful linkers include those described in the section above. In certain embodiments, the linker is any divalent or multivalent linker known to those of skill in the art. Generally, the linker is capable of forming covalent bonds to the functional moiety R and the alpha carbon of the non-natural amino acid. Useful divalent linkers a bond, alkylene, substituted alkylene, heteroalkylene, substituted heteroalkylene, arylene, substituted arylene, heteroarlyene and substituted heteroarylene. In certain embodiments, the linker is $C_{1-10}$ alkylene or $C_{1-10}$ heteroalkylene.

The molecular payload can be any molecular entity that one of skill in the art might desire to conjugate to the antibody. In certain embodiments, the payload is a therapeutic moiety. In such embodiment, the antibody conjugate can be used to target the therapeutic moiety to its molecular target. In certain embodiments, the payload is a labeling moiety. In such embodiments, the antibody conjugate can be used to detect binding of the antibody to its target. In certain embodiments, the payload is a cytotoxic moiety. In such embodiments, the conjugate can be used target the cytotoxic moiety to a diseased cell, for example a cancer cell, to initiate destruction or elimination of the cell. Conjugates comprising other molecular payloads apparent to those of skill in the art are within the scope of the conjugates described herein.

In certain embodiments, a conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof.

Useful drug payloads include any cytotoxic, cytostatic or immunomodulatory drug. Useful classes of cytotoxic or immunomodulatory agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, calmodulin inhibitors, chemotherapy sensitizers, duocarmycins, etoposides, fluorinated pyrimidines, ionophores, lexitropsins, maytansinoids, nitrosoureas, platinols, pore-forming compounds, purine antimetabolites, puromycins, radiation sensitizers, rapamycins, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, calicheamicin, calicheamicin derivatives, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, DM1, DM4, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophycins, cemadotin, maytansinoids, discodermolide, eleutherobin, and mitoxantrone.

In some embodiments, the payload is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other anti-tubulin agents include, for example, baccatin derivatives, taxane analogs, epothilones (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid can be maytansine or DM-1 (ImmunoGen, Inc.; see also Chari et al., 1992, Cancer Res. 52:127-131).

In some embodiments, the payload is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In some embodiments, the payload is not a radioisotope. In some embodiments, the payload is not radioactive.

In some embodiments, the payload is an antimetabolite. The antimetabolite can be, for example, a purine antagonist (e.g., azothioprine or mycophenolate mofetil), a dihydrofolate reductase inhibitor (e.g., methotrexate), acyclovir, ganciclovir, zidovudine, vidarabine, ribavarin, azidothymidine, cytidine arabinoside, amantadine, dideoxyuridine, iododeoxyuridine, poscarnet, or trifluridine.

In other embodiments, the payload is tacrolimus, cyclosporine, FU506 or rapamycin. In further embodiments, the Drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin (MYLOTARG®), goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab (HERCEPTIN®), tretinoin, uracil mustard, valrubicin, vinblastine, vincristine, vinorelbine or zoledronate.

In some embodiments, the payload is an immunomodulatory agent. The immunomodulatory agent can be, for example, ganciclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, indomethacin, ketoprofen, nabumetone, sulindac, tenoxicam and tolmetin.

Suitable lipoxygenase inhibitors include redox inhibitors (e.g., catechol butane derivatives, nordihydroguaiaretic acid (NDGA), masoprocol, phenidone, lanopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

Other useful drug payloads include chemical compounds useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethyl enephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Other useful payloads include: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. Nos. 5,863,949, 5,861,510, and EP 780, 386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)qu-inazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

In certain embodiments, the payload is an antibody or an antibody fragment. In certain embodiments, the payload antibody or fragment can be encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibodies and antibody fragments recognized by those of skill in the art, and variants thereof. Exemplary fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, and the like.

In certain embodiments, the payload is one or more water-soluble polymers. A wide variety of macromolecular polymers and other molecules can be linked to antigen-binding polypeptides of the present invention to modulate biological properties of the antibody, and/or provide new biological properties to the antibody. These macromolecular polymers can be linked to the antibody via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more.

The polymer selected may be water soluble so that the protein to which it is attached does not precipitate in an aqueous environment, such as a physiological environment. The polymer may be branched or unbranched. Preferably, for therapeutic use of the end-product preparation, the polymer will be pharmaceutically acceptable.

The proportion of polyethylene glycol molecules to antibody molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the antibody by the formula: XO—(CH$_2$CH$_2$O)$_{=n}$—CH$_2$CH$_2$—Y where n is 2 to 10,000 and X is H or a terminal modification, including but not limited to, a C$_{1-4}$ alkyl.

In some cases, a PEG used in the invention terminates on one end with hydroxy or methoxy, i.e., X is H or CH$_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to an antigen-binding polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the antibody to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the antibody via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the antibody variant with a PEG derivative contains a chemical functionality that is reactive with the chemical functionality present on the side chain of the non-naturally encoded amino acid.

In certain embodiments, the payload is an azide- or acetylene-containing polymer comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene)glycol and other related polymers, including poly (dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(-YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight: -PEG-CO$_2$—PEG-+H$_2$O→PEG-CO$_2$H+HO-PEG- It is understood by those skilled in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure: X-A-POLY-B —N=N=N wherein: N=N=N is an azide moiety; B is a linking moiety, which may be present or absent; POLY is a water-soluble non-antigenic polymer; A is a linking moiety, which may be present or absent and which may be the same as B or different; and X is a second functional group. Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those skilled in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182: 1379 (1981), Zaplipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zaplipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Macrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments of the present invention, the polymer derivatives of the invention comprise a polymer backbone having the structure: X—$CH_2CH_2O$—($CH_2CH_2O$)$_n$—$CH_2CH_2$—N=N=N wherein: X is a functional group as described above; and n is about 20 to about 4000. In another embodiment, the polymer derivatives of the invention comprise a polymer backbone having the structure: X—$CH_2CH_2O$—($CH_2CH_2O$)$_n$—$CH_2CH_2$—O—($CH_{-2}$)$_m$—W—N=N=N wherein: W is an aliphatic or aromatic linker moiety comprising between 1-10 carbon atoms; n is about 20 to about 4000; X is a functional group as described above; and m is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer as shown in the following: X-PEG-L+$N_3^-$→X-PEG-$N_3$.

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below: X-PEG-M+N-linker-N=N=N→PG-X-PEG-linker-N=N=N wherein: PEG is poly(ethylene glycol) and X is a capping group such as alkoxy or a functional group as described above; and M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality: BocHN-PEG-$NH_2$+$HO_2$C—($CH_2$)$_3$—N=N=N.

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure: X-A-POLY—B—C≡C—R wherein: R can be either H or an alkyl, alkene, alkyoxy, or aryl or substituted aryl group; B is a linking moiety, which may be present or absent; POLY is a water-soluble non-antigenic polymer; A is a linking moiety, which may be present or absent and which may be the same as B or different; and X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure: X—CH$_2$CH$_2$O—(CH$_2$CH$_2$O)$_n$—CH$_2$CH$_2$—O—(CH$_2$)$_m$—C≡CH wherein: X is a functional group as described above; n is about 20 to about 4000; and m is between 1 and 10. Specific examples of each of the heterobifunctional PEG polymers are shown below.

The acetylene-containing PEG derivatives of the invention can be prepared using methods known to those skilled in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer: X-PEG-Nu+L-A-C→X-PEG-Nu-A-C≡CR'.

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group.

In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

Water soluble polymers can be linked to the antibodies of the invention. The water soluble polymers may be linked via a non-naturally encoded amino acid incorporated in the antibodies or any functional group or substituent of a non-naturally encoded or naturally encoded amino acid, or any functional group or substituent added to a non-naturally encoded or naturally encoded amino acid. Alternatively, the water soluble polymers are linked to an antigen-binding polypeptide incorporating a non-naturally encoded amino acid via a naturally-occurring amino acid (including but not limited to, cysteine, lysine or the amine group of the N-terminal residue). In some cases, the antibodies of the invention comprise 1, 2, 3, 4, 5, 6, 7, 8, 9, 10 non-natural amino acids, wherein one or more non-naturally-encoded amino acid(s) are linked to water soluble polymer(s) (including but not limited to, PEG and/or oligosaccharides). In some cases, the antibodies of the invention further comprise 1, 2, 3, 4, 5, 6, 7, 8, 9, 10, or more naturally-encoded amino acid(s) linked to water soluble polymers. In some cases, the antibody of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the antibodies relative to the unconjugated form.

The number of water soluble polymers linked to an antigen-binding polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of antibody is increased at least about 10, 20, 30, 40, 50, 60, 70, 80, 90 percent, 2-fold, 5-fold, 10-fold, 50-fold, or at least about 100-fold over an unmodified polypeptide.

In one embodiment of the present invention, an antigen-binding polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure: RO—(CH$_2$CH$_2$O)$_n$—O—(CH$_2$)$_m$—O—NH$_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure: RO—(CH$_2$CH$_2$O)$_n$—O—(CH$_2$)$_m$—X—NH—NH$_2$ where R is a simple alkyl (methyl, ethyl, propyl, etc.), m is 2-10 and n is 100-1,000 and X is optionally a carbonyl group (C═O) that can be present or absent.

In some embodiments, the semicarbazide-containing PEG derivative will have the structure: RO—(CH$_2$CH$_2$O)$_n$—O—(CH$_2$)$_m$—NH—C(O)—NH—NH$_2$ where R is a simple alkyl (methyl, ethyl, propyl, etc.), m is 2-10 and n is 100-1,000.

In another embodiment of the invention, an antigen-binding polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure: RO—(CH$_2$CH$_2$O)$_n$—O—(CH$_2$)$_2$—NH—C(O)(CH$_2$)$_m$—O—NH$_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure: RO—(CH$_2$CH$_2$O)$_n$—O—(CH$_2$)$_2$—NH—C(O)(CH$_2$)$_m$—X—NH—NH$_2$ where R is a simple alkyl (methyl, ethyl, propyl, etc.), m is 2-10, n is 100-1,000 and X is optionally a carbonyl group (C═O) that can be present or absent.

In some embodiments, the semicarbazide-containing PEG derivatives have the structure: RO—(CH$_2$CH$_2$O)$_n$—O—(CH$_2$)$_2$—NH—C(O)(CH$_2$)$_m$—NH—C(O)—NH—NH$_2$ where R is a simple alkyl (methyl, ethyl, propyl, etc.), m is 2-10 and n is 100-1,000.

In another embodiment of the invention, an antibody comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, more preferably, from 5-20 kDa.

In another embodiment of the invention, an antibody comprising a non-naturally encoded amino acid is modified with a PEG derivative having a branched structure. For instance, in some embodiments, the hydrazine- or hydrazide-terminal PEG derivative will have the following structure: [RO—(CH$_2$CH$_2$O)$_n$—O—(CH$_2$)$_2$—NH—C(O)]$_2$CH(CH—$_2$)$_m$—X—NH—NH$_2$ where R is a simple alkyl (methyl, ethyl, propyl, etc.), m is 2-10 and n is 100-1,000, and X is optionally a carbonyl group (C═O) that can be present or absent.

In some embodiments, the PEG derivatives containing a semicarbazide group will have the structure: [RO—(CH$_2$CH$_2$O)$_n$—O—(CH$_2$)$_2$—C(O)—NH—CH$_2$—CH$_2$]$_2$CH—X—(CH$_2$)$_m$—NH—C(O)—NH—NH$_2$ where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure: [RO—(CH$_2$CH$_2$O)$_n$—O—(CH$_2$)$_2$—C(O)—NH—CH$_2$—CH$_2$]$_2$CH—X—(CH$_2$)$_m$—O—NH$_2$ where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the antibodies can modulate the binding of the antibodies to an antigen or receptor.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, Macronol. Chem. Phys. C25: 325-373 (1985); Scouten, Methods in Enzymology 135: 30-65 (1987); Wong et al., Enzyme Microb. Technol. 14: 866-874 (1992); Delgado et al., Critical Reviews in Therapeutic Drug Carrier Systems 9: 249-304 (1992); Zalipsky, Bioconjugate Chem. 6: 150-165 (1995).

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., App. Biochem. Biotech. 11: 141-45 (1985)). All references and patents cited are incorporated by reference herein.

PEGylation (i.e., addition of any water soluble polymer) of antigen-binding polypeptides containing a non-naturally encoded amino acid, such as p-azido-L-phenylalanine, is carried out by any convenient method. For example, antibody is PEGylated with an alkyne-terminated mPEG derivative. Briefly, an excess of solid mPEG(5000)-O—CH$_2$—

C≡CH is added, with stirring, to an aqueous solution of p-azido-L-Phe-containing antibody at room temperature. Typically, the aqueous solution is buffered with a buffer having a $pK_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated antibody variants from free mPEG(5000)-O—CH$_2$—C≡CH and any high-molecular weight complexes of the pegylated antibody which may form when unblocked PEG is activated at both ends of the molecule, thereby crosslinking antibody variant molecules. The conditions during hydrophobic interaction chromatography are such that free mPEG(5000)-O—CH$_2$—C≡CH flows through the column, while any crosslinked PEGylated antibody variant complexes elute after the desired forms, which contain one antibody variant molecule conjugated to one or more PEG groups. Suitable conditions vary depending on the relative sizes of the cross-linked complexes versus the desired conjugates and are readily determined by those skilled in the art. The eluent containing the desired conjugates is concentrated by ultrafiltration and desalted by diafiltration.

If necessary, the PEGylated antibodies obtained from the hydrophobic chromatography can be purified further by one or more procedures known to those skilled in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (PROTEIN PURIFICATION METHODS, A PRACTICAL APPROACH (Harris & Angal, Eds.) IRL Press 1989, 293-306). The purity of the antibody-PEG conjugate can be assessed by proteolytic degradation (including but not limited to, trypsin cleavage) followed by mass spectrometry analysis. Pepinsky B., et al., J. Pharmcol. & Exp. Ther. 297(3):1059-66 (2001).

A water soluble polymer linked to an amino acid of an antibody of the invention can be further derivatized or substituted without limitation.

In another embodiment of the invention, an antigen-binding polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure: RO—(CH$_2$CH$_2$O)$_n$—O—(CH$_2$)$_m$—N$_3$ where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure: RO—(CH$_2$CH$_2$O)$_n$—O—(CH$_2$)$_m$—NH—C(O)—(CH$_2$)$_p$—N$_3$, where R is a simple alkyl (methyl, ethyl, propyl, etc.), m is 2-10, p is 2-10 and n is 100-1,000 (i.e., average molecular weight is between 5-40 kDa).

In another embodiment of the invention, an antibody comprising a alkyne-containing amino acid is modified with a branched PEG derivative that contains a terminal azide moiety, with each chain of the branched PEG having a MW ranging from 10-40 kDa and, more preferably, from 5-20 kDa. For instance, in some embodiments, the azide-terminal PEG derivative will have the following structure: [RO—(CH$_2$CH$_2$O)$_n$—O—(CH$_2$)$_2$—NH—C(O)]$_2$CH(CH—$_2$)$_m$—X—(CH$_2$)$_p$—N$_3$ where R is a simple alkyl (methyl, ethyl, propyl, etc.), m is 2-10, p is 2-10, and n is 100-1,000, and X is optionally an O, N, S or carbonyl group (C=O), in each case that can be present or absent.

In another embodiment of the invention, an antigen-binding polypeptide is modified with a PEG derivative that contains an alkyne moiety that will react with an azide moiety present on the side chain of the non-naturally encoded amino acid.

In some embodiments, the alkyne-terminal PEG derivative will have the following structure: RO—(CH$_2$CH$_2$O)$_n$—O—(CH$_2$)$_m$—C≡CH where R is a simple alkyl (methyl, ethyl, propyl, etc.), m is 2-10 and n is 100-1,000 (i.e., average molecular weight is between 5-40 kDa).

In another embodiment of the invention, an antibody comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure: RO—(CH$_2$CH$_2$O)$_n$—O—(CH$_2$)$_m$—NH—C(O)—(CH$_2$)$_p$—C≡CH where R is a simple alkyl (methyl, ethyl, propyl, etc.), m is 2-10, p is 2-10 and n is 100-1,000.

In another embodiment of the invention, an antigen-binding polypeptide comprising an azide-containing amino acid is modified with a branched PEG derivative that contains a terminal alkyne moiety, with each chain of the branched PEG having a MW ranging from 10-40 kDa and, more preferably, from 5-20 kDa. For instance, in some embodiments, the alkyne-terminal PEG derivative will have the following structure: [RO—(CH$_2$CH$_2$O)$_n$—O—(CH$_2$)$_2$—NH—C(O)]$_2$CH(CH—$_2$)$_m$—X—(CH$_2$)$_p$C≡CH where R is a simple alkyl (methyl, ethyl, propyl, etc.), m is 2-10, p is 2-10, and n is 100-1,000, and X is optionally an O, N, S or carbonyl group (C=O), or not present.

In another embodiment of the invention, an antibody is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

Other exemplary PEG molecules that may be linked to antibodies, as well as PEGylation methods include those described in, e.g., U.S. Patent Publication Nos. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430;

2002/0040076; 2002/0037949; 2002/0002250; 2001/0056171; 2001/0044526; 2001/0027217; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,612,460; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

In certain embodiments, the antibodies can be linked to the payloads with one or more linkers capable of reacting with the non-natural amino acid. The one or more linkers can be any linkers apparent to those of skill in the art. The term "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide. Branched linkers may be used in antibodies of the invention. A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the antibody and the molecule linked to it. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody.

Any hetero- or homo-bifunctional linker can be used to link the conjugates. The linker may have a wide range of molecular weight or molecular length. Larger or smaller molecular weight linkers may be used to provide a desired spatial relationship or conformation between the antibody and the linked entity. Linkers having longer or shorter molecular length may also be used to provide a desired space or flexibility between the antibody and the linked entity. Similarly, a linker having a particular shape or conformation may be utilized to impart a particular shape or conformation to the antibody or the linked entity, either before or after the antibody reaches its target. The functional groups present on each end of the linker may be selected to modulate the release of an antibody or a payload under desired conditions. This optimization of the spatial relationship between the antibody and the linked entity may provide new, modulated, or desired properties to the molecule.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

Parent Antibodies

The parent antibody can be any antibody known to those of skill in the art, or later discovered, without limitation. The parent antibody may be substantially encoded by an antibody gene or antibody genes from any organism, including but not limited to humans, mice, rats, rabbits, camels, llamas, dromedaries, monkeys, particularly mammals and particularly human and particularly mice and rats. In one embodiment, the parent antibody may be fully human, obtained for example from a patient or subject, by using transgenic mice or other animals (Bruggemann & Taussig, 1997, Curr. Opin. Biotechnol. 8:455-458) or human antibody libraries coupled with selection methods (Griffiths & Duncan, 1998, Curr. Opin. Biotechnol. 9:102-108). The parent antibody may be from any source, including artificial or naturally occurring. For example parent antibody can be an engineered antibody, including but not limited to chimeric antibodies and humanized antibodies (Clark, 2000, Immunol. Today 21:397-402) or derived from a combinatorial library. In addition, the parent antibody may be an engineered variant of an antibody that is substantially encoded by one or more natural antibody genes. For example, in one embodiment the parent antibody is an antibody that has been identified by affinity maturation.

The parent antibody can have affinity to any antigen known to those of skill in the art, or later discovered. Virtually any substance may be an antigen for a parent antibody, or an antibody of the present description. Examples of useful antigens include, but are not limited to, Alpha-1 antitrypsin, Angiostatin, Antihemolytic factor, antibodies, Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), calcitonin, CC chemokines (e.g., monocyte chemoattractant protein-1, monocyte chemoattractant protein-2, monocyte chemoattractant protein-3, monocyte inflammatory protein-1 alpha, monocyte inflammatory protein-1 beta, RANTES, I309, R83915, R91733, HCC1, T58847, D31065, T64262), CD40 ligand, C-kit ligand, collagen, colony stimulating factor (CSF), complement factor 5a, complement inhibitor, complement receptor 1, cytokines, (e.g., epithelial neutrophil activating peptide-78, GRO/MGSA, GRO, GRO, MIP-1, MIP-1, MCP-1), epidermal growth factor (EGF), erythropoietin ("EPO"), exfoliating toxins A and B, factor IX, factor VII, factor VIII, factor X, fibroblast growth factor (FGF), fibrinogen, fibronectin, G-CSF, GM-CSF, glucocerebrosidase, gonadotropin, growth factors, hedgehog proteins (e.g., Sonic, Indian, Desert), hemoglobin, hepatocyte growth factor (HGF), hirudin, human serum albumin, insulin, insulin-like growth factor (IGF), interferons (e.g., IFN-α, IFN-, IFN-γ), interleukins (e.g., IL-1, IL-2, IL-3, IL-4, IL-5, IL-6, IL-7, IL-8, IL-9, IL-10, IL-11, IL-12, etc.), keratinocyte growth factor (KGF), lactoferrin, leukemia inhibitory factor, luciferase, neurturin, neutrophil inhibitory factor (NIF), oncostatin M, osteogenic protein, parathyroid hormone, PD-ECSF, PDGF, peptide hormones (e.g., human growth hormone), pleiotropin, protein A, protein G, pyrogenic exotoxins A, B, and C, relaxin, renin, SCF, soluble complement receptor I, soluble I-CAM 1, soluble interleukin receptors (IL-1, 2, 3, 4, 5, 6, 7, 9, 10, 11, 12, 13, 14, 15), soluble TNF receptor, somatomedin, somatostatin, somatotropin, streptokinase, superantigens, i.e., staphylococcal enterotoxins (SEA, SEB, SEC1, SEC2, SEC3, SED, SEE), superoxide dismutase, toxic shock syndrome toxin (TSST-1), thymosin alpha 1, tissue plasminogen activator, tumor necrosis factor (TNF beta), tumor necrosis factor receptor (TNFR), tumor necrosis factor-alpha (TNF alpha), vascular endothelial growth factor (VEGF), urokinase and others. These antigens can be obtained by methods known to those of skill in the art, for example, from commercial sources or from published polypeptide or polynucleotide sequences (e.g. Genbank).

Additional antigens include, but are not limited to, transcriptional and expression activators. Exemplary transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Antigens include, but are not limited to, expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Vaccine proteins may be antigens including, but not limited to, proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., *Plasmodia*), rhizopods (e.g., *Entamoeba*) and *flagellates* (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Antigens may be enzymes including, but not limited to, amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase may also be antigens.

For example, the antigen may be a disease-associated molecule, such as tumor surface antigen such as B-cell idiotypes, CD20 on malignant B cells, CD33 on leukemic blasts, and HER2/neu on breast cancer. Alternatively, the antigen may be a growth factor receptor. Examples of the growth factors include, but are not limited to, epidermal growth factors (EGFs), transferrin, insulin-like growth factor, transforming growth factors (TGFs), interleukin-1, and interleukin-2. For example, a high expression of EGF receptors has been found in a wide variety of human epithelial primary tumors. TGF-α has been found to mediate an autocrine stimulation pathway in cancer cells. Several murine monoclonal antibodies have been demonstrated to be able to bind EGF receptors, block the binding of ligand to EGF receptors, and inhibit proliferation of a variety of human cancer cell lines in culture and in xenograft medels. Mendelsohn and Baselga (1995) Antibodies to growth factors and receptors, in Biologic Therapy of Cancer, 2nd Ed., J B Lippincott, Philadelphia, pp 607-623. Thus, Antibodies of the invention may be used to treat a variety of cancers.

The antigen may also be cell surface protein or receptor associated with coronary artery disease such as platelet glycoprotein IIb/IIIa receptor, autoimmune diseases such as CD4, CAMPATH-1 and lipid A region of the gram-negative bacterial lipopolysaccharide. Humanized antibodies against CD4 have been tested in clinical trials in the treatment of patients with mycosis fungoides, generalized postular psoriasis, severe psoriasis, and rheumatoid arthritis. Antibodies against lipid A region of the gram-negative bacterial lipopolysaccharide have been tested clinically in the treatment of septic shock. Antibodies against CAMPATH-1 have also been tested clinically in the treatment of against refractory rheumatoid arthritis. Thus, antibodies provided herein may be used to treat a variety of autoimmune diseases.

Useful antigens also include proteins or peptides associated with human allergic diseases, such as inflammatory mediator proteins, e.g. interleukin-1 (IL-1), tumor necrosis factor (TNF), leukotriene receptor and 5-lipoxygenase, and adhesion molecules such as V-CAM/VLA-4. In addition, IgE may also serve as the antigen because IgE plays pivotal role in type I immediate hypersensitive allergic reactions such as asthma. Studies have shown that the level of total serum IgE tends to correlate with severity of diseases, especially in asthma. Burrows et al. (1989) "Association of asthma with serum IgE levels and skin-test reactivity to allergens" New Engl. L. Med. 320:271-277. Thus, Antibodies selected against IgE may be used to reduce the level of IgE or block the binding of IgE to mast cells and basophils in the treatment of allergic diseases without having substantial impact on normal immune functions.

The antigen may also be a viral surface or core protein which may serve as an antigen to trigger immune response of the host. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2).

The antigen may also be a mutated tumor suppressor gene product that has lost its tumor-suppressing function and may render the cells more susceptible to cancer. Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2. DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. p53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. Thus, Antibodies may be used to block the interactions of the gene product with other proteins or biochemicals in the pathways of tumor onset and development.

The antigen may be a CD molecule including but not limited to, CD1a, CD1b, CD1c, CD1d, CD2, CD3γ, CD3δ, CD3ε, CD4, CD5, CD6, CD7, CD8α, CD8β, CD9, CD10, CD11a, CD11b, CD11c, CDw12, CD13, CD14, CD15, CD15s, CD16a, CD16b, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45R, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD67, CD68, CD69, CDw70, CD71, CD72, CD73, CD74, CDw75, CDw76, CD77, CD79α, CD79β, CD80, CD81, CD82, CD83, CD84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CDw109, CD110-113, CD114, CD115, CD116, CD117, CD118, CD119, CD120a, CD120b, CD121a, CD121b, CD122, CD123, CDw124, CD125, CD126, CDw127, CDw128a, CDw128b, CD129, CDw130, CD131, CD132, CD133, CD134, CD135, CD136, CDw137, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCRζ. The antigen may be VEGF, VEGF receptor, EGFR, Her2, TNFa, TNFRI receptor, GPIIb/IIIa, IL-2R alpha chain, IL-2R beta chain, RSV F protein, alpha4 integrin, IgE, IgE receptor, digoxin, carpet viper venom, complement C5, OPGL, CA-125 tumor antigen, Staphylococci proteins, *Staphylococcus epidermidis* proteins, *Staphylococcus aureus* proteins, proteins involved Staphylococcal infection (including but not limited to, *Staphylococcus aureus* and *Staphylococcus epidermidis*), IL-6 receptor, CTLA-4, RSV, Tac subunit of IL-2 receptor, IL-5, and EpCam. In certain embodiments, the antigen is CD74. The antigen may be a fragment of a molecule.

Parent antibodies can be any antibody known in the art or any antibody developed by those of skill in the art without limitation. Examples include, but are not limited to anti-TNF antibody (U.S. Pat. No. 6,258,562), anti-IL-12 and/or anti-IL-12p40 antibody (U.S. Pat. No. 6,914,128); anti-IL-18 antibody (U. S. Patent Publication No. 2005/0147610), anti-05, anti-CBL, anti-CD147, anti-gp120, anti-VLA-4, anti-CD11a, anti-CD18, anti-VEGF, anti-CD40L, anti CD-40 (e.g., see PCT Publication No. WO 2007/124299) anti-Id, anti-ICAM-1, anti-CXCL13, anti-CD2, anti-EGFR, anti-TGF-beta 2, anti-HGF, anti-cMet, anti DLL-4, anti-NPR1, anti-PLGF, anti-ErbB3, anti-E-selectin, anti-Fact VII, anti-Her2/neu, anti-F gp, anti-CD11/18, anti-CD14, anti-ICAM-3, anti-RON, anti-SOST, anti CD-19, anti-CD80 (e.g., see PCT Publication No. WO 2003/039486, anti-CD4, anti-CD3, anti-CD23, anti-beta2-integrin, anti-alpha4beta7, anti-CD52, anti-HLA DR, anti-CD22 (e.g., see U.S. Pat. No. 5,789,554), anti-CD20, anti-MIF, anti-CD64 (FcR), anti-TCR alpha beta, anti-CD2, anti-Hep B, anti-CA 125, anti-EpCAM, anti-gp120, anti-CMV, anti-gpIIbIIIa, anti-IgE, anti-CD25, anti-CD33, anti-HLA, anti-IGF1,2, anti IGFR, anti-VNRintegrin, anti-IL-1alpha, anti-IL-1beta, anti-IL-1 receptor, anti-IL-2 receptor, anti-IL-4, anti-IL-4 receptor, anti-IL5, anti-IL-5 receptor, anti-IL-6, anti-IL-8, anti-IL-9, anti-IL-13, anti-IL-13 receptor, anti-IL-17, anti-IL-6R, anti-RANKL, anti-NGF, anti-DKK, anti-alphaVbeta3, anti-IL-17A, anti-IL23p19 and anti-IL-23 (see Presta, L. G. (2005)

J. Allergy Clin. Immunol. 116: 731-6 and www<dot>path<dot>cam<dot>ac<dot>uk</><dot>about<dot>mrc<7></>humanisation</>antibodies<dot>html).

Parent antibodies may also be selected from various therapeutic antibodies approved for use, in clinical trials, or in development for clinical use. Such therapeutic antibodies include, but are not limited to, rituximab (Rituxan®, IDEC/Genentech/Roche) (see, for example, U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT Application No. PCT/US2003/040426), trastuzumab (Herceptin®, Genentech) (see, for example, U.S. Pat. No. 5,677,171), a humanized anti-Her2/neu antibody approved to treat breast cancer; pertuzumab (rhuMab-2C4, Omnitarg®), currently being developed by Genentech; an anti-Her2 antibody (U.S. Pat. No. 4,753,894; cetuximab (Erbitux®, Imclone) (U.S. Pat. No. 4,943,533; PCT Publication No. WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Pat. No. 7,247,301), currently being developed by Genmab; 425, EMD55900, EMD62000, and EMD72000 (Merck KGaA) (U.S. Pat. No. 5,558,864; Murthy, et al. (1987) Arch. Biochem. Biophys. 252(2): 549-60; Rodeck, et al. (1987) J. Cell. Biochem. 35(4): 315-20; Kettleborough, et al. (1991) Protein Eng. 4(7): 773-83); ICR62 (Institute of Cancer Research) (PCT Publication No. WO 95/20045; Modjtahedi, et al. (1993) J. Cell. Biophys. 22(1-3): 129-46; Modjtahedi, et al. (1993) Br. J. Cancer 67(2): 247-53; Modjtahedi, et al. (1996) Br. J. Cancer 73(2): 228-35; Modjtahedi, et al. (2003) Int. J. Cancer 105(2): 273-80); TheraCIM hR3 (YM Biosciences, Canada and Centro de Immunologia Molecular, Cuba (U.S. Pat. Nos. 5,891,996; 6,506,883; Mateo, et al. (1997) Immunotechnol. 3(1): 71-81); mAb-806 (Ludwig Institue for Cancer Research, Memorial Sloan-Kettering) (Jungbluth, et al. (2003) Proc. Natl. Acad. Sci. USA. 100(2): 639-44); KSB-102 (KS Biomedix); MR1-1 (IVAX, National Cancer Institute) (PCT Publication No. WO 01/62931A2); and SC 100 (Scancell) (PCT Publication No. WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFalpha antibody developed by Centocor, adalimumab (Humira®), an anti-TNFalpha antibody developed by Abbott, Humicade®, an anti-TNFalpha antibody developed by Celltech, golimumab (CNTO-148), a fully human TNF antibody developed by Centocor, etanercept (Enbrel®), an p75 TNF receptor Fc fusion developed by Immunex/Amgen, lenercept, an p55TNF receptor Fc fusion previously developed by Roche, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β antibody being developed by Cambridge Antibody Technology, ABT 874 (J695), an anti-IL-12 p40 antibody being developed by Abbott, CAT-192, an anti-TGFβ1 antibody being developed by Cambridge Antibody Technology and Genzyme, CAT-213, an anti-Eotaxin1 antibody being developed by Cambridge Antibody Technology, LymphoStat-B® an anti-Blys antibody being developed by Cambridge Antibody Technology and Human Genome Sciences Inc., TRAIL-R1 mAb, an anti-TRAIL-R1 antibody being developed by Cambridge Antibody Technology and Human Genome Sciences, Inc., Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair® (Omalizumab), an anti-IgE antibody being developed by Genentech, Raptiva® (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD 23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (labetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-1), and anti-Her2 antibody being developed by Medarex and Immuno-Designed Molecules, HuMax®-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF®, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-Beta2 integrin antibody being developed by Xoma. In another embodiment, the therapeutics include KRN330 (Kirin); huA33 antibody (A33, Ludwig Institute for Cancer Research); CNTO 95 (alpha V integrins, Centocor); MEDI-522 (alpha Vβ3integrin, Medimmune); volociximab (alpha Vβ1 integrin, Biogen/PDL); Human mAb 216 (B cell glycosolated epitope, NCI); BiTE MT103 (bispecific CD19×CD3, Medimmune); 4G7×H22 (Bispecific Bcell×FcgammaR1, Medarex/Merck KGa); rM28 (Bispecific CD28×MAPG, EP Patent No. EP1444268); MDX447 (EMD 82633) (Bispecific CD64× EGFR, Medarex); Catumaxomab (removab) (Bispecific EpCAM×anti-CD3, Trion/Fres); Ertumaxomab (bispecific HER2/CD3, Fresenius Biotech); oregovomab (OvaRex®) (CA-125, ViRexx); Rencarex® (WX G250) (carbonic anhydrase IX, Wilex); CNTO 888 (CCL2, Centocor); TRC105 (CD105 (endoglin), Tracon); BMS-663513 (CD137 agonist, Brystol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NCl); MDX-060 (CD30, Medarex); MDX-1401 (CD30, Medarex); SGN-30 (CD30, Seattle Genentics); SGN-33 (Lintuzumab) (CD33, Seattle Genentics); Zanolimumab (HuMax-CD4) (CD4, Genmab); HCD122 (CD40, Novartis); SGN-40 (CD40, Seattle Genentics); Campath1h (Alemtuzumab) (CD52, Genzyme); MDX-1411 (CD70, Medarex); hLL1 (EPB-1) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Brystol Myers Squibb); Tremelimumab (Ticilimumab, CP-675,2) (CTLA4, Pfizer); HGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeutics); adecatumumab (MT201) (Epcam, Merck); edrecolomab (Panorex, 17-1A) (Epcam, Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (HERCEPTIN®) (HER2, Celldex); Pertuzumab (rhuMAb 2C4) (HER2 (DI), Genentech); apolizumab (HLA-DR beta chain, PDL Pharma); AMG-479 (IGF-1R, Amgen); anti-IGF-1R R1507 (IGF1-R, Roche); CP 751871 (IGF1-R, Pfizer); IMC-A12 (IGF1-R, Imclone); BIIB022 (IGF-1R, Biogen); Mik-beta-1 (IL-2Rb (CD122), Hoffman LaRoche); CNTO 328 (IL6, Centocor); Anti-KIR (1-7F9) (Killer cell Ig-like Receptor (KIR), Novo); Hu3S193 (Lewis (y), Wyeth, Ludwig Institute of Cancer Research); hCBE-11 (LTβR, Biogen); HuHMFG1 (MUC1, Antisoma/NC1); RAV12 (N-linked carbohydrate epitope, Raven); CAL (parathyroid hormone-related protein (PTH-rP), University of California); CT-011 (PD1, CureTech); MDX-1106 (ono-4538) (PD1, Medarex/Ono); MAb CT-011 (PD1, Curetech); IMC-3G3 (PDGFRa, Imclone); bavituximab (phosphatidylserine, Peregrine); huJ591 (PSMA, Cornell Research Foundation); muJ591 (PSMA, Cornell Research Foundation); GC1008 (TGFb (pan) inhibitor (IgG4), Genzyme); Infliximab (Remicade) (TNFa, Centocor); A27.15 (transferrin receptor, Salk Institute, INSERN WO 2005/111082); E2.3 (transferrin receptor, Salk Institute); Bevacizumab (AVASTIN®) (VEGF, Genentech); HuMV833 (VEGF, Tsukuba Research Lab, PCT Publication No. WO/2000/034337, University of Texas); IMC-18F1 (VEGFR1, Imclone); IMC-1121 (VEGFR2, Imclone).

Examples of useful bispecific parent antibodies include, but are not limited to, those with one antibody directed against a tumor cell antigen and the other antibody directed against a cytotoxic trigger molecule such as anti-FcγRI/anti-CD 15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific antibodies with one antibody which binds specifically to a tumor antigen and another antibody which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; bispecific antibodies for converting enzyme activated prodrugs such as anti-CD30/anti-alkaline phosphatase (which catalyzes conversion of mitomycin phosphate prodrug to mitomycin alcohol); bispecific antibodies which can be used as fibrinolytic agents such as anti-fibrin/anti-tissue plasminogen activator (tPA), anti-fibrin/anti-urokinase-type plasminogen activator (uPA); bispecific antibodies for targeting immune complexes to cell surface receptors such as anti-low density lipoprotein (LDL)/anti-Fc receptor (e.g. FcγRI, FcγRII or FcγRIII); bispecific antibodies for use in therapy of infectious diseases such as anti-CD3/anti-herpes simplex virus (HSV), anti-T-cell receptor: CD3 complex/anti-influenza, anti-FcγR/anti-HIV; bispecific antibodies for tumor detection in vitro or in vivo such as anti-CEA/anti-EOTUBE, anti-CEA/anti-DPTA, anti-anti-p185$^{HER2}$/anti-hapten; bispecific antibodies as vaccine adjuvants (see Fanger, M W et al., Crit Rev Immunol. 1992; 12(34):101-24, which is incorporated by reference herein); and bispecific antibodies as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan, O et R. O'Kennedy, Biochim Biophys Acta. 1990 Aug. 1; 1040 (1):1-11, which is incorporated by reference herein). Examples of trispecific antibodies include anti-CD3/anti-CD4/anti-CD37, anti-CD3/anti-CD5/anti-CD37 and anti-CD3/anti-CD8/anti-CD37.

In certain embodiments, the antibody comprising one or more non-natural amino acid residues at site-specific positions has high sequence identity to any parent antibody described herein. In certain embodiments, the antibody is substantially identical to a parent antibody described herein. In certain embodiments, the antibody has about 60% identity, about 65%, about 70%, about 75%, about 80%, about 85%, about 90%, or about 95% identity to a parent antibody described herein. In certain embodiments, the antibody has greater than about 65%, greater than about 70%, greater than about 75%, greater than about 80%, greater than about 85%, greater than about 90%, or greater than about 95% identity to a parent antibody described herein. Antibodies are substantially identical if at least one polypeptide chain of one antibody has sequence identity to a corresponding polypeptide chain of another antibody. In certain embodiments, the antibody comprising one or more non-natural amino acid residues at site-specific positions has at least one polypeptide chain having greater than about 65%, greater than about 70%, greater than about 75%, greater than about 80%, greater than about 85%, greater than about 90%, or greater than about 95% identity to any of SEQ ID NOS: 1-6 over at least one domain, at least two domains or at least three domains.

Antibody Compositions

Antibodies described herein can be formulated into compositions using methods available in the art and those disclosed herein. Any of the compounds disclosed herein can be provided in the appropriate pharmaceutical composition and be administered by a suitable route of administration.

In certain embodiments, the antibody compositions provided herein further comprise a pharmaceutically acceptable carrier. The carrier can be a diluent, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in E. W. Martin, 1990, Remington's Pharmaceutical Sciences, Mack Publishing Co.

In some embodiments, the pharmaceutical composition is provided in a form suitable for administration to a human subject. In some embodiments, the pharmaceutical composition will contain a prophylactically or therapeutically effective amount of the antibody together with a suitable amount of carrier so as to provide the form for proper administration to the patient. The formulation should suit the mode of administration.

In some embodiments, the pharmaceutical composition is provided in a form suitable for intravenous administration. Typically, compositions suitable for intravenous administration are solutions in sterile isotonic aqueous buffer. Where necessary, the composition may also include a solubilizing agent and a local anesthetic such as lignocaine to ease pain at the site of the injection. Such compositions, however, may be administered by a route other than intravenous administration.

In particular embodiments, the pharmaceutical composition is suitable for subcutaneous administration. In particular embodiments, the pharmaceutical composition is suitable for intramuscular administration.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, antibodies are supplied as a water free concentrate. In some embodiments, the antibody is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

In another embodiment, the pharmaceutical composition is supplied in liquid form. In some embodiments, the pharmaceutical composition is provided in liquid form and is substantially free of surfactants and/or inorganic salts. In some embodiments, the antibody is supplied as in liquid form at a unit dosage of at least 0.1 mg/ml, at least 0.5 mg/ml, at least 1 mg/ml, at least 2.5 mg/ml, at least 3 mg/ml, at least 5 mg/ml, at least 8 mg/ml, at least 10 mg/ml, at least 15 mg/ml, at least 25 mg/ml, at least 30 mg/ml, or at least 60 mg/ml.

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In therapeutic use, the practitioner will determine the posology most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

Methods of Use for Therapy or Prophylaxis

Certain antibodies provided herein can be used for the treatment or prevention of any disease or condition deemed suitable to the practitioner of skill in the art. Generally, a method of treatment or prevention encompasses the administration of a therapeutically or prophylactically effective amount of the antibody or antibody composition to a subject in need thereof to treat or prevent the disease or condition.

A therapeutically effective amount of the antibody or composition is an amount that is effective to reduce the severity, the duration and/or the symptoms of a particular disease or condition. The amount of the antibody or composition that will be therapeutically effective in the prevention, management, treatment and/or amelioration of a particular disease can be determined by standard clinical techniques. The precise amount of the antibody or composition to be administered with depend, in part, on the route of administration, the seriousness of the particular disease or condition, and should be decided according to the judgment of the practitioner and each subject's circumstances.

In some embodiments, the effective amount of the antibody provided herein is between about 0.025 mg/kg and about 1000 mg/kg body weight of a human subject. In certain embodiments, the antibody is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of antibody provided herein is between about 0.025 mg/kg and about 60 mg/kg body weight of a human subject. In some embodiments, the effective amount of an antibody of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

The pharmaceutical composition of the method can be administered using any method known to those skilled in the art. For example, the pharmaceutical composition can be administered intramuscularly, intradermally, intraperitoneally, intravenously, subcutaneously administration, or any combination thereof. In some embodiments, the pharmaceutical composition is administered subcutaneously. In some embodiments, the composition is administered intravenously. In some embodiments, the composition is administered intramuscularly.

Methods of Use for Detection or Diagnosis

The antibodies provided herein can be used for the detection of any target or for the diagnosis of any disease or condition deemed suitable to the practitioner of skill in the art. The methods encompass detecting the binding of an antibody to a target antigen in the appropriate location, e.g., the appropriate body, tissue, or cell. In the methods, the formation of a complex between the antibody and antigen can be detected by any method known to those of skill in the art. Examples include assays that use secondary reagents for detection, ELISA's and immunoprecipitation and agglutination assays. A detailed description of these assays is, for example, given in Harlow and Lane, Antibodies: A Laboratory Manual (Cold Spring Harbor Laboratory, New York 1988 555-612, WO96/13590 to Maertens and Stuyver, Zrein et al. (1998) and WO96/29605.

For in situ diagnosis, the antibody may be administered to a subject by methods known in the art such as, for example, intravenous, intranasal, intraperitoneal, intracerebral, intraarterial injection such that a specific binding between an antibody according to the invention with an eptitopic region on the amyloid protein may occur. The antibody/antigen complex may conveniently be detected through a label attached to the antibody or any other art-known method of detection.

Further provided herein are kits for detection or diagnosis. Exemplary kits comprise one or more antibodies provided herein along with one or more reagents useful for detecting a complex between the one or more antibodies and their target antigens.

Preparation of Antibodies

The antibodies described herein can be prepared by any technique apparent to those of skill in the art without limitation. Useful techniques for preparation include in vivo synthesis, for example with modified tRNA and tRNA synthetase, cell-free synthesis, for example with modified tRNA and tRNA synthetase, solid phase polypeptide synthesis and liquid phase polypeptide synthesis. Exemplary techniques are described in this section and in the examples below.

In certain methods, the antibody is translated and/or transcribed from one or more polynucleotides encoding the polypeptide chains of the antibody. Accordingly, provided herein are polynucleotides capable of encoding the antibodies having one or more non-natural amino acids at site-specific positions in one or more polypeptide chains. In certain embodiments, the polynucleotides comprise a codon not normally associated with an amino acid at the polynucleotide position corresponding to the site-specific polypeptide position for the non-natural amino acid. Examples of such codons include stop codons, 4 bp codons, 5 bp codons, and the like. The reaction mixture typically comprises a tRNA synthetase capable of making tRNAs that complement (suppress) said codon. These suppressor tRNAs are linked to the non-natural amino acids to facilitate their incorporation into the polypeptide at the site of the suppressor codon.

The antibodies can be prepared by techniques known to those of skill in the art for expressing such polynucleotides to incorporate non-natural amino acids into site specific positions of a polypeptide chain. Such techniques are described, for example, in U.S. Pat. Nos. 7,045,337 and 7,083,970, in U.S. Published Patent Application Nos. US 2008/0317670, US 2009/0093405, US 2010/0093082, US 2010/0098630, US 2008/0085277 and in international patent publication nos. WO 2004/016778 A1 and WO 2008/066583 A2, the contents of which are hereby incorporated by reference in their entireties.

In certain embodiments, an antibody can be prepared in a cell-free reaction mixture comprising at least one orthogonal tRNA aminoacylated with an unnatural amino acid, where the orthogonal tRNA base pairs with a codon that is not normally associated with an amino acid, e.g. a stop codon; a 4 bp codon, etc. The reaction mixture also comprises a tRNA synthetase capable of aminoacylating the orthogonal tRNA with an unnatural amino acid. Usually the orthogonal tRNA synthetase, which is susceptible to degradation by proteases present in bacterial cell extracts, is exogenously synthesized and added to the reaction mix prior to initiation of polypeptide synthesis. The orthogonal tRNA may be synthesized in the bacterial cells from which the cell extract is obtained, may be synthesized de novo during the polypeptide synthesis reaction, or may be exogenously added to the reaction mix.

In certain embodiments, components that affect unnatural amino acid insertion and protein insertion or folding are optionally added to the reaction mixture. Such components include elevated concentrations of translation factors to minimize the effect of release factor 1 and 2 and to further optimize orthogonal component concentrations. Protein chaperones (Dsb System of oxidoreductases and isomerases, GroES, GroEL, DNAJ, DNAK, Skp, etc.) may be exogenously added to the reaction mixture or may be overexpressed in the source cells used to prepare the cell extract The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose. The reactions may be of any volume, either in a small scale, usually at least about 1 μl and not more than about 15 μl, or in a scaled up reaction, where the reaction volume is at least about 15 μl, usually at least about 50 μl, more usually at least about 100 μl, and may be 500 μl, 1000 μl, or greater. In principle, reactions may be conducted at any scale as long as sufficient oxygen (or other electron acceptor) is supplied when needed.

Useful methods for synthesis where at least one unnatural amino acid is introduced into the polypeptide strand during elongation include but are not limited to: (I) addition of exogenous purified orthogonal synthetase, unnatural amino acid, and orthogonal tRNA to the cell-free reaction, (II) addition of exogenous purified orthogonal synthetase and unnatural amino acid to the reaction mixture, but with orthogonal tRNA transcribed during the cell-free reaction, (III) addition of exogenous purified orthogonal synthetase and unnatural amino acid to the reaction mixture, but with orthogonal tRNA synthesized by the cell extract source organism. In certain embodiments, the orthogonal components are driven by regulatable promoters, so that synthesis levels can be controlled although other measures may be used such as controlling the level of the relevant DNA templates by addition or specific digestion.

In some embodiments, a bacterial cell-free expression system is used to produce protein or peptide variants with non-native amino acids (nnAA). The use of bacterial cell-free extracts for in vitro protein synthesis offers several advantages over conventional in vivo protein expression methods. Cell-free systems can direct most, if not all, of the metabolic resources of the cell towards the exclusive production of one protein. Moreover, the lack of a cell wall and membrane components in vitro is advantageous since it allows for control of the synthesis environment. However, the efficiency of cell-free extracts can be decreased by bacterial proteins that inhibit protein synthesis, either directly or indirectly. Thus, inactivation of undesirable proteins that decrease the efficiency of protein synthesis should increase the yield of desirable proteins in cell-free extracts. For example, the inactivation of proteins that decrease the efficiency of protein synthesis should increase the yield of polypeptides having non-native amino acids incorporated at a defined amino acid residue. The introduction of nnAA into polypeptides is useful for increasing the biological diversity and function of proteins. One approach for producing polypeptides having a nnAA incorporated at a defined amino acid residue is to use an nnAA, aminoacylated orthogonal CUA containing tRNA for introduction of the nnAA into the nascent polypeptide at an amber (stop) codon during protein translation. However, the incorporation of nnAA at an amber codon can be inhibited by the native bacterial termination complex, which normally recognizes the stop codon and terminates translation. Release Factor 1 (RF1) is a termination complex protein that facilitates the termination of translation by recognizing the amber codon in an mRNA sequence. RF1 recognition of the amber stop codon can promote pre-mature truncation products at the site of non-native amino acid incorporation, and thus decreased protein yield. Therefore, attenuating the activity of RF1 may increase nnAA incorporation into recombinant proteins.

It has previously been shown that nnAA incorporation can be increased by attenuating RF1 activity in 3 ways: 1) neutralizing antibody inactivation of RF1, 2) genomic knockout of RF1 (in an RF2 bolstered strain), and 3) site specific removal of RF1 using a strain engineered to express RF1 containing a protein tag for removal by affinity chromatography (Chitin Binding Domain and His Tag). Another method for inactivating RF1 comprises introducing proteolytic cleavage sites into the RF1 amino acid sequence. The cleavage sites are not accessible to the protease during bacterial cell growth, but are cleaved by the protease when the bacterial cells are lysed to produce cell-free extract. Thus, the yield of full length polypeptides having a nnAA incorporated at an amber codon is increased in bacterial cell extracts expressing such modified RF1 variants.

In some embodiments, in order to produce antibodies comprising a non-natural amino acid, one needs a nucleic acid template. The templates for cell-free protein synthesis can be either mRNA or DNA. The template can comprise sequences for any particular antibody of interest, and may encode a full-length antibody or a fragment of any length thereof. Nucleic acids that serve as protein synthesis templates are optionally derived from a natural source or they can be synthetic or recombinant. For example, DNAs can be recombinant DNAs, e.g., plasmids, viruses or the like.

In some embodiments, once a nucleic acid template of an antibody is produced, the template is used to synthesize the antibody in a cell-free translation system. For example, the template can be added to a cell lysate under conditions sufficient to translate the template into protein. The cell lysate can be from bacterial cells or eukaryotic cells. The expressed protein can then be purified using methods known in the art, as described below.

In some embodiments, a translation system (e.g., an in vitro protein synthesis system) is used to produce the antibody with one or more nnAAs incorporated therein. An exemplary translation system comprises a cell free extract, cell lysate, or reconstituted translation system, along with the nucleic acid template for synthesis of the desired polypeptide or protein having non-native amino acids at preselected (defined) positions. The reaction mixture will further comprise monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. In addition to the above components such as a cell-free extract, nucleic acid template, and amino acids, materials specifically required for protein synthesis may be added to the reaction. The materials include salts, folinic acid, cyclic AMP, inhibitors for protein or nucleic acid degrading enzymes, inhibitors or regulators of protein synthesis, adjusters of oxidation/reduction potentials, non-denaturing surfactants, buffer components, spermine, spermidine, putrescine, etc. Various cell-free synthesis reaction systems are well known in the art. See, e.g., Kim, D. M. and Swartz, J. R. Biotechnol. Bioeng. 66:180-8 (1999); Kim, D. M. and Swartz, J. R. Biotechnol. Prog. 16:385-90 (2000); Kim, D. M. and Swartz, J. R. Biotechnol. Bioeng. 74:309-16 (2001); Swartz et al, Methods MoL Biol. 267:169-82 (2004); Kim, D. M. and Swartz, J. R. Biotechnol. Bioeng. 85:122-29 (2004); Jewett, M. C. and Swartz, J. R., Biotechnol. Bioeng. 86:19-26 (2004); Yin, G. and Swartz, J. R., Biotechnol. Bioeng. 86:188-95 (2004); Jewett, M. C. and Swartz, J. R., Biotechnol. Bioeng. 87:465-72 (2004); Voloshin, A. M. and Swartz, J. R., Biotechnol. Bioeng. 91:516-21 (2005). Additional conditions for the cell-free synthesis of desired polypeptides are described in WO2010/081110, the contents of which are incorporated by reference herein in its entirety.

In some embodiments, a DNA template is used to drive in vitro protein synthesis, and RNA polymerase is added to the reaction mixture to provide enhanced transcription of the DNA template. RNA polymerases suitable for use herein include any RNA polymerase that functions in the bacteria from which the bacterial extract is derived. In other embodiments, an RNA template is used to drive in vitro protein synthesis, and the components of the reaction mixture can be admixed together in any convenient order, but are preferably admixed in an order wherein the RNA template is added last, thereby minimizing potential degradation of the RNA template by nucleases.

In some embodiments, a cell-free translation system is used to produce the antibody with one or more nnAAs incorporated therein. Cell-free protein synthesis exploits the catalytic power of the cellular machinery. Obtaining maximum protein yields in vitro requires adequate substrate supply, e.g. nucleoside triphosphates and amino acids, a homeostatic environment, catalyst stability, and the removal or avoidance of inhibitory byproducts. The optimization of in vitro synthetic reactions benefits from recreating the in vivo state of a rapidly growing organism. In some embodiments of the invention, cell-free synthesis is therefore performed in a reaction where oxidative phosphorylation is activated. Additional details are described in U.S. Pat. No. 7,338,789, the contents of which are incorporated by reference herein in its entirety.

In vitro, or cell-free, protein synthesis offers several advantages over conventional in vivo protein expression methods. Cell-free systems can direct most, if not all, of the metabolic resources of the cell towards the exclusive production of one protein. Moreover, the lack of a cell wall and membrane components in vitro is advantageous since it allows for control of the synthesis environment. For example, tRNA levels can be changed to reflect the codon usage of genes being expressed. The redox potential, pH, or ionic strength can also be altered with greater flexibility than with in vivo protein synthesis because concerns of cell growth or viability do not exist. Furthermore, direct recovery of purified, properly folded protein products can be easily achieved. In some embodiments, the productivity of cell-free systems has improved over 2-orders of magnitude in recent years, from about 5 µg/ml-hr to about 500 µg/ml-hr.

In certain embodiments, tRNA synthetase is exogenously synthesized and added to the cell-free reaction mix. In certain embodiments, the reaction mix is prepared from bacterial cells in which ompT has been inactivated or is naturally inactive. OmpT is believed to degrade components of the reaction mixture including tRNA synthetase.

In addition to the above components such as cell-free extract, genetic template, and amino acids, materials specifically required for protein synthesis may be added to the reaction. These materials include salts, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. of acetic acid or glutamic acid). One or more of such salts may have an alternative amino acid as a counter anion. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously adjusted in accordance with the change in those of other components. Also, the concentration levels of components in the reactor may be varied over time. The adjuster of oxidation/reduction potential may be dithiothreitol, ascorbic acid, glutathione and/or their oxidized forms.

In certain embodiments, the reaction can proceed in a dialysis mode, in a diafiltration batch mode, in a fed-batch mode of in a semi-continuous operation mode. In certain embodiments, a feed solution can be supplied to the reactor through a membrane or through an injection unit. Synthesized antibody can accumulate in the reactor followed by isolation or purification after completion of the system operation. Vesicles containing the antibody may also be continuously isolated, for example by affinity adsorption from the reaction mixture either in situ or in a circulation loop as the reaction fluid is pumped past the adsorption matrix.

During protein synthesis in the reactor, the protein isolating means for selectively isolating the desired protein may include a unit packed with particles coated with antibody molecules or other molecules for adsorbing the synthesized, desired protein. Preferably, the protein isolating means comprises two columns for alternating use.

The resulting antibody can be purified or isolated by standard techniques. Exemplary techniques are provided in the examples below.

Assay Methods

Antibodies can be assayed for their expected activity, or for a new activity, according to any assay apparent to those of skill in the art. The resulting antibody can be assayed activity in a functional assay or by quantitating the amount of protein present in a non-functional assay, e.g. immunostaining, ELISA, quantitation on Coomasie or silver stained gel, etc., and determining the ratio of biologically active protein to total protein.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

EXAMPLES

As used herein, the symbols and conventions used in these processes, schemes and examples, regardless of whether a particular abbreviation is specifically defined, are consistent with those used in the contemporary scientific literature, for example, the Journal of Biological Chemistry.

For all of the following examples, standard work-up and purification methods known to those skilled in the art can be utilized. Unless otherwise indicated, all temperatures are expressed in ° C. (degrees Centigrade). All methods are conducted at room temperature unless otherwise noted.

Example 1

Synthesis of Exemplary Antibodies Containing Non-Natural Amino Acids and Conjugation to an Exemplary Cytotoxic Agent The following example describes exemplary antibodies containing non-natural amino acids at defined positions along with methods of their construction and expression. The antibodies were assessed for expression, suppression efficiency, efficiency of conjugation with a cell-killing agent, cell binding, and cell killing, as set forth below. In this example, the exemplary antibodies are based on parent antibody trastuzumab (U.S. Pat. No. 6,165,464 and 2006/0018899 A1; Carter et al., 1992, *Proc. Natl. Acad. Sci.* USA 10:4285-4289).

First, constructs were made incorporating a TAG amber codon at a defined position in the heavy chain of trastuzumab. Site directed mutagenesis was performed using a pYD plasmid containing the coding region of trastuzumab with a C-terminal-(His)$_6$ tag (SD02005) as DNA template and synthetic oligonucleotides (Eurofins MWS Operon; Huntsville, Ala.) containing mutations of interest in both sense and antisense directions. Oligonucleotides of each mutation were added to the DNA template and PHUSION® polymerase (New England Biolabs; Ipswich, Mass.) to a final volume of 20 µL. The final concentration of each component was 0.16 µM of each oligonucleotide, 0.5 ng/µL template DNA, 0.02 U/µL PHUSION® polymerase in HF buffer containing 1.5 mM MgCl$_2$ and 200 µM dNTP. Mixture was incubated at 98° C. 5 m, 18 PCR cycles (98° C. 30 s, 55° C. 1 min, 72° C. 4 min), 10 min at 72° C. and stored at 4° C. DpnI (New England Biolabs; Ipswich, Mass.) was added to the mixture to final concentration of 0.6 U/µL and incubated for 37° C. 1 h to digest parent DNA.

5 µL of each mixture was then transformed into 50 µL of chemically competent *E. coli* cells with a MultiShot™ 96-Well Plate TOP10 according to the manufacturer's procedure (Invitrogen; Carlsbad, Calif.). Transformed cells were recovered in 200 µL SOC (Invitrogen; Carlsbad, Calif.) at 37° C. for 1 hr and plated onto Luria-Bertani (LB) agar supplemented with 50 µg/mL kanamycin (Teknova; Hollister, Calif.). After 24 hrs at 37° C., colonies were picked into 200 µL LB with 7.5% glycerol and 50 µg/mL kanamycin, and grown at 37° C. for 24 hrs. 20 µL of culture was used for rolling circle amplification (RCA) and sequenced by primer extension using T7 (5'TAATACGACTCACTATAGG 3' (SEQ ID NO: 7)) and T7 term (5'GCTAGTTATTGCTCA-GCG3' (SEQ ID NO: 8)) primers. Sequence was analyzed using SEQUENCHER® software (Gene Codes Corp; Ann Arbor, Mich.), and clones containing mutations were picked and arrayed into 96 well plates. Overnight cultures of selected variants were grown and used for preparing plasmid DNA using the standard 96 well mini-prep protocol according to the manufacturer (Qiagen; Germantown, Md.). Concentration of mini-prepped DNA was measured using absorbance at 260 nm (and 280 nm).

The variants were then expressed in a cell-free protein synthesis reaction as follows as described in Zawada et al., 2011, *Biotechnol. Bioeng.* 108(7)1570-1578 with the modifications described below. Unsubstituted trastuzumab was also made as a control. Cell-free extracts were treated with 50 µM iodoacetamide for 30 min at RT (20° C.) and added to a premix containing all other components except for heavy chain DNA from variants of interest. Cell free reactions were initiated by addition of plasmid DNA of heavy chain DNA variants and incubated at 30° C. for 12 h on a shaker at 450 rpm in 96 deep well plates. The reaction was incubated further at 4° C. for 5 h. The final concentration in the protein synthesis reaction was 30% cell extract, 1 mM para-azido phenylalanine (pAzF) (RSP Amino Acids), 0.125 mg/mL *M jannaschii* amber suppressor tRNA, 0.37 mg/mL *M jannaschii* pAzF-specific amino-acyl tRNA synthetase (FRS), 2 mM GSSG, 0.29 mg/mL PDI (Mclab), 100 µg/mL *E. coli* DsbC, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for Tyrosine and Phenylalanine), 4 mM sodium oxalate, 1 mM putrescine, 1.5 mM spermidine, 15 mM potassium phosphate, 100 nM T7 RNAP, 2 µg/mL trastuzumab light chain DNA, 8 µg/mL trastuzumab-(His)6 heavy chain DNA. Each trastuzamab variant was produced in 1 mL scale in 96 deep well plates in duplicates. A total of three plates were used to express the variants, each compared to expression of an unsubstituted trastuzumab to normalize for expression across the plates. It should be noted that all trastuzumab variants thus produced were aglycosylated.

To monitor protein synthesis, a portion of each cell-free protein synthesis reaction was removed and spiked with 3.33% (v/v) l-[U-14C]-leucine (300 mCi/mmole; GE Life Sciences, Piscataway, N.J.). The suppression of amber codon at different sites of the heavy chain was determined by [$^{14}$C]-autoradiograhy of reducing SDS-PAGE gels. Full length trastuzumab heavy chain and suppressed tastuzumab heavy chain variants run at 50 kD on SDS-PAGE. Non suppressed (truncated) trastuzumab variants run at a lower molecular weight. Amber suppression in the heavy chain is determined by:

$$supression = \frac{\text{band intensity of suppressed heavy chain } TAG \text{ variant}}{\text{band intensity of wild type heavy chain}}$$

Band intensity was determined by ImageQuant (Amersham Biosciences Corp.; Piscataway, N.J.). It should be noted that this 14C gel assay cannot be used to assess suppressions for TAG variants of heavy chain from the position of 425 (EU index numbering) to C terminus since the truncated variants cannot be distinguished from the full length product.

Following synthesis, each 1 mL reaction was diluted with 1 mL PBS at pH7.4. The mixture was centrifuged at 5000×g 4° C. for 15 min. Supernatant was captured with IMAC Phytip containing 40 µL resin (PhyNexus, Inc.; San Jose, Calif.) by pipetting up and down 4 times slowly at a flow rate of 4.2 µl/min. Resin was washed with 925 µL IMAC binding buffer (50 mM Tris pH 8.0, 300 mM NaCl, 10 mM imidazole) by pipetting up and down twice at a flow rate of 8.3 µL/min. This process was repeated once with an additional 925 µL IMAC binding buffer. Bound protein was eluted with 250 µL IMAC elution buffer (50 mM Tris pH 8.0, 300 mM NaCl, 500 mM Imidazole) by pipetting up and down 4 times at a flow rate of 4.2 µL/min. As the (his)6 tag of the construct is C-terminal, this procedure allows isolation of full length protein. To quantitate the variants following purification, IMAC purified samples were mixed with 2× gel loading buffer (Bio-Rad#161-0737) resolved by of 4-15% Stain-Free™ gel (Bio-Rad Criterion™ TGX #567-8085). Samples were not heated before loading into wells of the gel. Protein bands were visualized and quantitated by Bio-Rad Gel Doc EZ System using Image Lab software (v3). Band intensities of samples were determined based on mass standards of HERCEPTIN® loaded on the same gel.

Next, the trastuzumab variants were conjugated to an exemplary cytotoxic agent, MMAF, using a constrained cyclooctyne reagent. In brief, DBCO-MMAF (structure shown as FIG. 1; ACME Bioscience; Palo Alto, Calif.) was dissolved in DMSO to a final concentration of 5 mM. The compound was diluted into with PBS to 1 mM and then added to trastuzumab-(His)$_6$ variants in IMAC elution buffer to final drug concentration of 100 µM. Mixture was incubated at RT (20° C.) for 17 hours. Reaction was stopped by adding Sodium Azide to final concentration of 100 mM and buffer exchanged using Zeba plates (Thermo Scientific; Waltham, Mass.) equilibrated in 1×PBS. Filtrate was then passed through a MUSTANG® Q plate (Pall Corp.; Port Washington, N.Y.) to remove endotoxin.

Example 2

Characterization of Exemplary Antibody-Drug Conjugates

Hydrophobic Interaction Chromatography (HIC) was performed to quantitate the samples and to determine the drug-antibody ratios of the trastuzumab variant drug conjugates as follows. Samples and standards were diluted 1:2 in 3M Ammonium Sulfate (EMD Chemical), 50 mM Sodium Phosphate pH 7.0 (Mallinckrodt) prepared in MilliQ water. An Agilent 1100 binary pump HPLC system was equipped with a Tosoh Bioscience LLC TSK-gel Butyl-NPR® (4.6 mm×3.5 cm) column with a column compartment temperature of 30° C. The mobile phase A was 1.5M Ammonium Sulfate, 50 mM Sodium Phosphate, pH 7.0. The mobile phase B was 50 mM Sodium Phosphate, pH 7.0 in 80:20 water:Isopropyl Alcohol (Honeywell). The mobile phase was delivered at a flow rate of 1.0 mL/minute. The separation was performed with a linear gradient of 15% mobile phase B to 100% mobile phase B in 10 minutes. The UV data was acquired at both 210 and 280 nm. The peak areas were quantitated using Chemstation software (Agilent) and the Drug Antibody Ratio (DAR) was calculated from the percent of the total peak area.

To assess binding of the conjugated trastuzumab variants, a binding assay to cells expressing HER2 was performed as follows. The binding of the purified conjugated variants to HER2 on SKBR3 cells, which overexpress the HER2/c-erb-2 gene product, with over 1.5 million receptor copies per cell (ATCC # HTB-30, Manassas, Va.) was compared to clinical grade Herceptin®, unglycosylated trastuzumab produced by cell-free protein synthesis, or human serum IgG1 as a negative control (Sigma-Aldrich; St. Louis, Mo.). SKBR3 cells were cultured in DMEM:Ham's F-12 (50:50), high glucose (Cellgro-Mediatech; Manassas, Va.) supplemented with 10% heat-inactivated fetal bovine serum (Hyclone; Thermo Scientific; Waltham, Mass.), 2 mM glutamax (Invitrogen; Carlsbad, Calif.) and 1× Penicillin/streptomycin (Cellgro-Mediatech; Manassas, Va.). Adherent cells were washed twice with calcium and magnesium-free Hanks Balanced Salt Solution (HBSS), harvested with HYQ®TASE™ (Hyclone; Thermo Scientific; Waltham, Mass.). A total of 200,000 cells per sample in total volume of 10 µL were incubated with serial dilutions of either conjugated trastuzumab variant, clinical grade HERCEPTIN®, or aglycosylated trastuzumab made in 10 µL FACS buffer (DPBS buffer supplemented with 1% bovine serum albumin). Cells plus antibody or ADC were incubated for 60 minutes on ice. Unstained cells, human IgG1 (Isotype control) and Secondary antibody (goat anti-human IgG) were used as controls. Cells were washed twice with ice-cold FACS buffer and incubated with either 5 µg/ml Alexa 647 labeled goat anti-human IgG secondary antibody (Invitrogen; Carlsbad, Calif.) on ice for 1 hour. All samples were washed using FACS buffer and analyzed using a BD FACS Calibur system (BD Biosciences; San Jose, Calif.).

Mean fluorescence intensities were fitted using non-linear regression analysis with one site specific binding equation using GraphPad Prism (GraphPad v 5.00, Software; San Diego, Calif.). Data was expressed as Relative MFI vs. concentration of antibody or antibody variant in µg/ml.

Next, the effects of the conjugated trastuzumab on cell killing were measured with a cell proliferation assay as follows. SKBR3 and MDA-MB-468 were obtained from ATCC and maintained in DMEM:Ham's F-12 (50:50), high glucose (Cellgro-Mediatech; Manassas, Va.) supplemented with 10% heat-inactivated fetal bovine serum (Hyclone; Thermo Scientific; Waltham, Mass.), 2 mM glutamax (Invitrogen; Carlsbad, Calif.) and 1× Penicillin/streptomycin (Cellgro-Mediatech; Manassas, Va.). Adherent cells were washed twice with calcium and magnesium-free Hanks Balanced Salt Solution (HBSS), harvested with HYQ®TASE™ (Hyclone; Thermo Scientific; Waltham, Mass.). A total of $10^3$ cells were seeded in a volume of 40 µl in a 96-well half area flat bottom white Polystyrene plate. The cells were allowed to adhere overnight at 37° C. in a $CO_2$ incubator. ADC variants were formulated at 2× concentration in DMEM/F12 medium and filtered through MultiScreen$_{HTS}$ 96-Well Filter Plates (Millipore; Billerica, Mass.). Filter sterilized conjugated trastuzumab variants, HERCEPTIN®, or aglycoslyated trastuzumab were added into treatment wells and plates were cultured at 37° C. in a CO2 incubator for 120 hrs. For cell viability measurement, 80 µl of Cell Titer-Glo® reagent (Promega Corp.; Madison, Wis.) was added into each well, and plates processed as per product instructions. Relative luminescence was measured on an ENVISION® plate reader (Perkin-Elmer; Waltham, Mass.). Relative luminescence readings were converted to % viability using untreated cells as controls. Data was fitted with non-linear regression analysis, using log(inhibitor) vs. response—Variable slope, 4 parameter fit equation using GraphPad Prism (GraphPad v 5.00, Software; San Diego, Calif.). Data was expressed as relative cell viability, ATP content % vs. dose of ADC in µg/ml.

Positive results of these characterization experiments are presented in Tables 1, 2, and 3 (plates 1, 2, and 3, respectively). In the Tables, the following properties of the variants are shown: the rank order and concentration of protein made, the efficiency of expression of full length product compared to wild-type (suppression efficiency), ability to bind HER2-expressing cells, drug-antibody ratio (expressed as the number of cytotoxic agents per antibody), a comment regarding the HIC profile, and the observed $IC_{50}$ from the cell-killing assay described above. In the comments regarding the HIC assay, Single Peak corresponds to a profile that resolved well as a single peak (an example of such a profile is shown as FIG. 2), NWR corresponds to a poorly resolved profile (an example of such a profile is shown as FIG. 3), and WR corresponds to a well-resolved HIC profile (an example of such a profile is shown as FIG. 4). Several of the variants that exhibited a single peak profile also exhibited potent killing, which indicates that the variant was indeed conjugated with drug, but failed to resolve on the HIC column.

In general, preferred variants exhibit an $IC_{50}$ of about 20 ng/ml or below, even more preferably below about 10 ng/ml, and even more preferably below about 5 ng/ml. Preferably, the variants are in the top 50% of expression, and even more preferably, are in the top 25% of expression. Variants that have a DAR of at least about 1.0 are also preferred. Preferred variants include those with a non-natural amino acid replacing positions V005, A023, G042, G065, S074, A084, A118, S119, S132, S134, T135, S136, G137, G138, T139, T155, S160, A162, S165, A172, L174, S176, S177, S191, G194, S219, P238, S239, F241, F243, K246, E356, M358, K360, V262, V264, D265, S267, H268, E269, D270, P271, E272, K274, F275, Y278, D280, G281, V282, E283, N286, T289, R292, E293, E294, Q295, Y296, N297, S298, T299, Y300, R301, V303, V305, K317, K320, S324, K326, A327, P329, A330, I332, E333, K334, T335, S337, A339, R344, R355, T359, L398, S375, S383, N384, Q386, N389, K392, G420, K340, Q342, F404, Q438, N421, and Y436. Even more preferred were variants including those with a non-natural amino acid replacing positions V005, A023, S074, A084, A118, S119, S132, S134, T135, S136, G137, T139, S160, A162, S165, A172, S191, G194, S239, F241, K246, S267, H268, E269, D270, P271, E272, K274, F275, D280, G281, V282, E283, N286, T289, R292, E293, E294, Q295, Y296, N297, S298, T299, Y300, R301, V303, V305, K317, K320, S324, K326, A327, P329, A330, I332, E333, K334, T335, S337, A339, R344, R355, T359, L398, S375, Q386, N389, K392, G420, K340, Q342, Q438, and N421. Still more preferred were variants including those with a non-natural amino acid replacing positions V005, A023, A084, A118, S119, S132, S134, S136, G137, S160, A162, A172, S239, F241, S267, E269, D270, P271, E272, V282, N286, R292, E293, Y296, S298, P329, A330, K334, T335, K340, R355, T359, Q386, N389, F404, G420, N421, Q438, and Q342. Variants with a non-natural amino acid replacing positions V005, A084, A118, S132, S136, S239, E293, K334, R355, Q342, T359, and N389 were identified as particularly preferred.

It was also noted that the expression, suppression efficiency, conjugation efficiency, cell-binding, and cell killing were not predictable based on the published crystal structure of Fc. For example, E293 and K334 would not be predicted to accept substitution with an aromatic phenylalanine derivative based on their positions within the Fc structure, yet both express well and are potent killers, with $IC_{50}$ values of 2.7 and 3.0 ng/ml, respectively. Conversely, S131 was predicted to be an excellent position for conjugation based on its availability on the surface of the heavy chain, yet derivatives with substitutions in this position were poor conjugators (DAR of 0.65) and poor killers ($IC_{50}$ of 27.1 ng/mL). Thus, it was concluded that experimentation was required to identify optimal sites for expression, suppression, conjugation, and cell killing.

It should also be noted that sites near the N-linked glycosylation site of trastuzumab, N297, were found to be well-suited for conjugation. In particular, sites from R292 through R301, V303 and V305 were found to exhibit desirable cell-killing and/or conjugation properties. It was possible to assess these sites because of the aglycosylated form of the trastuzumab variants produced in the cell-free protein synthesis reaction as described above.

TABLE 1

| Variant | IMAC gel µg/mL | $^{14}C$ expression rank order | CFPS $^{14}C$ µg/mL | Suppression efficiency | Cell Binding | DAR | HIC Profile | $IC_{50}$ SKBR3 cell killing (ng/ml) |
|---|---|---|---|---|---|---|---|---|
| S136 | 151 |   | 77  | 35% | + | 1.54 | WR | 7.9 |
| S239 | 161 | 2 | 126 | 57% | + | ND | Single Peak | 5.2 |
| A118 | 156 | 7 | 105 | 48% | + | 1.51 | WR | 6.5 |
| K246 | 162 | 18 | 75  | 34% | + | ND | Single Peak | 6.6 |
| S119 | 191 | 6 | 109 | 50% | + | 1.41 |    | 7.4 |
| S132 | 307 | 1 | 158 | 72% | + | 1.58 | WR | 8 |
| A162 | 145 | 17 | 77 | 35% | + | 1.38 | NWR | 8 |
| V005 | 186 | 3 | 124 | 56% | + | 0.99 | NWR | 11.5 |
| S191 | 183 | 4 | 114 | 52% | + | 0.68 | WR | 13.9 |
| S074 | 177 | 9 | 96  | 44% | + | 0.78 | NWR | 9.9 |
| T135 | 151 | 8 | 96  | 44% | + | 1.03 | NWR | 10.1 |
| A084 | 150 | 5 | 114 | 52% | + | 1.28 | WR | 9 |
| G194 | 145 | 11 | 89 | 40% | + | 1.1 | WR | 10.8 |
| T139 | 138 | 24 | 55 | 25% | + | 1 | WR | 9.6 |
| A172 | 130 | 21 | 64 | 29% | + | 1.3 | NWR | 12.5 |
| S134 | 124 | 16 | 80 | 36% | + | 1.37 | WR | 8.9 |
| G137 | 112 | 15 | 83 | 38% | + | 1.23 | WR | 9.3 |

TABLE 1-continued

| Variant | IMAC gel µg/mL | $^{14}C$ expression rank order | CFPS $^{14}C$ µg/mL | Suppression efficiency | Cell Binding | DAR | HIC Profile | $IC_{50}$ SKBR3 cell killing (ng/ml) |
|---|---|---|---|---|---|---|---|---|
| A023 | 110 | 19 | 70 | 32% | + | 1.33 | NWR | 9.8 |
| S165 | 103 | 20 | 68 | 31% | + | 1.04 | NWR | 9.5 |
| F241 | 99 | 13 | 87 | 39% | + | ND | Single Peak | 8.4 |
| S160 | 96 | 14 | 86 | 39% | + | 1.34 | WR | 10 |
| P238 | 93 | 22 | 60 | 27% | + | 0.47 | NWR | 12.9 |
| T155 | 89 | 10 | 95 | 43% | + | 1.19 | WR | 10.5 |
| V264 | 88 | 32 | 29 | 13% | + | ND | Single Peak | 10.5 |
| S176 | 74 | 31 | 38 | 17% | + | 0.82 | NWR | 12.4 |
| G138 | 72 | 29 | 43 | 20% | + | 1.16 | WR | 11.2 |
| G065 | 68 | 30 | 40 | 18% | + | ND | NWR | 9.6 |
| G042 | 68 | 26 | 49 | 22% | + | 1.12 | NWR | 13.8 |
| F243 | 67 | 22 | 60 | 27% | + | 0.12 | NWR | 10.4 |
| V262 | 47 | 36 | 18 | 8% | shifted rt | ND | NWR | 8.2 |
| D265 | 56 | 38 | 13 | 6% | + | ND | Single Peak | 9 |
| L174 | 52 | 28 | 43 | 20% | + | 1.07 | NWR | 12.8 |
| S219 | 26 | 27 | 45 | 20% | + | 1.18 | NWR | 13.6 |
| S131 | 76 | 25 | 49 | 22% |  | 0.65 |  | 27.1 |
| G161 | 43 | 33 | 26 | 12% |  | 0.97 | NWR | 87.7 |
| T164 | 17 | 35 | 22 | 10% |  | 0.68 | NWR | 17.5 |
| T195 | 26 | 39 | 14 | 6% |  | 1.1 | NWR |  |
| S177 | 23 | 34 | 24 | 11% | + | 0.68 | NWR | 13.6 |

TABLE 2

| Variant | IMAC Gel (ug/ml) | $^{14}C$ expression rank order | CFPS $^{14}C$ µg/mL | Suppression Efficiency | Binding | DAR | HIC Profile | $IC_{50}$ Cell Killing (ng/ml) |
|---|---|---|---|---|---|---|---|---|
| E293 | 147.6 | 9 | 50.7 | 19% | + | 1.5 | WR | 2.7 |
| K334 | 135.7 | 3 | 72.5 | 28% | + | 0.12 | Single Peak | 3 |
| E269 | 91.2 | 24 | 25.3 | 10% | + | 1.21 | WR | 1.4 |
| S298 | 76.9 | 34 | 10.6 | 4% | + | 1.17 | NWR | 1.9 |
| R292 | 160.9 | 7 | 54.8 | 21% | + | ND | Single Peak with sh | 2.4 |
| E272 | 111.2 | 19 | 32.2 | 12% | + | 1.05 | WR | 3 |
| V282 | 117.4 | 15 | 39.7 | 15% | + | 0.62 | NWR | 3.1 |
| Y296 | 142.7 | 14 | 39.9 | 15% | + | ND | Single Peak | 3.5 |
| D270 | 122.6 | 12 | 43.8 | 17% | + | ND | Single Peak | 3.9 |
| N286 | 89.8 | 20 | 31.1 | 12% | + | 0.71 | NWR | 4 |
| E333 | 96.1 | 8 | 52.6 | 20% | + | 0.55 | NWR | 5 |
| S324 | 88.5 | 5 | 59.7 | 23% | + | 0.3 | NWR | 5.8 |
| H268 | 140.2 | 4 | 67.6 | 26% | + | 0.46 | NWR | 7.9 |
| T289 | 128.2 | 11 | 44 | 17% | + | 0.26 | NWR | 8.2 |
| F275 | 97.3 | 13 | 42.4 | 16% | + | 0.24 | NWR | 9 |
| I332 | 98.1 | 6 | 54.9 | 21% | + | 0.88 | NWR | 10 |
| T335 | 123.7 | 2 | 82.4 | 32% | + | 0.33 | NWR | 11.2 |
| P329 | 61.4 | 16 | 36.9 | 14% | + | 1.05 | NWR | 3.6 |
| P271 | 78.2 | 18 | 32.3 | 12% | + | 1.05 | WR | 4.4 |
| A330 | 63.6 | 10 | 44.7 | 17% | + | 1.51 | NWR | 4.5 |
| Y300 | 124.0 | 27 | 17.4 | 7% | + | 0.13 | NWR | 4.8 |
| S267 | 22.1 | 29 | 12.4 | 5% | + | 1.57 | NWR | 5.1 |
| A327 | 38.0 | 22 | 26.3 | 10% | + | 0.69 | NWR | 5.2 |
| G281 | 31.0 | 32 | 11.5 | 4% | + | 0.27 | NWR | 5.2 |
| V305 | 42.8 | 35 | 10.2 | 4% | + | 0.06 | NWR | 5.5 |
| N297 | 34.0 | 37 | 7.8 | 3% | + | 0.09 | NWR | 6.5 |
| Q295 | 35.6 | 28 | 14.2 | 5% | + | ND | Single Peak | 6.8 |
| R301 | 41.8 | 39 | 6 | 2% | + | ND | Single Peak | 7.8 |
| E294 | 27.9 | 30 | 12 | 5% | + | 0.65 | NWR | 8.3 |
| E283 | 32.1 | 31 | 11.7 | 4% | + | 0.24 | NWR | 8.7 |
| D280 | 18.0 | 36 | 10.1 | 4% | + | ND | Single | 8.8 |

TABLE 2-continued

| Variant | IMAC Gel (ug/ml) | $^{14}C$ expression rank order | CFPS $^{14}C$ µg/mL | Suppression Efficiency | Binding | DAR | HIC Profile | $IC_{50}$ Cell Killing (ng/ml) |
|---|---|---|---|---|---|---|---|---|
| K326 | 35.0 | 25 | 24.1 | 9% | + | 0.54 | NWR | 9 |
| K317 | 38.0 | 33 | 11.4 | 4% | + | 0.22 | NWR | 9.5 |
| K274 | 36.3 | 26 | 19.3 | 7% | + | 0.45 | WR | 10.2 |
| T299 | 20.4 | 40 | 4.5 | 2% | + | ND | NWR | 10.3 |
| V303 | 93.6 | 21 | 29 | 11% | + | 0.01 | NWR | 11.1 |
| K320 | 13.5 | 38 | 7.1 | 3% | + | 0.93 | NWR | 11.9 |
| Y278 | 181.6 | 1 | 94 | 36% | + | ND | WR | 22.5 |

TABLE 3

| Variant | IMAC gel µg/mL | $^{14}C$ expression rank order | CFPS $^{14}C$ µg/mL | Suppression Efficiency | Binding | DAR | HIC Profile | $IC_{50}$ cell killing (ng/ml) |
|---|---|---|---|---|---|---|---|---|
| R355 | 86 | 7 | 36 | 21% | + | 1.14 | WR | 13.8 |
| T359 | 84 | 4 | 39 | 23% | + | 1.13 | WR | 7.5 |
| N389 | 63 | 6 | 37 | 22% | + | 1.54 | WR | 9.7 |
| S337 | 56 | 5 | 39 | 23% | + | ND | Unresolved | 6.9 |
| A339 | 94 | 2 | 45 | 26% | + | ND | Unresolved | 7.7 |
| L398 | 49 | 11 | 24 | 14% | + | ND | Single Peak | 9.4 |
| Q438 | 56 | 36 | ND | ND | + | 1.46 | WR | 10 |
| N421 | 27 | 15 | 18 | 11% | + | 1.35 | WR | 10.5 |
| S375 | 68 | 8 | 27 | 16% | + | ND | Single Peak | 12.3 |
| R344 | 52 | 14 | 20 | 12% | + | 1.13 | WR | 16.7 |
| G420 | 19 | 18 | 15 | 9% | + | 1.34 | WR | 9.4 |
| K340 | 20 | 20 | 12 | 7% | + | 1.49 | Low Signal | 12.9 |
| Q386 | 9 | 19 | 13 | 8% | + | 1.49 | NWR | 16.9 |
| K392 | 11 | 34 | 2 | 1% | + | 1 | NWR | 18 |
| S383 | 39 | 13 | 23 | 13% | + | 0.72 | WR | 21.3 |
| M358 | 25 | 16 | 16 | 10% | + | 0.93 |  | 21.6 |
| E356 | 44 | 10 | 25 | 14% | + | 0.66 | WR | 27 |
| K360 | 55 | 12 | 23 | 14% | + | 0.42 | WR | 31.2 |
| Y436 | 22 | 35 | ND | ND | + | 0.6 | Low Signal | 32.6 |
| N384 | 127 | 1 | 69 | 40% | + | 0.25 | WR | 34.9 |
| Q342 | 6.5 | 30 | 4.5 | 3% | + | 1.59 | Low Signal | 35.1 |

Example 3

Fidelity of Incorporation of a Non-Natural Amino Acid in an Exemplary Antibody-Drug Conjugate This Example describes an evaluation of the fidelity of incorporation of a non-natural amino acid in an exemplary antibody-drug conjugate. Trastuzumab substituted with p-azido-phenylalanine substituted at S136 conjugated with DBCO-MMAF was digested with trypsin and analyzed on an Agilent 6520 Accurate Mass Q-TOF LC-MS system equipped with a nano-electrospray ChipCube source. Peptides containing potential misincorporated amino acids and their wild-type counter parts were searched using extracted ion chromatograms from the LC-MS data within ±10 ppm of the theoretical m/z for the z=1-4 charge states of the peptide. If the m/z of the found peak were within ±10 ppm of the theoretical m/z and the correct charge state they were considered to be potential matches until MS/MS verification. In the absence of signal from misincorporation, the signal was assumed to be equal or less than the noise in the mass spectrum. The minimum fidelity rate was calculated as a noise to signal ratio. The signal was measured as the average of all monoisotopic ions across the peptide's elution profile for the most abundant charge state and the noise was estimated in the same spectrum in a region adjacent to the exhibiting a minimum amount of signal. Where an observed peptide contained a misincorporation event was found, its averaged signal was used in place of the noise measurement.

In the peptide map of the tested antibody-drug conjugate, peptide with nnAA+conjugated drug was detected at charge states 2 and 3 with an error of less than 4 ppm. At position 136, no tyrosine incorporation was present and the incorporation efficacy for pAzPhe was determined to be 98.3%. No tyrosine misincorporation was detected at the Phe positions across the detected IgG sequence. The overall, incorporation efficiency for Phe was measured to be at minimum 99.7%.

Example 4

Assessment of the Thermal Stability of Exemplary Antibody-Drug Conjugates

This example describes experiments designed to measure the thermal stability ($T_m$) of aglycosylated trastuzumab and trastuzumab variants. The thermal shift assay was carried out by mixing the protein to be assayed (Sutroceptin and variants) with an environmentally sensitive dye (SYPRO Orange, Life Technologies Cat #S-6650) in a buffered solution (PBS), and monitoring the fluorescence of the mixture in real time as it undergoes controlled thermal denaturation. The final concentration of the protein in the assay mixture was between 100-250 µg/mL, and the dye was 1:1000 diluted from the original stock (Stock dye is 5000× in DMSO). After dispensing 5 µL aliquots of the protein-dye mixture in a 384-well microplate (Bio-Rad Cat #MSP-3852), the plate was sealed with an optically clear sealing film (Bio-Rad Cat #MSB-1001), and placed in a 384-well plate real-time thermocycler (Bio-Rad CFX384 Real Time System). The protein-dye mixture was heated from 25° C. to 95° C., at increments of 0.1° C. per cycle (~1.5° C. per minute), allowing 3 seconds of equilibration at each temperature before taking a fluorescence measurement. At the end of the experiment, the melting temperature ($T_m$) was determined using the Bio-Rad CFX manager software. For protein samples with complex thermal transition profiles, the melting temperature ($T_m$) is calculated from the negative first-order derivative plot of fluorescence intensity (Y-axis) against temperature (X-axis), or by fitting the data to the Boltzmann sigmoidal model. The difference in melting temperature of IgG variants compared to the wild-type protein is a measure of the thermal shift for the protein being assayed.

The results of this assay for certain variants are shown in Table 4. In general, deflections in $T_m$ significantly below unsubstituted trastuzumab, particularly in $T_m1$, indicate an undesirable loss of stability and/or a propensity to aggregate. As such, trastuzumab variants that exhibit a $T_m1$ and/or $T_m2$ within about 5° C. of unsubstituted trastuzumab are preferred. More preferred are those variants that exhibit a $T_m1$ and/or $T_m2$ within about 3° C. of unsubstituted trastuzumab. Still more preferred are those variants that exhibit a $T_m1$ and/or $T_m2$ within about 2° C. of unsubstituted trastuzumab. Still more preferred are those variants that exhibit a $T_m1$ and/or $T_m2$ within about 1° C. of unsubstituted trastuzumab. The $T_m1$ and $T_m2$ can be measured in the unconjugated or conjugated forms.

TABLE 4

| Antibody or Antibody-Drug Conjugate | Trastuzumab Variant | $T_m1$ (° C.) | $T_m2$ (° C.) |
|---|---|---|---|
| Antibody | Aglycosylated trastuzumab | 63.5 +/− 0.6 | 76.5 +/− 0.1 |
| Antibody | T359 | 64.0 +/− 0.4 | 76.8 +/− 0.0 |
| Antibody | E293 | 59.7 +/− 0.7 | 76.1 +/− 0.1 |
| Antibody | K334 | 49.5 +/− 0.8 | 76.5 +/− 0.1 |
| Antibody | R355 | 63.6 +/− 0.4 | 76.8 +/− 0.1 |
| Antibody | N389 | 62.8 +/− 0.1 | 76.8 +/− 0.0 |
| Antibody-Drug conjugate | T359 | 63.9 +/− 0.6 | 76.7 +/− 0.1 |
| Antibody-Drug conjugate | E293 | 59.2 +/− 0.0 | 76.0 +/− 0.3 |
| Antibody-Drug conjugate | K334 | 59.0 +/− 0.2 | 76.3 +/− 0.2 |
| Antibody-Drug conjugate | R355 | 63.7 +/− 0.4 | 76.6 +/− 0.1 |
| Antibody-Drug conjugate | N389 | 61.9 +/− 0.5 | 76.4 +/− 0.0 |

Example 5

Characterization of Exemplary Antibody-Drug Conjugates: Light Chain Substitution Methods as described in Example 9 were used to create and analyze variants with light chain substitutions. Results of these characterization experiments are presented in Table 5.

TABLE 5

Selected LC variants

| Variant | Chain | Final Purified ADC (ug/mL) | DAR | HIC profile | SKBR3 Cell Killing IC$_{50}$ (ng/mL) |
|---|---|---|---|---|---|
| A43 | LC | 67.60 | 1.44 | WR | 3.73 |
| Y49 | LC | 123.46 | 1.86 | WR | 2.00 |
| S56 | LC | 97.40 | 1.78 | WR | 2.58 |
| G57 | LC | 89.78 | 1.66 | NWR | 3.43 |
| S60 | LC | 146.77 | 1.56 | NWR | 2.63 |
| S67 | LC | 121.38 | 1.53 | NWR | 3.73 |
| G68 | LC | 55.30 | 1.35 | NWR | 2.37 |
| T109 | LC | 95.58 | 1.62 | WR | 2.25 |
| A112 | LC | 80.50 | 1.10 | WR | 1.87 |
| S114 | LC | 92.86 | 0.96 | WR | 2.21 |
| A144 | LC | 61.74 | 1.39 | WR | 2.56 |
| A153 | LC | 104.07 | 1.53 | WR | 3.59 |
| S156 | LC | 77.65 | 1.36 | WR | 1.98 |
| G157 | LC | 65.25 | 0.98 | WR | 3.45 |
| S168 | LC | 86.99 | 1.10 | WR | 4.01 |
| A184 | LC | 66.15 | 1.20 | WR | 4.24 |
| S202 | LC | 88.17 | 1.71 | NWR | 2.56 |
| S203 | LC | 92.60 | 1.75 | WR | 2.46 |
| T206 | LC | 95.40 | 0.77 | WR | 4.93 |

Preferred variants include those with a non-natural amino acid replacing these positions of the light chain (LC): A043, Y049, S056, G057, S060, S067, G068, T109, A112, S114, A144, A153, S156, G157, S168, A184, S202, S203, and T206.

Variants that have a DAR of at least about 1.0 are also preferred. Still more preferred were variants including those with a non-natural amino acid replacing these positions of the light chain: A043, Y049, S056, G057, S060, S067, G068, T109, A112, A144, A153, S156, S168, A184, S202, and S203.

Variants that have a DAR of at least about 1.2 are also preferred. Still more preferred were variants including those with a non-natural amino acid replacing these positions of the light chain: A043, Y049, S056, G057, S060, S067, G068, T109, A144, A153, S156, A184, S202, and S203.

Variants that have a DAR of at least about 1.5 are also preferred. Still more preferred were variants including those with a non-natural amino acid replacing these positions of the light chain: Y049, S056, G057, S060, S067, T109, A153, S202, and S203.

Example 6

Assessment of Expression of HC-F404 in an RF-1 Attenuated Extract

To initially assess the effects of using an RF-1 attenuated E. coli strain on incorporation of a non-natural amino acid, 12 variants which poorly expressed in the RF-1 positive strain were expressed and scaled up in the RF-1 attenuated strain. One such variant, HC-F404, exhibited exceptionally desirable properties, as discussed below.

The cell free extract used for this cell free protein synthesis reaction was prepared from an OmpT sensitive RF-1 attenuated E. coli strain which has also been engineered to produce an orthogonal CUA-encoding tRNA for insertion of a non-natural amino acid at an Amber Stop Codon. After addition of DNA template that encodes for HC-F404 and WT LC, the cell free reaction was incubated at 30° C. for 12 h on a shaker at 650 rpm at a 1 ml scale×6 (for a total of 9 ml) in a Flower plate (m2p-labs # MTP-48-B). The protein was then purified over Protein A and Capto Adhere resin using a Protein Maker (Emerald Bio).

Conjugation with drug (DBCO-MMAF) and preparation of Antibody Drug Conjugates (ADC's) for further analysis was done as described previously.

Thermofluor analysis of the variants was carried out as described previously

HC variant F404 generated both in during TAG scan as well as in the intermediate scale showed good cell-killing capability (TAG Scan I: IC50=0.018 nM; Intermediate Scale up: IC50=0.023 nM), but DAR estimation on the basis of its HIC profile proved problematic, due to low resolution of the peaks, possibly due to inaccessibility of the drug to the analytical column during HIC analysis. However, MS analysis showed that it had a DAR of 1.74. Also, thermofluor analysis showed that the ADC version of HC-F404 had an improved (higher thermal stability) $T_m1$ (increase of 2.2° C.) compared to the antibody only.

TABLE 6A

Properties of HC-F404 variant

| Chain | Variant | Final Purified ADC concentration (ug/mL) | MS DAR Profile | SKBR3 Cell Killing IC$_{50}$ (ng/mL) |
|---|---|---|---|---|
| HC | F404 | 541 | 1.74 WR* | 3.5 |

*This DAR result is based on LC-MS analysis. The conjugated variant produced a Not-Well-Resolved (NWR) peak on the HIC assay, and DAR was determined using LC-MS

TABLE 6B

Thermofluor results for HC-F404 variant

| | Trastuzumab | Antibody Only | | Antibody-Drug Conjugate | |
|---|---|---|---|---|---|
| Chain | Variant | $T_m1$ (° C.) | $T_m2$ (° C.) | $T_m1$ (° C.) | $T_m2$ (° C.) |
| HC | F404 | 61.2 +/− 0.2 | 76.6 +/− 0.1 | 63.5 +/− 0.4 | 76.5 +/− 0.1 |

Example 7

Characterization of Exemplary Antibody-Drug Conjugates: Release Factor Analysis TAG Scan I Methods and List of Selected Variants The cell free extract used for cell free protein synthesis reactions were prepared from an OmpT sensitive RF-1 attenuated E. coli strain which has also been engineered to express an orthogonal CUA-encoding tRNA for insertion of a non-natural amino acid at an Amber Stop Codon. After addition of DNA template, cell free reactions were incubated at 30° C. for 12 h on a shaker at 650 rpm in Flower plates (m2p-labs # MTP-48-B). For synthesis of light chain variants (variants which had nnAA incorporation on the light chain), a DNA ratio of 4 ug/mL of light chain DNA to 8 μg/mL of heavy chain DNA was used. Each trastuzumab variant was produced in 1 mL scale in 48-well flower plates in singlicate. A total of 6 plates were used to express the variants.

Supernatant was captured with IMAC Phytip containing 40 μL resin by pipetting up and down 10 times slowly at a flow rate of 4.2 uL/min. Bound protein was eluted with 125 μL IMAC elution buffer (50 mM Tris pH 8.0, 300 mM NaCl, 500 mM Imidazole). Following purification, IMAC purified variants were quantified on a Caliper GXII system by comparing with by mass standards of HERCEPTIN® run on the same Protein Express LabChip (Caliper LifeSciences #760499). Samples were prepared for analysis as specified in the Protein Express Reagent Kit (Caliper Life Sciences #760328) with the exception that the samples (mixed in sample buffer) were heated at 65° C. for 10 minutes prior to analysis on the Caliper system.

Conjugation with drug (DBCO-MMAF) and preparation of Antibody Drug Conjugates (ADC's) for further analysis was done as described previously.

Positive results of these characterization experiments are presented in Table 7. In the Table, the following properties of the variants are shown: final concentration of antibody-drug conjugate made, ability to bind HER2-expressing cells, drug-antibody ratio (DAR, expressed as the number of cytotoxic agents per antibody), a comment regarding the HIC profile, and the observed IC$_{50}$ from the cell-killing assay described previously. In the comments regarding the HIC assay, SP corresponds to a profile that resolved well as a single peak, NWR corresponds to a poorly resolved profile and WR corresponds to a well-resolved HIC profile. Several of the variants that exhibited a single peak profile also exhibited potent killing, which indicates that the variant was indeed conjugated with drug, but failed to resolve on the HIC column.

TABLE 7

Selected Variants for Tag Scan I

| Variants | Chain | Final Purified ADC (ug/mL) | DAR | HIC Profile | SKBR3 cell killing IC$_{50}$ (ng/mL) |
|---|---|---|---|---|---|
| A023 | HC | 74 | 1.6 | WR | 7.1 |
| A084 | HC | 93 | 1.5 | WR | 8.7 |
| A118 | HC | 96 | 1.6 | WR | 7.3 |
| S119 | HC | 89 | 1.5 | NWR | 8.3 |
| T135 | HC | 64 | 1.6 | WR | 4.4 |
| S136 | HC | 71 | 1.6 | WR | 6.6 |
| G137 | HC | 53 | 1.4 | NWR | 7.4 |
| S160 | HC | 42 | 1.6 | NWR | 6.6 |
| G161 | HC | 25 | 1.2 | NWR | 8.9 |
| A162 | HC | 45 | 1.5 | WR | 7.9 |
| T164 | HC | 36 | 1.1 | NWR | 9.0 |
| T195 | HC | 40 | 1.6 | WR | 6.6 |
| T197 | HC | 29 | 1.2 | NWR | 8.7 |
| S219 | HC | 66 | 1.7 | WR | 6.6 |
| V282 | HC | 52 | 1.0 | NWR | 1.6 |
| T289 | HC | 46 | 0.3 | WR | 2.1 |
| Y296 | HC | 32 | 1.5 | WR | 7.2 |
| A330 | HC | 80 | ND | SP | 2.4 |
| T335 | HC | 43 | 0.7 | NWR | 2.3 |
| N361 | HC | 42 | 1.0 | WR | 5.9 |
| S400 | HC | 51 | 0.5 | WR | 7.1 |
| F404 | HC | 20 | ND | NWR | 4.3 |
| V422 | HC | 100 | 1.3 | WR | 4.0 |
| S440 | HC | 74 | 1.2 | WR | 6.1 |
| T260 | HC | 37 | 0.1 | NWR | 4.4 |
| S267 | HC | 94 | 1.7 | WR | 7.2 |
| H268 | HC | 45 | 0.4 | NWR | 7.5 |
| E272 | HC | 50 | 1.2 | WR | 3.0 |
| K274 | HC | 64 | 0.8 | WR | 2.8 |
| R292 | HC | 101 | ND | SP | 9.0 |
| E293 | HC | 133 | 1.7 | WR | 9.0 |
| N297 | HC | 45 | 1.7 | WR | 4.7 |
| S298 | HC | 60 | 1.5 | WR | 5.4 |
| V303 | HC | 75 | 1.5 | WR | 12.7 |
| V305 | HC | 66 | 1.5 | WR | 7.0 |
| I332 | HC | 47 | ND | NWR | 2.6 |
| E333 | HC | 47 | ND | NWR | 2.6 |
| K334 | HC | 83 | 1.8 | WR | 6.9 |
| K340 | HC | 76 | 1.5 | WR | 4.4 |
| G341 | HC | 29 | 1.5 | WR | 3.8 |
| Q342 | HC | 60 | 1.3 | WR | 4.8 |
| P343 | HC | 51 | 0.8 | WR | 6.6 |
| R355 | HC | 54 | 1.4 | WR | 4.6 |
| Q362 | HC | 89 | 1.1 | WR | 6.3 |
| Q386 | HC | 124 | ND | NWR | 4.0 |
| K392 | HC | 40 | 1.6 | WR | 3.4 |
| S424 | HC | 24 | 1.3 | WR | 4.9 |
| Q438 | HC | 33 | 1.5 | WR | 5.2 |
| S442 | HC | 57 | 1.4 | WR | 4.3 |
| L443 | HC | 39 | 1.4 | WR | 3.0 |

Preferred variants include those with a non-natural amino acid replacing these positions of the heavy chain (HC): A023, A084, A118, S119, T135, S136, G137, S160, G161, A162, T164, T195, T197, S219, V282, T289, Y296, A330, T335, N361, S400, F404, V422, S440, T260, S267, H268, E272, K274, R292, E293, N297, S298, V303, V305, I332, E333, K334, K340, G341, Q342, P343, R355, Q362, Q386, K392, F404, S424, Q438, S442 and L443.

Variants that have a DAR of at least about 0.7 are also preferred. Preferred variants include those with a non-natural amino acid replacing these positions of the heavy chain (HC): A023, A084, A118, S119, T135, S136, G137, S160, G161, A162, T164, T195, T197, S219, V282, Y296, T335, N361, V422, S440, S267, E272, K274, E293, N297, S298, V303, V305, K334, K340, G341, Q342, P343, R355, Q362, K392, F404, S424, Q438, S442 and L443.

Variants that have a DAR of at least about 1.0 are also preferred. Still more preferred were variants including those with a non-natural amino acid replacing these positions of the heavy chain: A023, A084, A118, S119, T135, S136, G137, S160, G161, A162, T164, T195, T197, S219, V282, Y296, N361, V422, S440, S267, E272, E293, N297, S298, V303, V305, K334, K340, G341, Q342, R355, Q362, K392, F404, S424, Q438, S442 and L443.

Variants that have a DAR of at least about 1.2 are also preferred. Still more preferred were variants including those with a non-natural amino acid replacing these positions of the heavy chain: A023, A084, A118, S119, T135, S136, G137, S160, G161, A162, T195, T197, S219, V282, Y296, V422, S440, S267, E272, E293, N297, S298, V303, V305, K334, K340, G341, Q342, R355, K392, F404, S424, Q438, S442 and L443.

Variants that have a DAR of at least about 1.5 are also preferred. Still more preferred were variants including those with a non-natural amino acid replacing these positions of the heavy chain: A023, A084, A118, S119, T135, S136, S160, A162, T195, S219, V282, Y296, S267, E293, N297, S298, V303, V305, K334, K340, G341, K392, F404, and Q438.

Example 8

Characterization of Exemplary Antibody-Drug Conjugates: Additional Release Factor Analysis TAG Scan II Methods and List of Selected Variants The cell free extract used for cell free protein synthesis reactions were prepared from an OmpT sensitive RF-1 attenuated E. coli strain which has also been engineered to produce an orthogonal CUA-encoding tRNA for insertion of a non-natural amino acid (p-azido-phenylalanine) at an Amber Stop Codon. After addition of DNA template, cell free reactions were incubated at 30° C. for 12 h on a shaker at 650 rpm in Flower plates (m2p-labs # MTP-48-B). For synthesis of light chain variants (variants which had nnAA incorporation on the light chain), a DNA ratio of 4 µg/mL of light chain DNA to 8 µg/mL of heavy chain DNA was used. Each trastuzumab variant was produced in 1 mL scale in 48-well flower plates in singlicate. A total of 6 plates were used to express the variants.

Supernatant was captured with IMAC Phytip containing 40 µL resin by pipetting up and down 10 times slowly at a flow rate of 4.2 µL/min. Bound protein was eluted with 125 µL IMAC elution buffer (50 mM Tris pH 8.0, 300 mM NaCl, 500 mM Imidazole). Following purification, IMAC purified variants were quantified on a Caliper GXII system by comparing with by mass standards of HERCEPTIN® run on the same Protein Express LabChip (Caliper LifeSciences #760499). Samples were prepared for analysis as specified in the Protein Express Reagent Kit (Caliper Life Sciences #760328) with the exception that the samples (mixed in sample buffer) were heated at 65° C. for 10 minutes prior to analysis on the Caliper system.

Conjugation with drug (DBCO-MMAF) and preparation of Antibody Drug Conjugates (ADCs) for further analysis was done as described previously.

Positive results of these characterization experiments are presented in Table 8. In the Table, the following properties of the variants are shown: final concentration of antibody-drug-conjugate made, the efficiency of expression of full length product compared to wild-type (suppression efficiency), ability to bind HER2-expressing cells, drug-antibody ratio (DAR, expressed as the number of cytotoxic agents per antibody), a comment regarding the HIC profile, and the observed IC$_{50}$ from the cell-killing assay described previously. In the comments regarding the HIC assay, SP corresponds to a profile that resolved well as a single peak, NWR corresponds to a poorly resolved profile and WR corresponds to a well-resolved HIC profile. Several of the variants that exhibited a single peak profile also exhibited potent killing, which indicates that the variant was indeed conjugated with drug, but failed to resolve on the HIC column.

In total, trastuzumab variants having a non-natural amino acid at 269 sites that were screened for the activities as described. Table 8 presents the 71 variants that had desirable DAR, expression profiles, suppression efficiencies, and/or $IC_{50}$ values. None of these properties could be predicted prior to testing, and many times the values for each individual property varied unpredictably within a sample. For example, one would generally expect that variants with high DAR would exhibit lower $IC_{50}$ values than those with low DAR. Nonetheless, the I51 variant, for example, exhibited a relatively low DAR of 0.6 yet exhibited an $IC_{50}$ of 1 ng/ml.

TABLE 8

Tag Scan II Variants

| Variants | Chain | MMAF (Post MQ) (ug/mL) | DAR | HIC Profile | SKBR3, $IC_{50}$, ng/mL | Suppression, % of wt by $^{14}C$ |
|---|---|---|---|---|---|---|
| G42 | HC | 64 | 1.4 | WR | 7.9 | 51 |
| Q3 | HC | 113 | 1.4 | WR | 5.3 | 73 |
| S7 | HC | 74 | 1.6 | WR | 4.6 | 50 |
| P14 | HC | 100 | 1.5 | WR | 9.6 | 63 |
| G16 | HC | 62 | 1.4 | NWR | 8.5 | 50 |
| R19 | HC | 130 | 1.6 | WR | 9 | 107 |
| S25 | HC | 197 | 1.5 | WR | 4.1 | 154 |
| A40 | HC | 124 | 1.7 | WR | 5.7 | 72 |
| K43 | HC | 84 | 1.5 | WR | 7.3 | 68 |
| I51 | HC | 30 | 0.6 | NWR | 1 | NR |
| Y52 | HC | 149 | 1.7 | WR | 8.9 | 74 |
| T53 | HC | 242 | 1.1 | WR | 8.0 | 122 |
| Y56 | HC | 287 | 1.1 | WR | 16.0 | 95 |
| S70 | HC | 59 | 1.5 | WR | 6 | 38 |
| N82A | HC | 83 | 1.4 | WR | 5.4 | 48 |
| D98 | HC | 46 | 0.6 | NWR | 5 | 48 |
| F100 | HC | 51 | 1.5 | WR | 48.2 | 33 |
| T110 | HC | 80 | 1.7 | WR | 4 | 89 |
| S112 | HC | 89 | 1.7 | WR | 4.7 | 90 |
| K121 | HC | 60 | 1.6 | WR | 4.4 | 57 |
| Y180 | HC | 72 | 1.6 | WR | 5.6 | 44 |
| S184 | HC | 42 | ND | SP | 9.9 | 56 |
| S190 | HC | 95 | 1.4 | WR | 7.1 | 63 |
| S192 | HC | 70 | 1.5 | WR | 5.6 | 66 |
| K214 | HC | 156 | 1.6 | WR | 5.8 | 41 |
| E216 | HC | 146 | 1.6 | WR | 4.9 | 72 |
| D221 | HC | 178 | 1.4 | WR | 9.6 | 75 |
| K222 | HC | 194 | 1.5 | WR | 8.4 | 87 |
| T225 | HC | 156 | 1.4 | WR | 8.3 | 81 |
| P227 | HC | 96 | 1.5 | NWR | 6.2 | 68 |
| P230 | HC | 157 | 1.5 | NWR | 6.0 | 122 |
| A231 | HC | 147 | 1.6 | NWR | 5.5 | 97 |
| P232 | HC | 107 | 1.5 | NWR | 5.5 | 86 |
| G236 | HC | 74 | 1.6 | WR | 4.5 | 70 |
| minus 1 | LC | 245 | 1.5 | WR | 8.8 | 66 |
| Q3 | LC | 266 | 1.1 | WR | 9.1 | 66 |
| T5 | LC | 252 | 1.2 | WR | 7.3 | 72 |
| S7 | LC | 275 | 1.3 | WR | 6 | 77 |
| P8 | LC | 256 | 1.3 | WR | 6.1 | 71 |
| S9 | LC | 290 | 1.1 | WR | 6.8 | NR |
| S10 | LC | 285 | 0.6 | WR | 7.9 | 76 |
| G16 | LC | 216 | 1.5 | NWR | 6.4 | 68 |
| D17 | LC | 159 | 1.2 | WR | 8.3 | 59 |
| R18 | LC | 230 | 1.3 | WR | 7.5 | 67 |
| T20 | LC | 230 | 1.2 | WR | 4.9 | 83 |
| T22 | LC | 229 | 1.4 | WR | 6.7 | 167 |
| S26 | LC | 209 | 1.1 | WR | 7.8 | 61 |
| Q27 | LC | 194 | 1.2 | WR | 8.0 | 70 |
| K45 | LC | 184 | 1.2 | WR | 4.6 | 66 |
| V58 | LC | 170 | 1.3 | NWR | 8.2 | 71 |
| S63 | LC | 219 | 1.5 | NWR | 6 | 85 |
| S65 | LC | 223 | 1.1 | WR | 8.7 | 83 |
| R66 | LC | 234 | 1.1 | WR | 9.0 | 93 |
| D70 | LC | 201 | 1.0 | WR | 3 | 73 |
| S77 | LC | 193 | 1.4 | WR | 5.2 | 67 |
| Q79 | LC | 207 | 1.3 | WR | 9.4 | 60 |
| K107 | LC | 223 | 1.2 | WR | 9.1 | 78 |
| N138 | LC | 132 | 0.6 | WR | 6 | 57 |
| R142 | LC | 140 | 1.2 | WR | 7.1 | 51 |
| E143 | LC | 192 | 0.9 | WR | 3 | 71 |
| N152 | LC | 185 | 1.2 | WR | 6.5 | 87 |
| S171 | LC | 250 | 1.1 | WR | 5.1 | 122 |
| S182 | LC | 217 | 1.3 | WR | 8.1 | 103 |
| K188 | LC | 150 | 1.4 | WR | 4.6 | 134 |
| Q199 | LC | 185 | 1.5 | WR | 7.1 | 71 |
| L201 | LC | 198 | 0.8 | WR | 5 | 127 |

Preferred variants include those with a non-natural amino acid replacing these positions of the heavy chain (HC): G042, Q003, S007, P014, G016, R019, S025, A040, K043, I051, Y052, T053, Y056, S070, N082A, D098, F100, T110, S112, K121, Y180, S184, S190, S192, K214, E216, D221, K222, T225, P227, P230, A231, P232, and G236.

Variants that have a DAR of at least about 0.7 are also preferred. Preferred variants include those with a non-natural amino acid replacing these positions of the heavy chain (HC): G042, Q003, S007, P014, G016, R019, S025, A040, K043, Y052, T053, Y056, S070, N082A, F100, T110, S112, K121, Y180, S190, S192, K214, E216, D221, K222, T225, P227, P230, A231, P232, and G236.

Variants that have a DAR of at least about 1.0 are also preferred. Still more preferred were variants including those with a non-natural amino acid replacing these positions of the heavy chain: G042, Q003, S007, P014, G016, R019, S025, A040, K043, Y052, T053, Y056, S070, N082A, F100, T110, S112, K121, Y180, S190, S192, K214, E216, D221, K222, T225, P227, P230, A231, P232, and G236.

Variants that have a DAR of at least about 1.2 are also preferred. Still more preferred were variants including those with a non-natural amino acid replacing these positions of the heavy chain: G042, Q003, S007, P014, G016, R019, S025, A040, K043, Y052, S070, N082A, F100, T110, S112, K121, Y180, S190, S192, K214, E216, D221, K222, T225, P227, P230, A231, P232, and G236.

Variants that have a DAR of at least about 1.5 are also preferred. Still more preferred were variants including those with a non-natural amino acid replacing these positions of the heavy chain: S007, P014, R019, S025, A040, K043, Y052, S070, F100, T110, S112, K121, Y180, K214, E216, K222, P227, P230, A231, P232, and G236.

Preferred variants include those with a non-natural amino acid replacing these positions of the light chain (LC): minus 1, Q003, T005, S007, P008, S009, S010, G016, D017, R018, T020, T022, S026, Q027, K045, V058, S063, S065, R066, D070, S077, Q079, K107, N138, R142, E143, N152, S171, S182, K188, Q199, and L201.

Variants that have a DAR of at least about 0.7 are also preferred. Preferred variants include those with a non-natural amino acid replacing these positions of the light chain: minus 1, Q003, T005, S007, P008, S009, G016, D017, R018, T020, T022, S026, Q027, K045, V058, S063, S065, R066, D070, S077, Q079, K107, R142, E143, N152, S171, S182, K188, Q199, and L201.

Variants that have a DAR of at least about 1.0 are also preferred. Still more preferred were variants including those with a non-natural amino acid replacing these positions of the light chain: minus 1, Q003, T005, S007, P008, S009, G016, D017, R018, T020, T022, S026, Q027, K045, V058, S063, S065, R066, D070, S077, Q079, K107, R142, N152, S171, S182, K188, and Q199.

Variants that have a DAR of at least about 1.2 are also preferred. Still more preferred were variants including those with a non-natural amino acid replacing these positions of the light chain: minus 1, T005, S007, P008, G016, D017, R018, T020, T022, Q027, K045, V058, S063, S077, Q079, K107, R142, N152, S182, K188, and Q199.

Variants that have a DAR of at least about 1.5 are also preferred. Still more preferred were variants including those with a non-natural amino acid replacing these positions of the light chain: minus 1, G016, S063, and Q199.

Example 9

Characterization of Exemplary Antibody-Drug Conjugates: Scale Up Analysis

Scale Up of Select Variants from TAG II Scan

Based on DAR and cell-killing data, a subset of trastuzumab variants with desirable characteristics were picked for small scale cell free expression in order to generate material for further characterization. The heavy chain variants selected for small scale production were: R019, S025, I051, S070, D098, T110, S112, K121, S136, Y180, S187, S190, K214, E216, D221, and K222. The light chain variants selected for small scale production were: (−)1, S007, P008, G016, T022, S063, R014, D070, N138, R142, E143 and N152.

The cell free reaction mix in which the variants were synthesized comprised of a 80%:20% blend of cell free extracts made from an OmpT sensitive RF-1 attenuated E. coli strain, and an OmpT sensitive RF-1 attenuated E. coli strain that was engineered to express an orthogonal CUA encoding tRNA, respectively. All variants were scaled up to 9 ml in flower plates (1.5 mL×6 replicates) and purified using Protein Maker (Emerald Bio).

Conjugation with drug (DBCO-MMAF) and preparation of Antibody Drug Conjugates (ADC's) for further analysis was done as described previously.

Positive results of these characterization experiments are presented in Table 9. In the Table, the following properties of the variants are shown: final concentration of antibody-drug-conjugate made, the efficiency of expression of full length product compared to wild-type (suppression efficiency), ability to bind HER2-expressing cells, drug-antibody ratio (DAR, expressed as the number of cytotoxic agents per antibody), a comment regarding the HIC profile, and the observed IC50 from the cell-killing assay described previously. In the comments regarding the HIC assay, SP corresponds to a profile that resolved well as a single peak, NWR corresponds to a poorly resolved profile and WR corresponds to a well-resolved HIC profile.

TABLE 9

A Subset of Preferred variants

| Chain | Variant | Final Purified ADC concentration (ug/mL) | DAR | HIC Profile | SKBR3 Cell Killing IC$_{50}$ (ng/mL) |
|---|---|---|---|---|---|
| HC | R19 | 146 | 1.67 | WR | 5.4 |
| HC | S25 | 218 | 1.55 | WR | 4.9 |
| HC | S70 | 134 | 1.67 | WR | 4.6 |
| HC | T77 | 192 | 1.05 | WR | 7.5 |
| HC | T110 | 196 | 1.46 | WR | 4.3 |
| HC | S112 | 212 | 1.6 | WR | 1.8 |
| HC | Y180 | 264 | 1.29 | WR | 4.9 |
| HC | Y79 | 412 | 0.46 | WR | 8.1 |
| HC | K121 | 319 | 1.61 | WR | 2.8 |
| HC | S190 | 135 | 1.23 | WR | 5.0 |
| HC | K214 | 202 | 1.47 | WR | 2.5 |
| HC | E216 | 234 | 1.3 | WR | 2.8 |
| HC | D221 | 284 | 1.16 | WR | 3.5 |
| HC | K222 | 308 | 1.21 | WR | 3.0 |
| LC | minus 1 | 804 | 1.52 | WR | 4.8 |
| LC | S7 | 378 | 1.50 | WR | 2.7 |
| LC | P8 | 784 | 1.46 | WR | 4.1 |
| LC | G16 | 363 | 1.64 | WR | 3.0 |
| LC | T22 | 392 | 1.50 | WR | 4.3 |
| LC | S63 | 441 | 1.58 | WR | 3.6 |
| LC | R142 | 377 | 1.61 | WR | 2.5 |
| LC | N152 | 388 | 1.42 | WR | 3.1 |

Example 10

Characterization of Exemplary Antibody-Drug Conjugates: Thermofluor Analysis

Thermofluor analysis of the variants was carried out as described previously. Thermofluor results are in Table 10.

TABLE 10

Thermofluor data for small Scale production variants

| | Trastuzumab | Antibody Only | | Antibody-Drug Conjugate | |
|---|---|---|---|---|---|
| Chain | Variant | $T_m1$ (° C.) | $T_m2$ (° C.) | $T_m1$ (° C.) | $T_m2$ (° C.) |
| | Aglycosylated Trastuzumab | 61.4 +/− 0.6 | 76.2 +/− 0.1 | N/A | N/A |
| LC | minus 1 | 61.7 +/− 0.4 | 75.6 +/− 0.1 | 61.3 +/− 0 | 74.4 +/− 0.1 |
| LC | S7 | 62 +/− 0.1 | 76.9 +/− 0 | 60.7 +/− 0.1 | 76.2 +/− 0 |
| LC | P8 | 61.8 +/− 0.1 | 71 +/− 0 | 61.2 +/− 0.7 | 70.3 +/− 0 |
| LC | G16 | 61.9 +/− 0.1 | 74.1 +/− 0.1 | 61.1 +/− 0.5 | 73.4 +/− 0.1 |
| LC | T22 | 61.7 +/− 0 | 76.8 +/− 0 | 61.6 +/− 0.2 | 76.4 +/− 0.1 |
| LC | S63 | 61.7 +/− 0.1 | 75.5 +/− 0 | 61.4 +/− 0 | 74.3 +/− 0 |
| LC | D70 | 61.9 +/− 0.1 | 76.6 +/− 0.1 | 61.8 +/− 0 | 76 +/− 0.1 |

TABLE 10-continued

Thermofluor data for small Scale production variants

| | Trastuzumab | Antibody Only | | Antibody-Drug Conjugate | |
|---|---|---|---|---|---|
| Chain | Variant | $T_m1$ (° C.) | $T_m2$ (° C.) | $T_m1$ (° C.) | $T_m2$ (° C.) |
| LC | N138 | 61.9 +/− 0.1 | 75.6 +/− 0.2 | 61.6 +/− 0.4 | 74.4 +/− 0 |
| LC | R142 | 61.8 +/− 0.1 | 73.9 +/− 0.1 | 61.7 +/− 0.1 | 72.3 +/− 0.2 |
| LC | E143 | 62 +/− 0.1 | 76.2 +/− 0 | 61.4 +/− 0.1 | 75 +/− 0 |
| LC | N152 | 59.3 +/− 0 | 76.3 +/− 0 | 59.3 +/− 0 | 76.5 +/− 0 |
| LC | L201 | 62 +/− 0.1 | 75.6 +/− 0.1 | 61.2 +/− 0.1 | 74.4 +/− 0 |
| HC | R19 | 61.5 +/− 0.4 | 77.1 +/− 0.3 | 61.6 +/− 0.4 | 73.7 +/− 0 |
| HC | S25 | 61.4 +/− 0 | 75 +/− 0 | 61.6 +/− 0.3 | 72.4 +/− 0 |
| HC | I51 | 61.6 +/− 0.6 | 72.7 +/− 0.1 | 61 +/− 0 | 71.8 +/− 0.2 |
| HC | S70 | 61.6 +/− 0.2 | 77.8 +/− 0.1 | 61.5 +/− 0.6 | 76.2 +/− 0 |
| HC | T77 | 61.8 +/− 0.5 | 75 +/− 0.1 | 61.5 +/− 0.1 | 73.3 +/− 0 |
| HC | Y79 | 61.6 +/− 0.2 | 76.1 +/− 0.1 | 61.7 +/− 0.1 | 76 +/− 0.1 |
| HC | D98 | 62.1 +/− 0.1 | 75.3 +/− 0.2 | 61.5 +/− 0.3 | 74.4 +/− 0.1 |
| HC | T110 | 61.6 +/− 0.2 | 73.6 +/− 0 | 61.4 +/− 0 | 71.5 +/− 0.1 |
| HC | S112 | 61.5 +/− 0.1 | 72.6 +/− 0.1 | 61.8 +/− 0.3 | 73.9 +/− 0 |
| HC | K121 | 61.4 +/− 0.1 | 75.1 +/− 0 | 61.4 +/− 0.1 | 74.7 +/− 0.1 |
| HC | S136 | 61.4 +/− 0.1 | 76.7 +/− 0.2 | 61.1 +/− 0.2 | 76.3 +/− 0 |
| HC | Y180 | 61.4 +/− 0.1 | 76.2 +/− 0 | 61.6 +/− 0.3 | 75.4 +/− 0.6 |
| HC | S187 | 62.2 +/− 0.1 | 68.5 +/− 0.3 | 61.7 +/− 0.4 | 68.3 +/− 0 |
| HC | S190 | 61.5 +/− 0.2 | 77.2 +/− 0.1 | 59.2 +/− 0 | 77 +/− 0.1 |
| HC | K214 | 59.1 +/− 0.1 | 76.9 +/− 0.1 | 59.1 +/− 0 | 76.3 +/− 0.1 |
| HC | E216 | 59.1 +/− 0 | 76.5 +/− 0 | 59.1 +/− 0.1 | 76.2 +/− 0.1 |
| HC | D221 | 59.1 +/− 0 | 76.7 +/− 0.1 | 59 +/− 0.1 | 76.7 +/− 0.1 |
| HC | K222 | 59.1 +/− 0.1 | 76.7 +/− 0.1 | 59 +/− 0.1 | 76.5 +/− 0.1 |

Variants subject to thermofluor analysis included those with a non-natural amino acid replacing these positions of the heavy chain: R019, S025, I051, S070, T077, Y079, D098, T110, S112, K121, S136, Y180, S187, S190, K214, E216, D221, and K222.

Variants subject to thermofluor analysis also included those with a non-natural amino acid replacing these positions of the light chain: minus 1, S007, P008, G016, T022, S063, D070, N138, R142, E143, N152, and L201.

Example 11

Characterization of Exemplary Antibody-Drug Conjugates: Kinectics Analysis

Conjugation Kinetics of Selected Variants

Rates of conjugation were determined for five variants that showed wide range of drug to antibody conjugate ratio. Reactions were initiated by mixture of variants with drug (DBCO-MMAF) in PBS (pH7.4) at 20° C. in duplicates for 15 min, 30 min, 1 hr, 2 hr, 4 hr, 8 hr and 16 hr. Final concentrations of antibody in mixture range from 0.2 to 2 uM. Final drug concentration for all reaction is 100 uM. At the end of incubation period, NaAzide was added to the mixture to a final concentration of 10 mM. Final mixture was purified by Zeba and MustangQ plates as previously described. Concentration of IgG was determined by Caliper using HERCEPTIN® as mass standard. Fraction of fully conjugated variants was determined by HIC as previously described.

TABLE 11

Half-lives and DAR of variants

| | HC-S112 | HC-T110 | HC-T77 | HC-Y79 | HC-F126 |
|---|---|---|---|---|---|
| $T_{1/2}$ | 6.2 h | 10.5 h | ~40 h | ~270 h | ND |
| DAR | 1.7 | 1.6 | 1.1 | 0.4 | 0 |

Figure 5A:
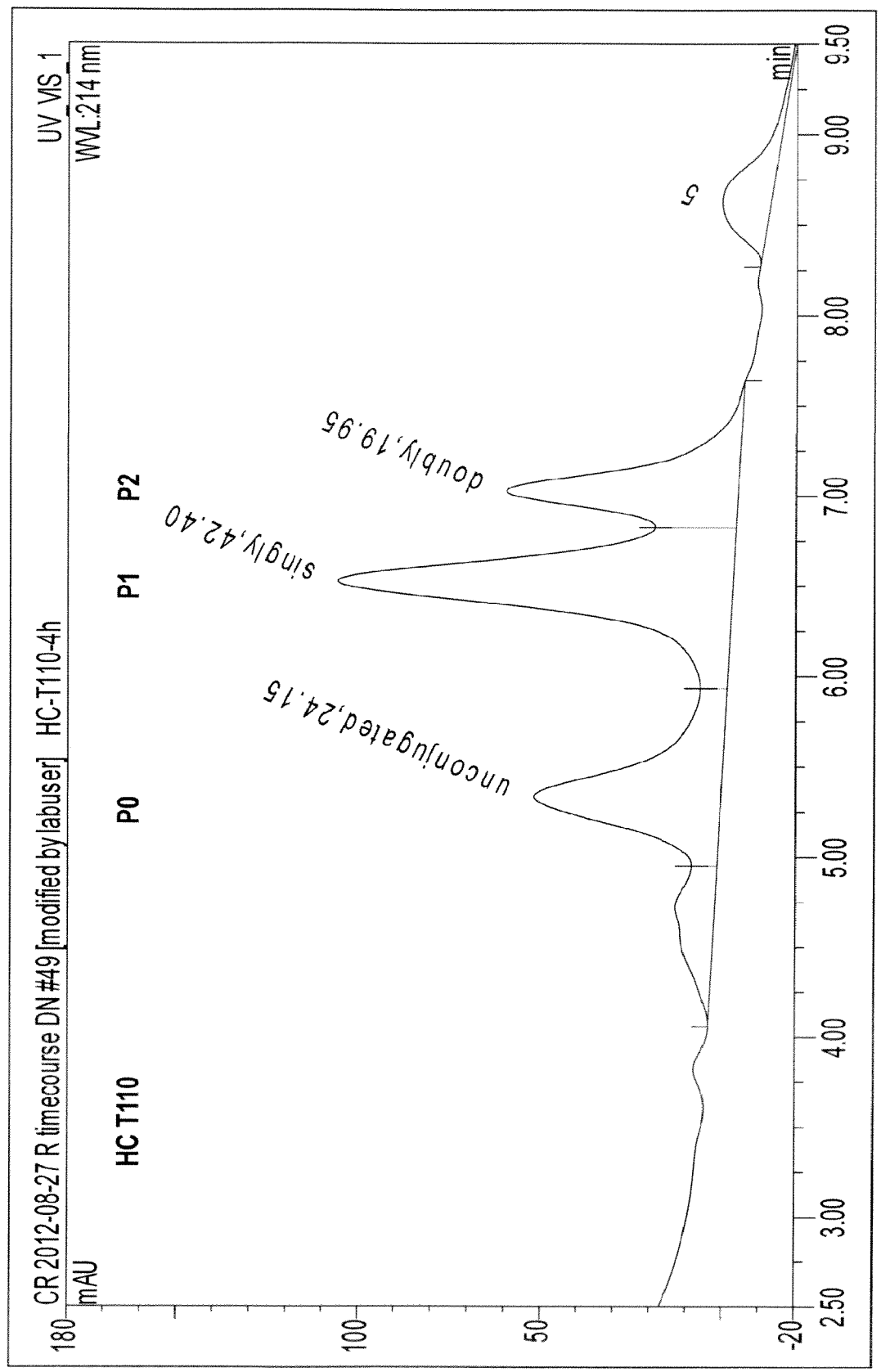
FIGS. 5A and 5B depict exemplary HIC traces of two variants (HC T110 and HC S112), showing peaks corresponding to unconjugated, partially conjugated and fully conjugated IgGs.
Figure 5B:
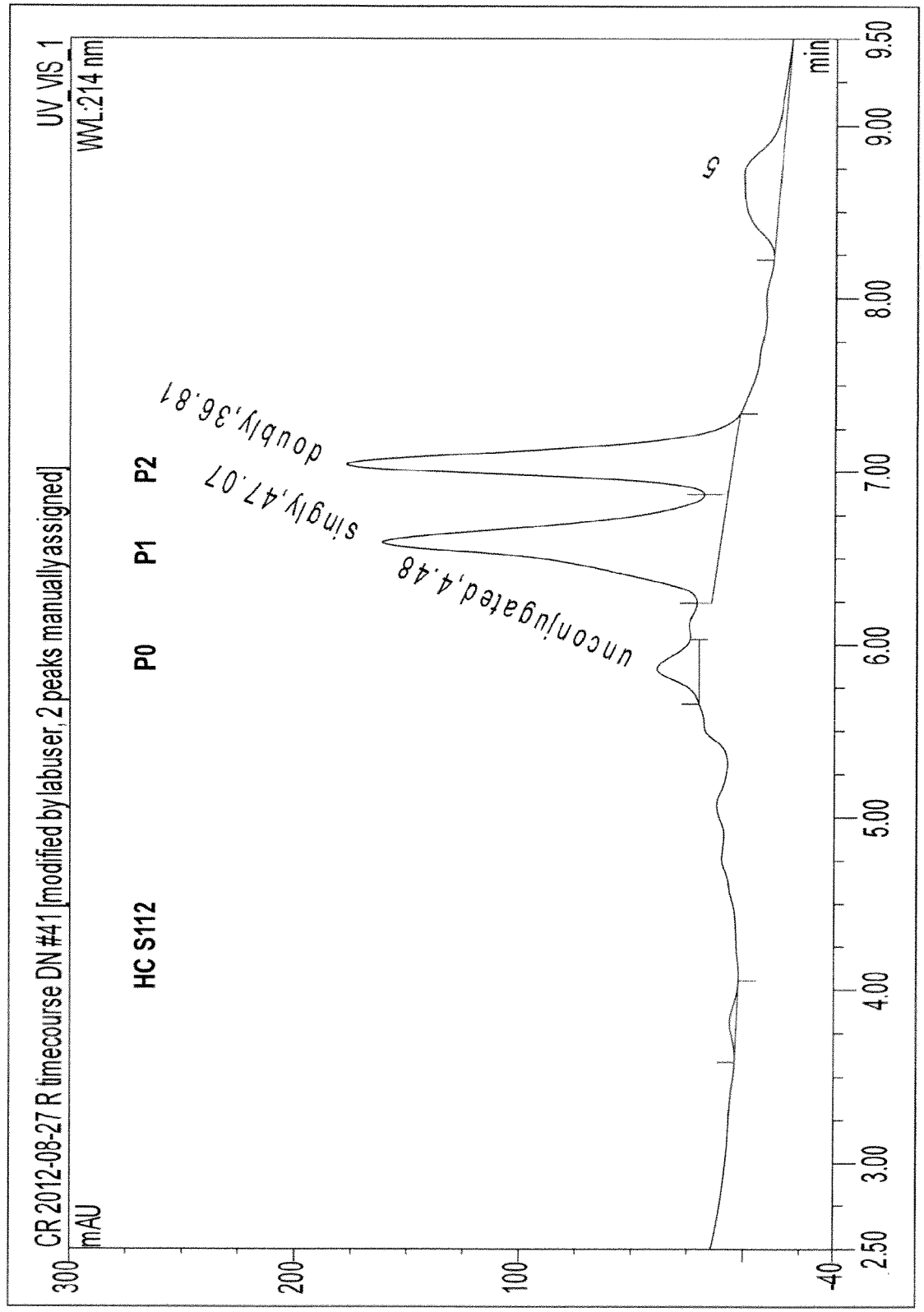
Figure 6A:
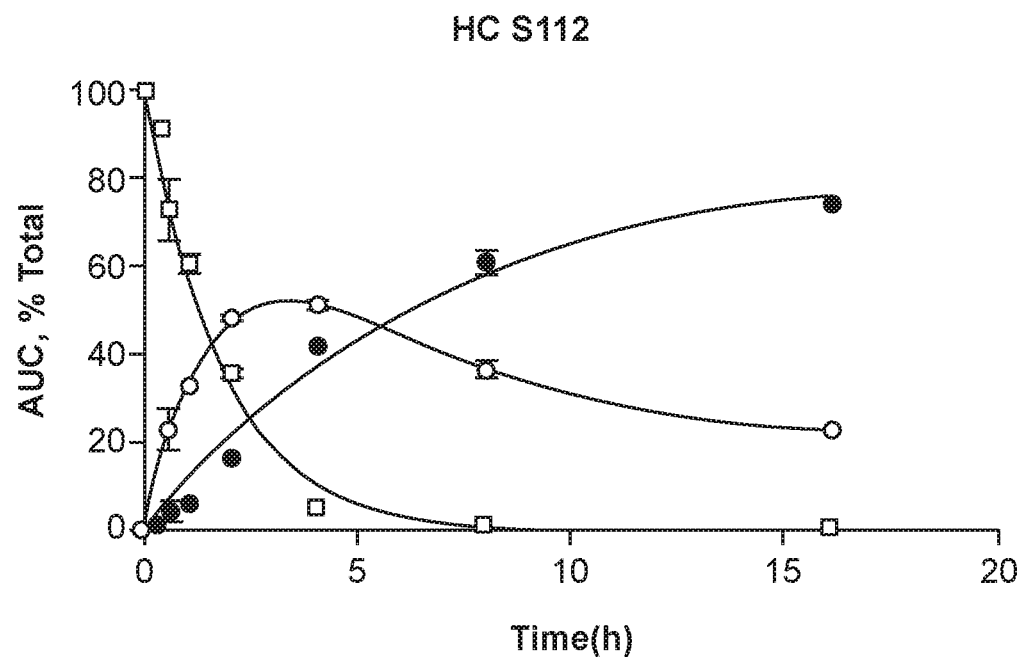
FIGS. 6A-6E depict exemplary embodiments showing site-specific conjugation.
Figure 6B:
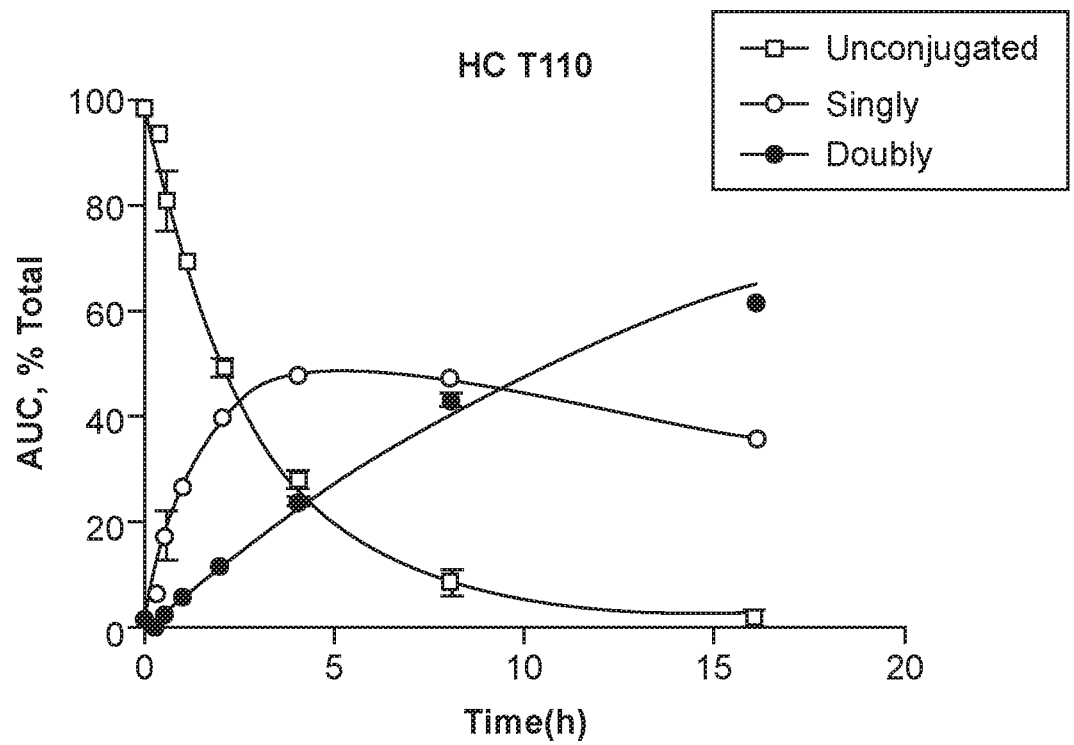
Figure 6C:
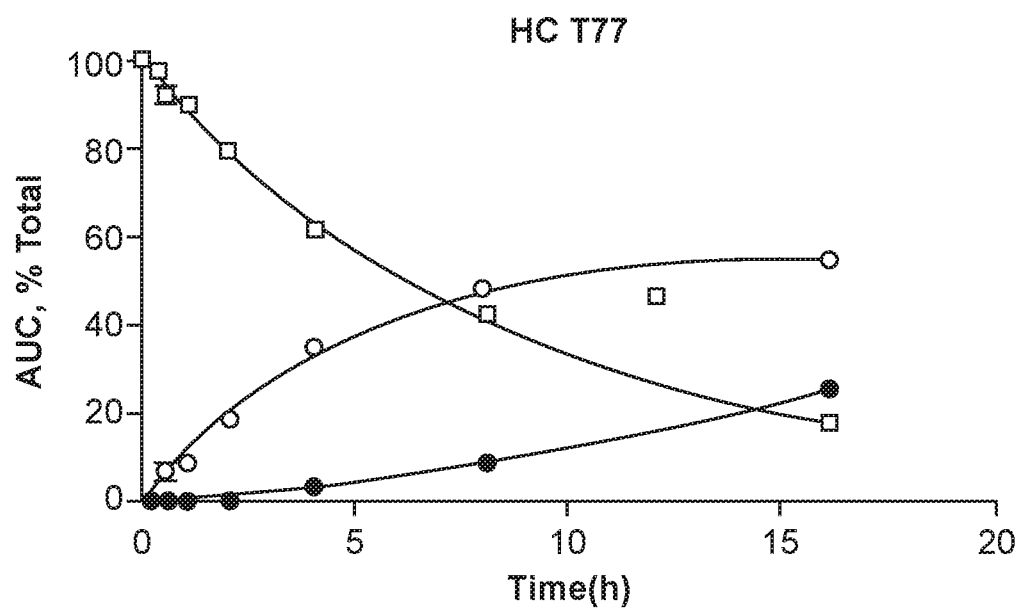
Figure 6D:
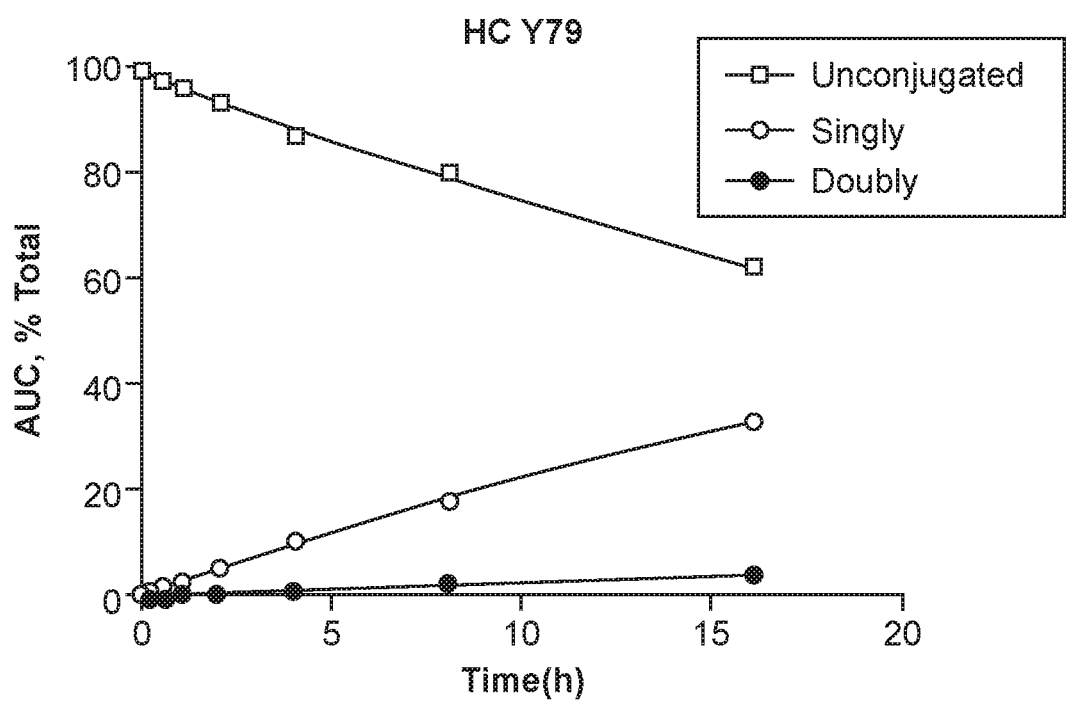
Figure 6E:
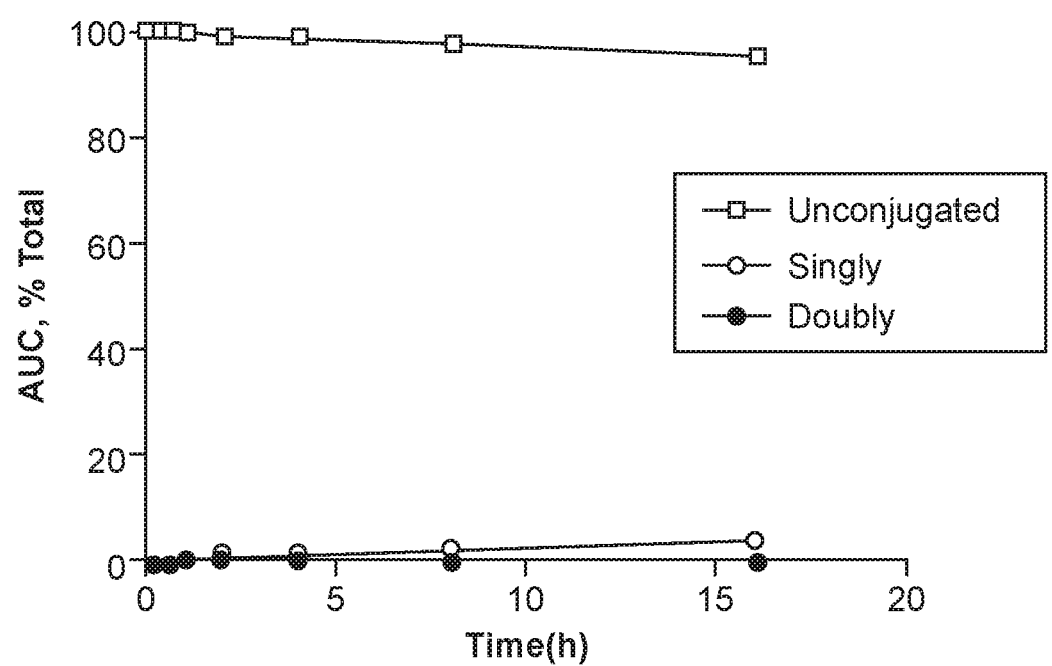

FIGS. 5A and 5B provides the HIC traces of two variants (HC T110 and HC S112). The traces showed three peaks (P0, P1 and P2) corresponding to peaks with unconjugated IgG, singly conjugated IgG and fully conjugate IgG, respectively.

FIGS. 6A through 6E show that conjugation of para-azido phenylalanine (pAzF) variants is site specific. Percentages of total of single and fully conjugated antibodies were separated by HIC.

Example 12

Characterization of Exemplary Antibody-Drug Conjugates: Suppression Comparison Analysis Comparison of Suppression by Para-azido Phenylalanine (pAzF) and Par-azido Methyl Phenylalanine (pAzMeF)

Eleven variants with a range of suppression efficiencies were expressed in a cell-free protein synthesis reaction as follows as described in Zawada et al., 2011, Biotechnol. Bioeng. 108(7): 1570-1578 with the modifications described below. Unsubstituted trastuzumab was also made as a control. Cell-free extracts containing tRNA and OmpT sensitive RF1(80/20 blend of strains 16/23) were treated with 50 μM iodoacetamide for 30 min at RT (20° C.) and added to a premix containing all other components except for GSSG, non-natural amino acids, tRNA synthetases, T7 RNAP, DsbC, PDI, and template DNA. All remaining reagents except DNA were then added to the mixture. Cell free reactions were initiated by addition of plasmid DNA of selected variants and incubated at 30° C. for 12 h on a shaker at 450 rpm in 96-well plates. The reaction was incubated further at 4° C. for 5 h. The final concentration in the protein synthesis reaction was 30% cell extract, 1 mM para-azido phenylalanine (pAzF) (RSP Amino Acids) with 0.37 mg/mL M jannaschii pAzF-specific amino-acyl tRNA synthetase (FRS), or 1 mM para-azido methyl phenylalanine (pAzMeF)

with 0.37 mg/mL p-cyanophenylalanine specific aminoacyl-tRNA synthetase (Young et al, 2011, Biochem. 50: 1894-1900), 2 mM GSSG, 0.29 mg/mL PDI (Mclab), 100 μg/mL E. coli DsbC, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for Tyrosine and Phenylalanine), 4 mM sodium oxalate, 1 mM putrescine, 1.5 mM spermidine, 15 mM potassium phosphate, 100 nM T7 RNAP, 2 μg/mL trastuzumab light chain DNA, 8 μg/mL trastuzumab-(His)6 heavy chain DNA. Each trastuzamab variant was produced in 100 uL scale in 96-well plates in duplicates with $^{14}C$ for each variant. It should be noted that all trastuzumab variants thus produced were aglycosylated.

To monitor protein synthesis reactions were spiked with 3% (v/v) 1-[U-14C]-leucine (300 mCi/mmole; GE Life Sciences, Piscataway, N.J.). The suppression of amber codon at different sites of the heavy chain and light chain was determined by [$^{14}C$]-autoradiograhy of reducing SDS-PAGE gels. Full length trastuzumab heavy chain and suppressed tastuzumab heavy chain variants run at 50 kD on SDS-PAGE. Full length trastuzumab light chain and suppressed tastuzumab light chain variants run at 30 kD on SDS-PAGE. Non suppressed (truncated) trastuzumab variants run at a lower molecular weight. Amber suppression in the heavy or light chain is determined by:

$$\text{supression} = \frac{\text{band intensity of suppressed heavy or light chain } TAG \text{ variant}}{\text{band intensity of wild type heavy or light chain}}$$

Figure 7A:
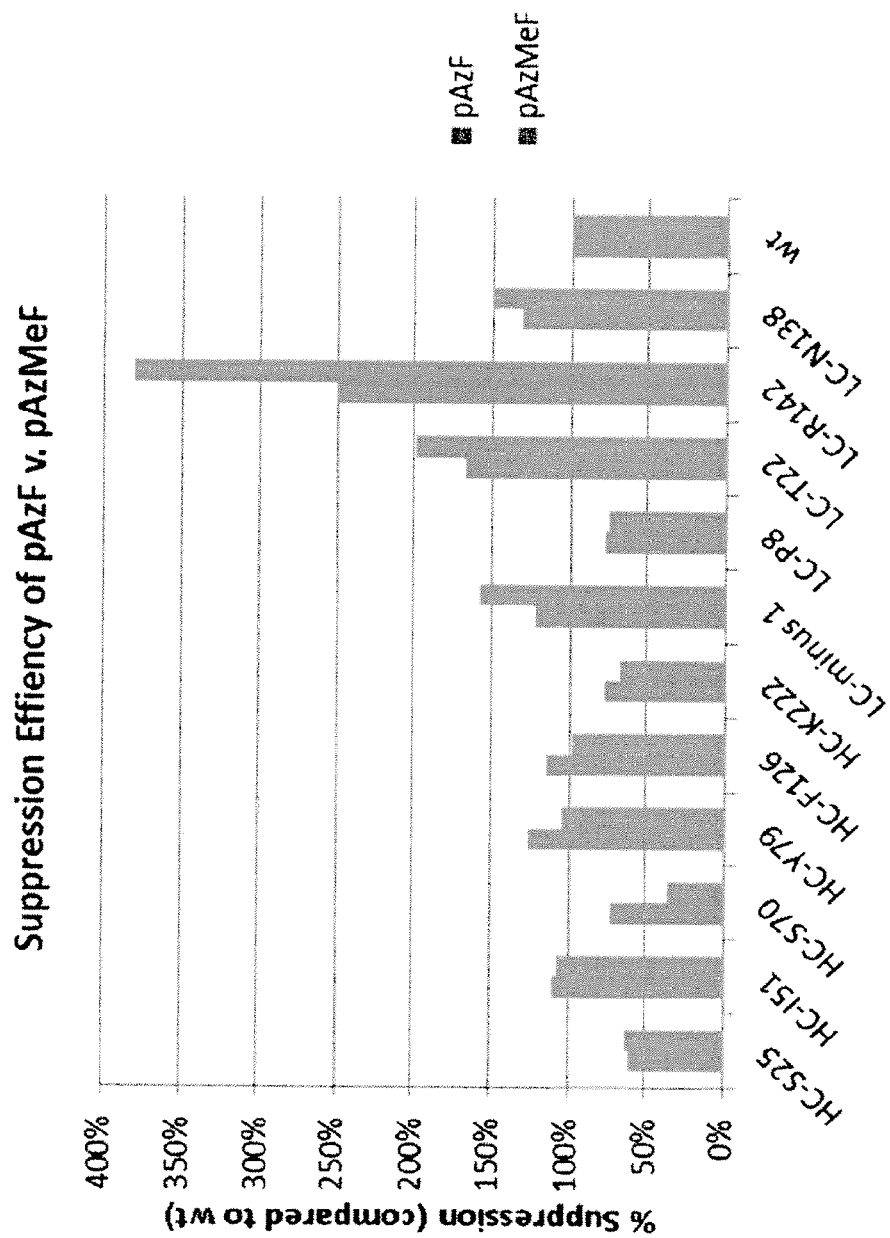
FIGS. 7A and 7B depict suppression efficiency and soluble yield comparison data of antibodies comprising different unnatural amino acids
Figure 7B:
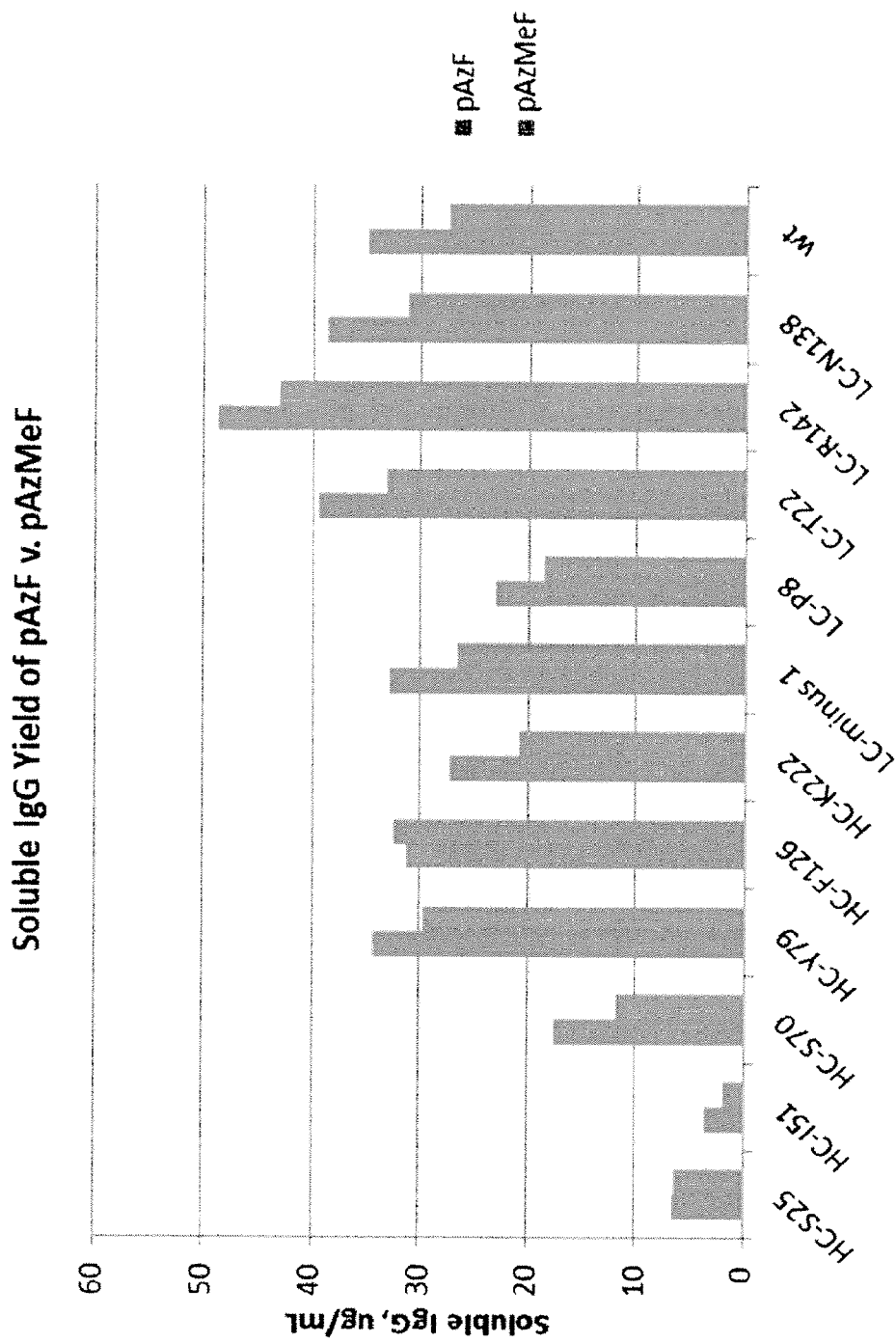

Band intensity was determined by ImageQuant (Amersham Biosciences Corp.; Piscataway, N.J.). In FIG. 7A, the suppression efficiency of pAzF and pAzMeF variants are compared. Suppression efficiency is calculated as variant HC band intensity over wild type HC band intensity or variant LC band intensity over wild type LC band intensity. In FIG. 7B, the soluble IgG yield of pAzF and pAzMeF variants are compared. The amount of IgG is computed according to the formula: soluble counts/full counts*IgG band intensity/total lane intensity*2*74008.02 Da/47 Leucines.

Example 13

Transfer of Sites of Non-Natural Amino Acid Incorporation to Another Antibody

To test whether sites for incorporation of non-natural amino acids can be transferred between two distinct IgG sequences with predictable DARs, a second antibody containing a non-natural amino acid at representative sites was assessed. For this experiment, brentuximab was chosen as the second antibody (See SEQ ID NO.: 3 and SEQ ID NO.:4). Several sites were chosen from the trastuzumab mutagenesis study exhibiting varying DARs. In the heavy chain, sites corresponded to K121, Y180, K133, S157, F126, and P127 (EU Numbering). In the light chain, sites corresponded to R142, N152, Q147, E161, K149, and Q155 (EU Numbering). The TAG stop codon was inserted into the brentuximab sequence using standard quick change based site directed mutagenesis, and the identity of each variant was confirmed by DNA sequencing. Mini Prep DNA was prepared using a Qiagen Kit, for use as a template to drive the cell free protein synthesis reaction.

The variants were synthesized in a reaction mix that contained an OmpT sensitive RF-1 protein and an in vivo expressed orthogonal CUA encoding tRNA. All variants were scaled up to 9 ml in flower plates (1.5 mL×6 replicates) and purified using a Protein Maker (Emerald Bio).

Conjugation with drug (DBCO-MMAF) and preparation of Antibody Drug Conjugates (ADC's) for further analysis was done as described previously. DARs were identified by the HIC profiling method previously described.

The results from the experiment suggest that sites can generally be predictably transferred between two distinct IgGs.

TABLE 12A

A Subset of Preferred HC variants

| Variants | DAR | |
|---|---|---|
| | trastuzumab | brentuximab |
| HC-K121 $^{TAG}$ | 1.6 | 1.4 |
| HC-Y180 $^{TAG}$ | 1.6 | 0.5 |
| HC-K133 $^{TAG}$ | 0.7 | 0.8 |
| HC-S157 $^{TAG}$ | 0.9 | 1.1 |
| HC-F126 $^{TAG}$ | — | — |
| HC-P127 $^{TAG}$ | — | — |

TABLE 12B

A Subset of Preferred LC variants

| Variants | DAR | |
|---|---|---|
| | trastuzumab | brentuximab |
| LC-R142 $^{TAG}$ | 1.2 | 1.3 |
| LC-N152 $^{TAG}$ | 1.2 | 1.3 |
| LC-Q147 $^{TAG}$ | 0.8 | 1 |
| LC-E161 $^{TAG}$ | 0.8 | NA |
| LC-K149 $^{TAG}$ | 0.1 | 0.1 |
| LC-Q155 $^{TAG}$ | 0.1 | 0.1 |

To further characterize brentuximab conjugates, variants containing amber mutations at heavy chain positions K121 or F404 or light chain position N152 were selected for scale up and additional characterization. As a control, trastuzumab containing an amber mutation at F404 was also expressed expressed TAG codon was inserted by overlapping PCR mutagenesis at the nucleotides corresponding to positions K121 and F404 on heavy chain and N152 on light chain and separately cloned into expression vector pYD317.

The cell free reaction mix in which the brentuximab and trastuzumab variants were synthesized comprised a blend of cell free extracts made from an OmpT sensitive RF-1 attenuated E. coli strain, and an OmpT sensitive RF-1 attenuated E. coli strain which was engineered to produce an orthogonal CUA-encoding tRNA for insertion of a non-natural amino acid at an Amber Stop Codon. The variants were expressed in a cell-free protein synthesis reaction as described in Zawada et al., 2011, Biotechnol. Bioeng. 108 (7)1570-1578 with the modifications described below. Cell-free extracts were treated with 50 μM iodoacetamide for 30 min at RT (20° C.) and added to a premix containing all other components except for DNA encoding the variants of interest. The final concentration in the protein synthesis reaction was 30% cell extract, 1 mM para-azido methyl phenylalanine (pAzMeF) (RSP Amino Acids), 0.37 mg/mL

*M jannaschii* pAzMeF-specific amino-acyl tRNA synthetase (FRS), 2 mM GSSG, 0.29 mg/mL PDI (Mclab), 30 μg/mL *E. coli* DsbC, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for Tyrosine and Phenylalanine), 4 mM sodium oxalate, 1 mM putrescine, 1.5 mM spermidine, 15 mM potassium phosphate, 100 nM T7 RNAP. Plasmid ratios of HC to LC were tested to find the optimal condition: 3:1, 2:1, 1:1 and 1:2. Total plasmid concentration kept constant at 10 ug/mL. After addition of DNA template, cell free reactions were incubated at 30° C. for 12 h on petri dishes and followed by 14C assay analysis. Maximum yield was achieved at 1:1 ratio. 10 mL cell-free reactions were carried under this condition.

To purify the variants, 10 ml of crude cell-free for each variant was first diluted 1:0.5 with equilibration buffer (50 mM sodium phosphate, pH 7) and spun at 11,000×g for 30 minutes. The supernatant was then passed through a 0.45 micron syringe filter prior to being loaded with a 2 minute residence time onto a pre-equilibrated 1 mL MabSelect Sure HiTrap (GE Lifesciences) to capture the IgG variants. The column was then washed with 7.5 CV (column volume) of wash buffer 1 (100 mM sodium phosphate and 800 mM Arginine, pH 7) and followed by 7.5CV of wash buffer 2 (50 mM sodium phosphate and 0.5% (v/v) Triton X-100, pH 7.3). After washing with 7.5CV of equilibration buffer, each variant was eluted with 4CV elution buffer (100 mM sodium citrate and 300 mM Arginine, pH 3). The elution pool was adjusted to pH 7 by addition of 30% (v/v) of 1M Tris, pH9.

The collected elution pool was buffer exchanged into PBS via overnight dialysis in 10 kD Slide-A-Lyzer (Pierce) units. The dialyzed material was then concentrated using an Amicon Ultra-15 (Millipore) centrifugal filter unit to a concentration of 5-10 mg/mL.

The purified variants were conjugated as follows. DBCO-MMAF 2 (ACME Bioscience; Palo Alto, Calif.) was dissolved in DMSO to a final concentration of 5 mM. The compound was diluted with PBS to a concentration of 1 mM and then added to purified trastuzumab variants in IMAC elution buffer to achieve a final drug concentration of 100 μM. Mixture was incubated at RT (20° C.) for 17 hours. Reaction was stopped by adding Sodium Azide to final concentration of 100 mM and buffer exchanged using Zeba plates (Thermo Scientific; Waltham, Mass.) equilibrated in 1×PBS.

DAR for the aglycosylated variants was determined by LC-MS as follows. ADCs by LCMS Samples were run on a Waters Aquity UPLC system attached a Xevo QTOF. Proteins were separated on an Agilent PLRP-S column (2.3×50 mm, 5 μm, 4000 Å) at 80° C. Mobile phases: A: 0.1% formic acid water; b: 20:80 isopropanol:acetonitrile, 0.1% formic acid. Samples were desalted on column for 0.4 minutes at 10% B followed by a step gradient from 30% B to 40% B over 7 minutes, 40% B to 60% B over 3 minutes. Data was acquired over the whole LC elution using a cone voltage of 35V. Spectra were analyzed using MassLynx software. DAR values were calculated as a weighted average and are shown in Table 13.

TABLE 13

DAR values for ADCETRIS ® ADCs

| Variant | Drug | DAR |
|---|---|---|
| Aglycosylated Brentuximab IgG HC-F404 | DBCO-MMAF 2 | 1.87 |
| Aglycosylated Brentuximab IgG HC-K121 | DBCO-MMAF 2 | 1.79 |
| Aglycosylated Brentuximab IgG LC-N152 | DBCO-MMAF 2 | 1.74 |
| Aglycosylated Trastuzumab IgG HC-F404 | DBCO-MMAF 2 | 1.97 |

Next, cell binding and cell killing activities of the variants were measured as follows. Karpas 299 and L540 cell lines were obtained from German Collection of Microorganisms and Cell Cultures (DSMZ) and SKBR3 and Raji cell lines were obtained from American Type Culture Collection (ATCC). Cells were grown in RPMI 1650 medium (Cellgro-Mediatech; Manassas, Va.) containing 20% heat-inactivated fetal bovine serum (Hyclone; Thermo Scientific; Waltham, Mass.), 2 mM glutamax (Invitrogen; Carlsbad, Calif.) and 1× penicillin/streptomycin (Cellgro-Mediatech; Manassas, Va.). Adherent SKBR3 cells were grown in DMEM/Nutrient F-12 Ham (50:50) high glucose medium (Cellgro-Mediatech; Manassas, Va.) supplemented with 10% heat-inactivated fetal bovine serum, 2 mM glutamax and 1× penicillin/streptomycin. All cells were grown and maintained at 37° C. in a 5% CO2 incubator. SKBR3 were passaged by washing with calcium/magnesium-free Phosphate Balanced Saline (PBS) and harvested with HyQTase (Hyclone; Thermo Scientific; Waltham, Mass.).

Figure 8:
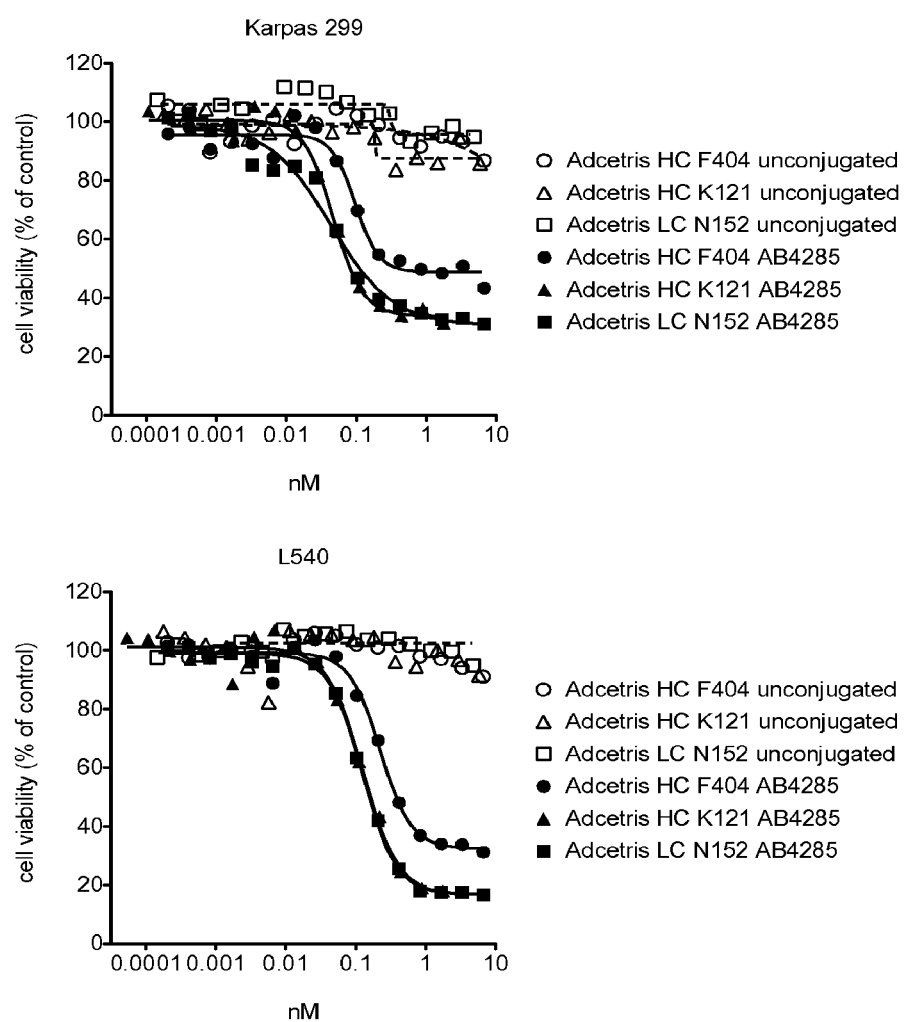
FIG. 8 depicts cell killing of CD-30 positive cell lines by exemplary brentuximab antibody-drug conjugates.
Figure 9:
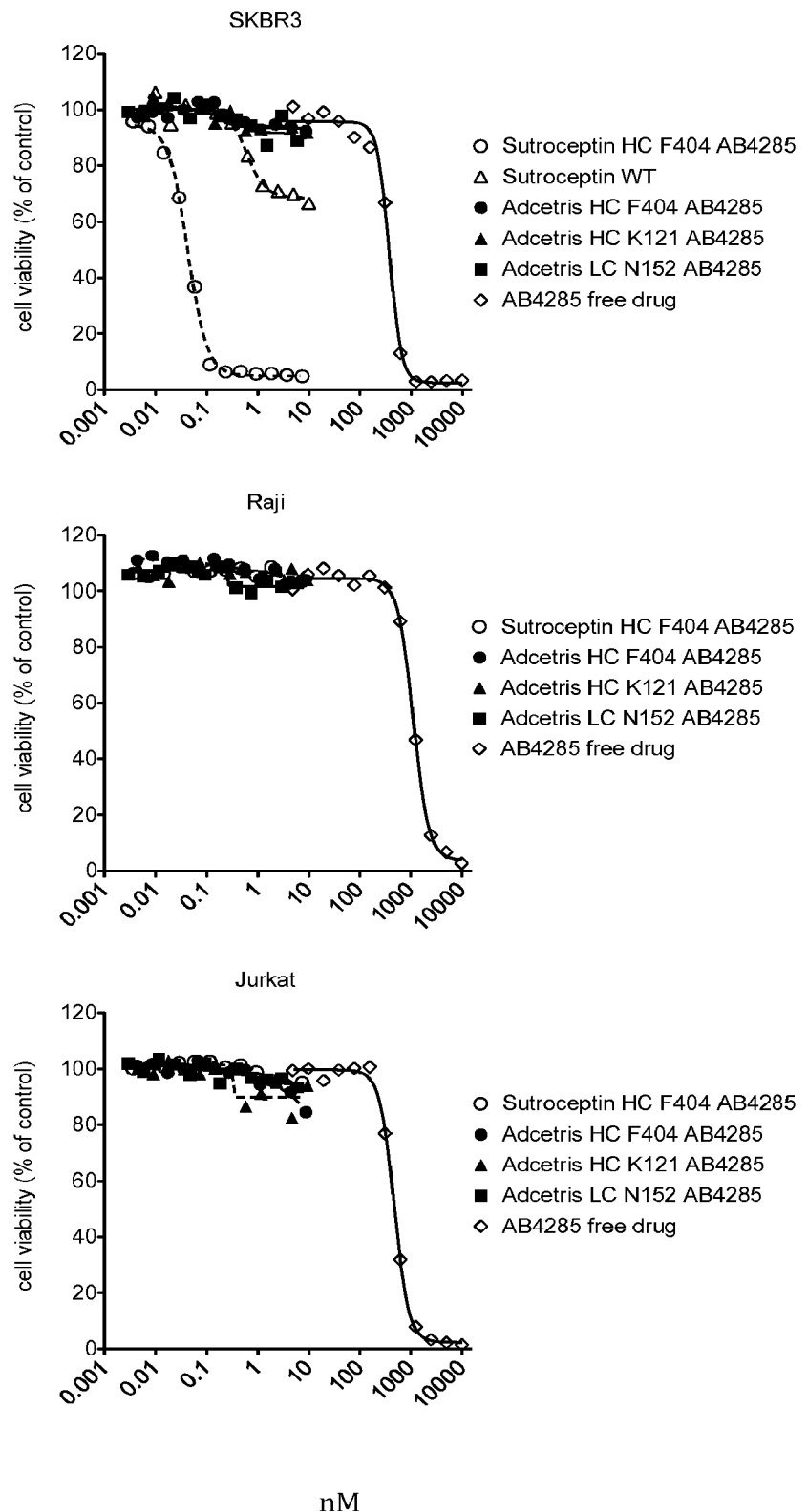
FIG. 9 provides experimental results demonstrating that exemplary brentuximab antibody-drug conjugates do not kill cells that do not express CD-30.

Cell killing activities of Trastuzumab and Brentuximab (ADCETRIS®) variants were measured using CellTiter-Glo® cell proliferation assay. Briefly, $10^4$ suspension cells or $3\times10^3$ SKBR3 cells were plated in 40 μl per well in a 96-well half-area white TC-treated plate and incubated at 37° C. for 2 hours prior to adding antibodies. Antibodies were formulated in the respective cell culture media and filter-sterilized with 0.45 μm celluloase acetate Costar Spin-X® centrifuge tube filters (Corning; Tewksbury, Mass.). 40 μl of unconjugated antibody, AB4285-conjugated antibody or AB4285 free drug were added to cells and cultured for either 3 days or 5 days for suspension cells and SKBR3 cells, respectively. Cell viability was measured by adding 80 μl of Cell Titer-Glo® reagent (Promega Corp.; Madison, Wis.) to each well and processed following product instructions. Luminescence was measured with the ENVISION® plate reader (Perkin-Elmer; Waltham, Mass.). Relative luminescence readings were converted to % viability using untreated cells as controls and plotted versus antibody concentration. IC50 was calculated from the non-linear regression equation, log (inhibitor) versus response—variable slope (4 parameters) using the statistical software, Prism (GraphPad Software; San Diego, Calif.). Results are shown in FIGS. 8 and 9 and Table 14.

TABLE 14

Cell Killing by Brentuximab and Trastuzumab Variants

| | | Cell Line | | |
|---|---|---|---|---|
| ADC | Site | Karpas IC50 (nM) | L540 IC50 (nM) | SKBR3 IC50 (nM) |
| Aglycosylated Brentuximab DBCO-MMAF 2 | HC F404 | .078 | .22 | |

TABLE 14-continued

Cell Killing by Brentuximab and Trastuzumab Variants

| ADC | Site | Karpas IC50 (nM) | L540 IC50 (nM) | SKBR3 IC50 (nM) |
|---|---|---|---|---|
| Aglycosylated Brentuximab DBCO-MMAF 2 | HC K121 | .040 | .12 | |
| Aglycosylated Brentuximab DBCO-MMAF 2 | LC N152 | .037 | .12 | |
| Aglycosylated Trastuzumab DBCO-MMAF 2 | HC F404 | | | .043 |
| free drug DBCO-MMAF 2 | | 43 | 46 | 78 |

Figure 10:
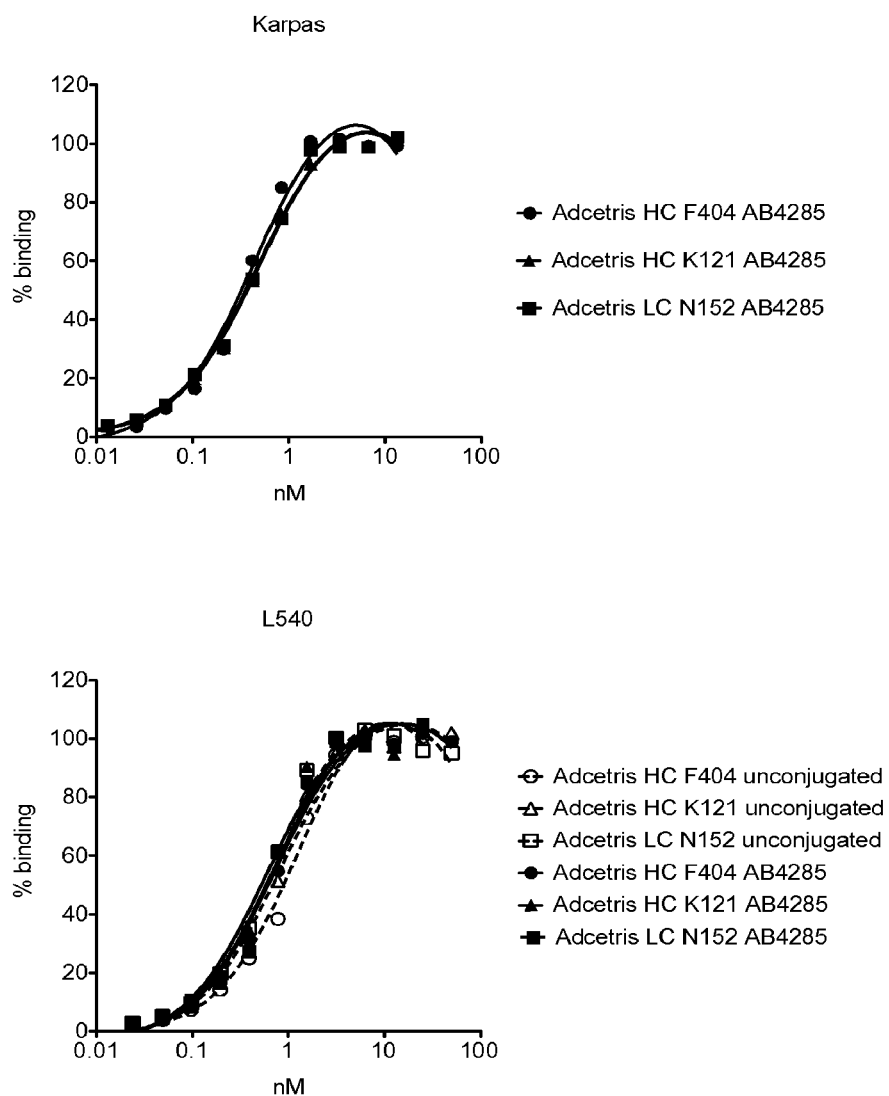
FIG. 10 depicts binding to CD-30 positive cell lines by exemplary brentuximab (ADCETRIS®) antibody-drug conjugates.

Cell binding affinities of trastuzumab and brentuximab variants were measured using a FACS-based assay. Briefly, 2×10$^5$ Karpas 299 or L540 cells in 25 μl of binding buffer, which consists of PBS containing 0.5% bovine serum albumin (BSA) (Invitrogen; Carlsbad, Calif.) and 0.09% sodium azide (Sigma; St. Louis, Mo.) were plated in a 96-well U-bottom polypropylene plate (Greiner Bio-One; Monroe, N.C.). Antibodies were formulated in binding buffer and 2-fold serial dilutions were prepared in a separate 96-well plate. Equal volume of diluted antibodies were added to cells and incubated at 4° C. for 1 hour. Cells were washed twice with 200 μl of binding buffer to remove unbound antibodies. For secondary antibody detection, 5 μg/ml Alexa-488 conjugated goat anti-human IgG (Invitrogen; Carlsbad, Calif.) was prepared in binding buffer and 50 μl was added to cells and incubated at 4° C. for 1 hour. Cells were washed twice, resuspended in 200 μl of binding buffer and analyzed using a BD FACScan® flow cytometer (Cytek; Fremont, Calif.) equipped with a 96-well automated microsampler (Cytek; Fremont, Calif.). Data was acquired and analyzed using FlowJo (Tree Star; Ashland, Oreg.). Mean fluorescence intensity readings were expressed as % binding by normalizing to averaged maximum MFI values and data was plotted versus antibody concentration. Binding affinities was calculated from the non-linear regression saturation binding equation, one site—total binding using Prism software. Results are shown in FIG. 10 and Table 15.

TABLE 15

Cell Binding of Brentuximab Variants

| ADC | Site | Karpas Kd (nM) | L540 Kd (nM) |
|---|---|---|---|
| Aglycosylated Brentuximab DBCO-MMAF 2 | HC F404 | .46 | .81 |
| Aglycosylated Brentuximab DBCO-MMAF 2 | HC K121 | .52 | .3 |
| Aglycosylated Brentuximab DBCO-MMAF 2 | LC N152 | .50 | .0 |

Example 14

Antibody-Drug Conjugates in Alternative Scaffolds: scFv Formats

To demonstrate the feasibility of using scFv as alternative scaffold for ADC, DNA encoding trastuzumab scFv (VL_VH) with an amber codon was cloned into expression vector pYD317. The TAG codon was inserted by overlapping PCR mutagenesis at the nucleotides corresponding to the amino acid serine at the position (−1).

To express the scFv, cell-free extracts were thawed to room temperature and incubated with 50 uM iodoacetamide for 30 min. Cell-free reactions were run at 30 C for up to 10 h containing 30% (v/v) iodoacetamide-treated extract with 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids for all 18 amino acids except tyrosine and phenylalanine which were added at 0.5 mM, 4 mM sodium oxalate, 1 mM putrescine, 1.5 mM spermidine, 15 mM potassium phosphate, 100 nM T7 RNAP, 1.3 uM E. coli DsbC, 2 mM oxidized (GSSG) glutathione, 10 ug/mL scFv plasmid 15 uM in vivo produced m.j. tRNA, 5 uM m.j RNA synthetase and 1 mM pAzido Phenylanine (pN3F). Wild type scFv was expressed as control.

scFv(−1)pN3F and wild type scFv were purified by Protein L followed by SEC. 5 uM scFv (−1) was incubated with 50 uM of the DBCO-MMAF reagent shown in FIG. 1 for 16 hours at room temperature. The excess free drug was removed by zeba desalting column.

Hydrophobic Interaction Chromatography was then performed to quantitate the samples and to determine the drug-antibody ratios as follows. Samples and standards were diluted 1:1 in 3M Ammonium Sulfate (EMD Chemical), 50 mM Sodium Phosphate pH 7.0 (Mallinckrodt) prepared in MilliQ water. A Dionex HPLC system was equipped with a Tosoh Bioscience LLC TSK-gel Butyl-NPR® (4.6 mm×3.5 cm) column with a column compartment temperature of 30° C. The mobile phase A was 1.5M Ammonium Sulfate, 50 mM Sodium Phosphate, pH 7.0. The mobile phase B was 50 mM Sodium Phosphate, pH 7.0 in 80:20 water:isopropyl Alcohol (Honeywell). The mobile phase was delivered at a flow rate of 1.0 mL/minute. The separation was performed with a linear gradient of 15% mobile phase B to 100% mobile phase B in 10 minutes. The UV data was acquired at 214 nm. The peak areas were quantitated using Chromeleon software (Thermo) to calculate Drug Antibody Ratio (DAR).

To assess binding of the conjugated alternative scaffold variants, a binding assay to cells expressing HER2 was performed as follows. The binding of the purified conjugated variants to HER2 on SKBR3 cells, which overexpress the HER2/c-erb-2 gene product, with over 1.5 million receptor copies per cell (ATCC # HTB-30, Manassas, Va.) was compared to clinical grade Herceptin®, unglycosylated trastuzumab produced by cell-free protein synthesis, or human serum IgG1 as a negative control (Sigma-Aldrich; St. Louis, Mo.). SKBR3 cells were cultured in DMEM:Ham's F-12 (50:50), high glucose (Cellgro-Mediatech; Manassas, Va.) supplemented with 10% heat-inactivated fetal bovine serum (Hyclone; Thermo Scientific; Waltham, Mass.), 2 mM glutamax (Invitrogen; Carlsbad, Calif.) and 1× Penicillin/streptomycin (Cellgro-Mediatech; Manassas, Va.). Adherent cells were washed twice with calcium and magnesium-free Hanks Balanced Salt Solution (HBSS), harvested with HYQ®TASE™ (Hyclone; Thermo Scientific; Waltham, Mass.). A total of 200,000 cells per sample in total volume of 10 μL were incubated with serial dilutions of either conjugated alternative scaffold variants, clinical grade HERCEPTIN®, or aglycosylated trastuzumab made in 10 μL FACS buffer (DPBS buffer supplemented with 1% bovine serum albumin). Cells plus antibody or ADC were incubated for 60 minutes on ice. Unstained cells, human IgG1 (Isotype control) and Secondary antibody (goat anti-human IgG)

were used as controls. To detect HERCEPTIN® or aglycosylated trastuzumab binding, cells were washed twice with ice-cold FACS buffer and incubated with 5 µg/ml Alexa 647 labeled goat anti-human IgG secondary antibody (Invitrogen; Carlsbad, Calif.) on ice for 1 hour. Alternative scaffold variant cell binding was detected by incubating cells on ice for 1 h with either 5 µg/ml Alexa 647 labeled Protein L (Pierce) or goat anti-human-Fc labeled with Alexa 647 (Invitrogen; Carlsbad, Calif.). All samples were washed using FACS buffer and analyzed using a BD FACS Calibur system (BD Biosciences; San Jose, Calif.).

Mean fluorescence intensities were fitted using non-linear regression analysis with one site specific binding equation using GraphPad Prism (GraphPad v 5.00, Software; San Diego, Calif.). Data was expressed as Relative MFI vs. concentration of antibody or antibody variant in nM.

Next, the effects of the conjugated alternative scaffold variants on cell killing were measured with a cell proliferation assay as follows. SKBR3 cells were obtained from ATCC and maintained in DMEM:Ham's F-12 (50:50), high glucose (Cellgro-Mediatech; Manassas, Va.) supplemented with 10% heat-inactivated fetal bovine serum (Hyclone; Thermo Scientific; Waltham, Mass.), 2 mM glutamax (Invitrogen; Carlsbad, Calif.) and 1× Penicillin/streptomycin (Cellgro-Mediatech; Manassas, Va.). Adherent cells were washed twice with calcium and magnesium-free Hanks Balanced Salt Solution (HBSS), harvested with HYQ®TASE™ (Hyclone; Thermo Scientific; Waltham, Mass.). A total of $10^3$ cells were seeded in a volume of 40 µl in a 96-well half area flat bottom white Polystyrene plate. The cells were allowed to adhere overnight at 37° C. in a $CO_2$ incubator. ADC variants were formulated at 2× concentration in DMEM/F12 medium and filtered through MultiScreen$_{HTS}$ 96-Well Filter Plates (Millipore; Billerica, Mass.). Filter sterilized conjugated alternative scaffold variants, HERCEPTIN®, or aglycoslyated trastuzumab were added into treatment wells and plates were cultured at 37° C. in a CO2 incubator for 120 hrs. For cell viability measurement, 80 µl of Cell Titer-Glo® reagent (Promega Corp.; Madison, Wis.) was added into each well, and plates processed as per product instructions. Relative luminescence was measured on an ENVISION® plate reader (Perkin-Elmer; Waltham, Mass.). Relative luminescence readings were converted to % viability using untreated cells as controls. Data was fitted with non-linear regression analysis, using log(inhibitor) vs. response—Variable slope, 4 parameter fit equation using GraphPad Prism (GraphPad v 5.00, Software; San Diego, Calif.). Data was expressed as relative cell viability, ATP content % vs. dose of ADC in nM.

Results from the HIC analysis, the cell binding, and cell killing experiments are presented in Table 16.

TABLE 16 scFv Cell Binding, Cell Killing, and DAR

| Scaffold | SKBR3 Cell Binding IC50, nM | SKBR3 Cell Killing Kd, nM | DAR by HIC Assay |
|---|---|---|---|
| Unglycosylated Trastuzumab | 5 | NA | NA |
| scFv(−1) WT | 15 | NA | NA |
| scFv(−1) conjugate | 14 | 0.48 | 0.77 |

Example 15

Antibody-Drug Conjugates In Alternative Scaffolds: Scfv-Fc Formats

To demonstrate the feasibility of using scFv Fc as alternative scaffold for ADC, DNA encoding trastuzumab scFv Fc (VL_VH_Fc) with amber was cloned into expression vector pYD317. TAG codon was inserted by overlapping PCR mutagenesis at the nucleotides corresponding to the amino acid serine at the position (−1), Fc R355, Fc N389, and Fc F404 (EU index numbering).

CFPS reaction conditions were same as described in Example 14, except that 5 uM yeast PDI was added. Wild type scFv Fc was expressed as control.

To conjugate aglycosylated scFv-Fc, proteins were first purified by Protein A followed by SEC. 5 uM pN3F containing scFv-Fc was incubated with 50 uM DBCO-MMAF for 16 hours at room temperature. The excess free drug was removed by zeba desalting column.

Figure 11:
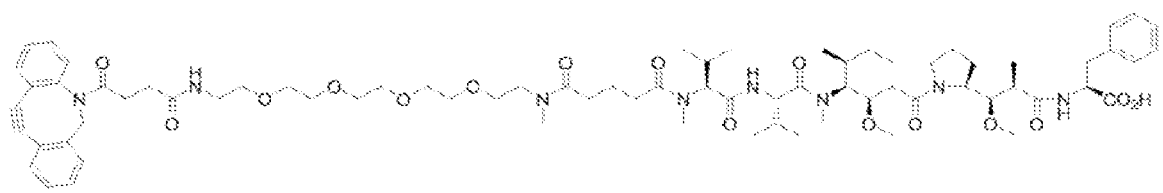
FIGS. 11A, 11B, 11C, and 11D provide the structure of exemplary cytotoxic reagents DBCO-MMAF 2, DBCO-DM4, DBCO-DM4 2, and DBCO-MMAE, respectively.
Figure 11:
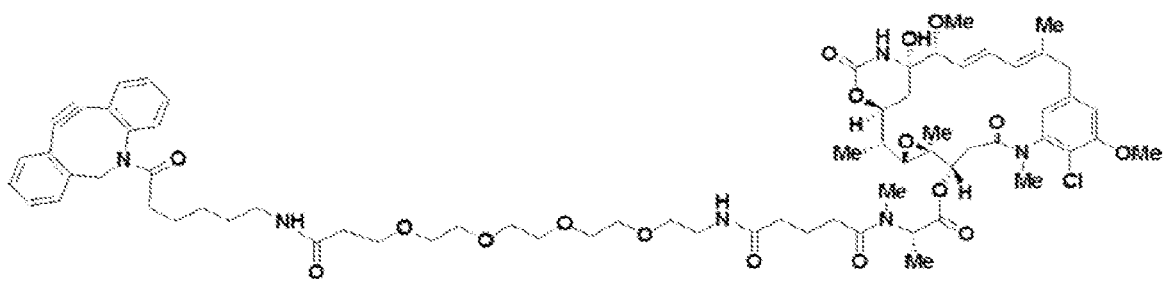
Figure 11:
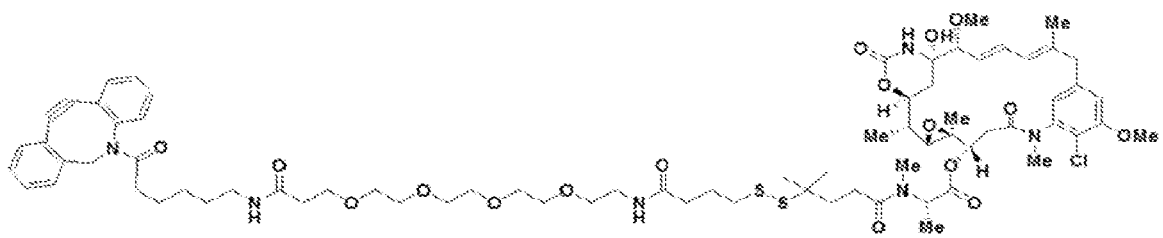
Figure 11:
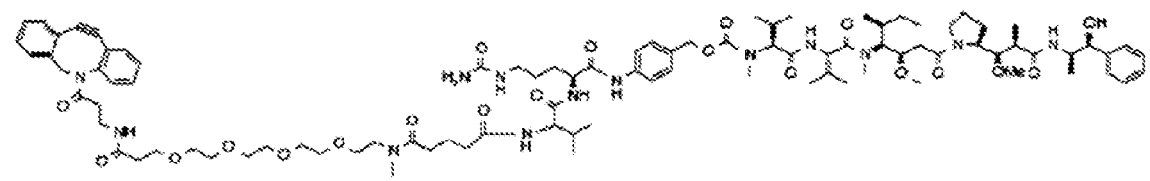

Additionally, pAzido Methyl Phenylanine was incorporated to scFv Fc at the sites of R355, N389, and F404, respectively. The reaction condition was same as described in Example 14, except that 1 uM m.j. pCyano FRS and 1 mM pAzido Methyl Phe were used to replace the pair of m.j. FRS and pAzdio Phe. The protein A purified protein was then conjugated with DBCO-MMAF reagent 2 (DBCO-MMAF 2). The structure of DBCO-MMAF 2 is shown in FIG. 11.

Next, LC-MS was performed to quantitate the samples and to determine the drug-antibody ratios as follows. Samples were analyzed by liquid chromatography (CHIP-Cube nanoLC, Agilent) coupled to a qTOF mass spectrometer (Agilent 6520). Proteins were separated on a reverse phase HPLC-Chip (PLRP-S, 4000 Å, 5µ; Enrichment column: 25 mm; Separation column: 150 mm×75 µm) with 0.1% formic acid in water (solvent A) and 0.1% formic acid in acetonitrile+isopropyl alcohol (80:20 v/v, solvent B). Data was processed using MassHunter Qualitative Software (Agilent). Data is shown in Table 17.

TABLE 17

DAR and Cell Binding and Killing of scFv-Fc variants

| Scaffold | SKBR3 Cell Binding Kd, nM | SKBR3 Cell Killing IC50, nM | DAR by LCMS DAR |
|---|---|---|---|
| Herceptin ® | 12 | NA | NA |
| Aglycosylated Trastuzumab | 8.1 | NA | NA |
| Her scFv-Fc | 6.0 | NA | NA |
| scFv-Fc (−1) pN$_3$F DBCO-MMAF | 6.8 | 0.011 | 1.86 |
| scFv-Fc (R355) pN$_3$F DBCO-MMAF | 6.9 | 0.015 | 1.77 |
| scFv-Fc (N389) pN$_3$F DBCO-MMAF | 5.4 | 0.010 | 1.53 |
| scFv-Fc (N389) pN$_3$CH$_2$F DBCO-MMAF 2 | 3.0 | | 1.97 |
| scFv-Fc (R355) pN$_3$CH$_2$F DBCO-MMAF 2 | 5.0 | 0.055 | 1.97 |
| scFv-Fc (F404) vH-vL pN3CH2 F DBCO-MMAF 2 | | 0.05 | 1.99 |
| scFv-Fc (F404) vL-vLH pN3CH2 F DBCO-MMAF 2 | | 0.068 | 1.97 |

In vivo stability of drug linker ADC conjugates was measured by dosing 2 mg/kg of respective scFv-Fc DBCO-MMAF 2 conjugates into Beige nude Xid mice. Plasma was collected by terminal bleeds at 30 mins, d3, d7, d14 and d21 from n=2 animals for each time point. Total circulating ScFv-FC ADCs were captured by Biotin-(Fab)2 Goat Anti-Human IgG, Fcγ fragment specific. Complex was pulled down with streptavidin Mag Sepharose. Captured complex was washed to remove nonspecific binding and eluted with 1% formic acid. Neutralized eluate was analyzed by intact LCMS. The results indicate that scFv-Fc (N389) pN$_3$CH$_2$F DBCO-MMAF 2 and scFv-Fc (R355) pN$_3$CH$_2$ F DBCO-MMAF 2 are stable up to 28 days.

Figure 12:
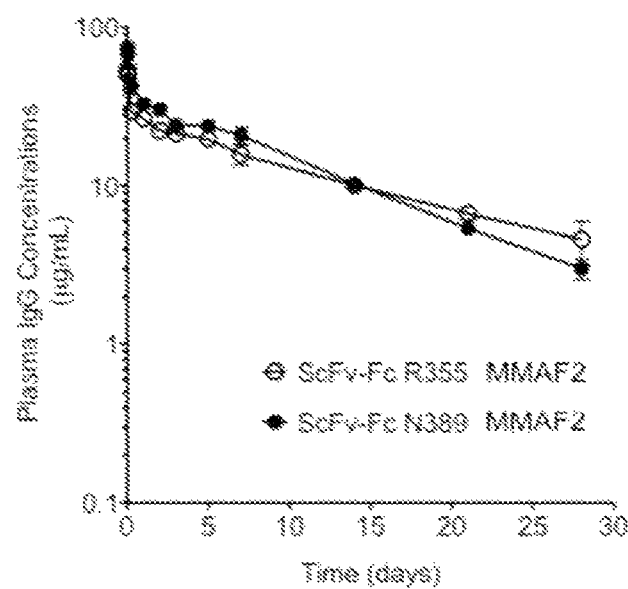
FIG. 12 provides a graphical representation of the pharmacokinetics of an exemplary scFv-Fc site-specific antibody-drug conjugate.
Figure 13A:
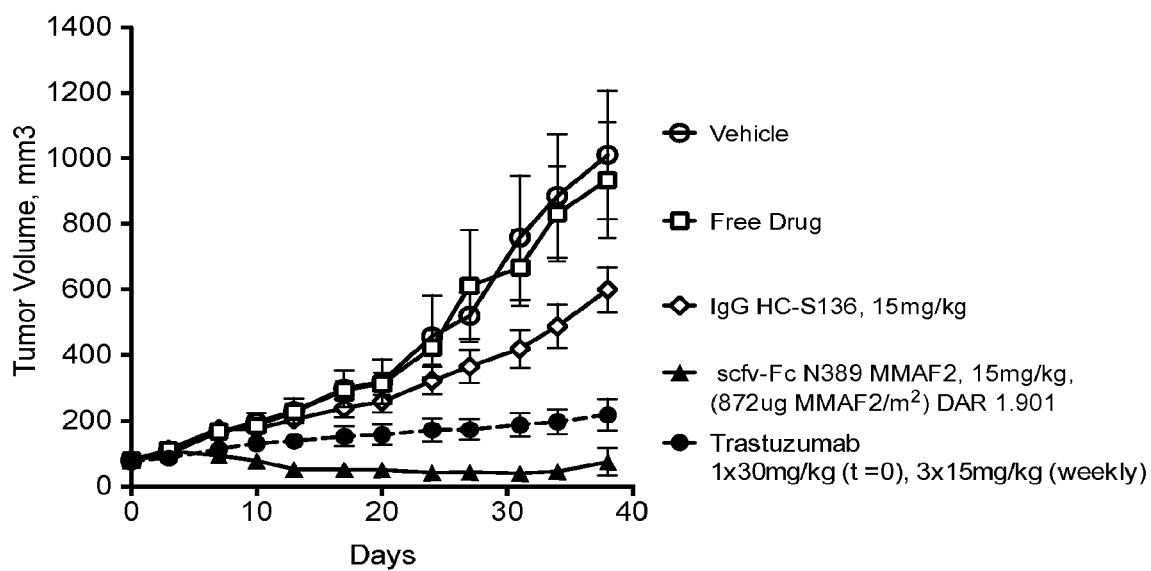
FIGS. 13A and 13B depict a graphical representation of the in vivo effectiveness of exemplary site-specific antibody-drug conjugates to retard tumor growth and/or to regress tumor size in an animal model.
Figure 13B:
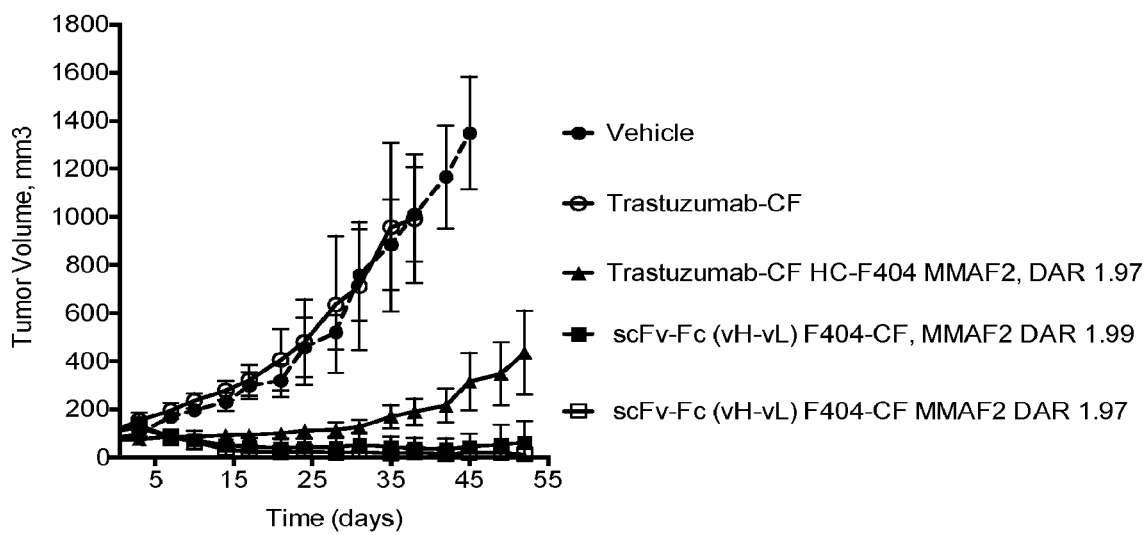

Next, pharmacokinetics properties of ScFv-Fc ADCs were analyzed in beige nude xid mice. Animals were dosed intravenously at a dose level of approximately of 2.0 mg/kg of scFv-Fc R355 and scFv-Fc N389. The plasma concentrations, sampled out to 28 days, were determined by immunoassay and the pharmacokinetic parameters calculated using a non-compartmental approach with WinNonlin 'v' 5.2 (Pharsight, Calif.). Results are shown in FIG. 12.

To assess in vivo efficacy of the scFc-Fc ADCs, KPL-4 human breast tumor cells were inoculated into the mammary fat pads of SCID beige mice (Charles River Laboratories). A total of 3 million cells per mouse, suspended in 50% phenol red-free Matrigel (Becton Dickinson Bioscience) mixed with culture medium were injected. Once tumor size was reached all animals were randomly assigned into treatment groups, such that the mean tumor volume for each group was 100-150 mm$^3$.

Trastuzumab (30 mg/kg) was given i.p. (single injection on treatment day 0), followed by (15 mg/kg) per week for 3 weeks. Aglycosylated Trastuzumab 2nnAA variant scFv-Fc N389 DBCO-MMAF 2 15 mg/kg (872 ug MMAF/m2, DAR 1.901), Aglycosylated Trastuzumab 2nnAA variant HC-S136 (15 mg/kg) (unconjugated) Vehicle (PBS) and free drug (0.54 mg/kg) were given via i.v (single injection on treatment day 0). The results of this experiment are presented in FIG. 13a.

In another experiment, scFv-Fc F404 vL-vH DBCO-MMAF 2 (15 mg/kg), scFv-Fc F404 vH-vL DBCO-MMAF 2 (15 mg/kg), Trastuzumab-CF HC F404 DBCO-MMAF 2 (15 mg/kg), Trastuzumab-CF (15 mg/kg), and vehicle were administered by single i.v. injection on day 0. The results of this experiment are presented in FIG. 13b.

For both experiments, all treatment groups consisted of 10 animals per group, and tumor size was monitored twice weekly using caliper measurement. Mice were housed in standard rodent microisolator cages. Environmental controls for the animal rooms were set to maintain a temperature of 70° F., a relative humidity of 40% to 60%, and an approximate 14-h light/10-h dark cycle.

The results of this experiment demonstrate that the ADCs conjugated at positions N389 and F404 were effective in an animal to durably regress tumor size. Of particular note, the F404 scFv-Fc conjugates achieved regression below baseline, demonstrating particular efficacy for this scaffold in a solid tumor model.

Example 16

Exemplary Adcs Specific For Cd74 And Her2 And With Additional Exemplary Linker-Warhead Combinations This example provides exemplary antibody-drug conjugates prepared with an antibody specific for CD74 and containing different exemplary linker-warhead combinations as described herein. This example further provides exemplary antibody-drug conjugates prepared from trastuzumab conjugated with certain of the linker-warhead combinations.

The protein sequence of the heavy and light chains of the anti-CD74 antibody used in this example are provided as SEQ ID NO:5 and 6, respectively. The heavy chain sequence includes a 6-His C-terminal tag to assist with puridication. Amber codons at the positions encoding HC K212, HC S136, HC F241, HC F404, LCS7, or LC N152 were introduced using the methods described in Example 13. Anti-CD74 antibodies containing p-methylazido-Phe were expressed and purified using the methods described in Example 13. Trastuzumab variants containing p-methyl-azido-Phe at positions HC S136 or HC F404 were also expressed and purified as described in Example 13.

Next, the anti-CD74 or trastuzumab variants were conjugated with DBCO-MMAF 2 (FIG. 11A), DBCO-DM4 (FIG. 11B), DBCO-DM4 2 (FIG. 11C), or DBCO-MMAE (FIG. 11D). The method used to perform the conjugation reactions between the antibody variants and the linker-warhead combinations was as described in Example 13.

The drug-antibody ratios (DARs) of the ADCs was then determined by LC-MS according to the method described in Example 13. It should be noted that the LC-MS method for the anti-CD74 samples had not been optimized for this antibody; the results of the analysis contained peaks overlapping with unconjugated species, artificially lowering the DAR of these samples. The DAR of the ADC variants prepared in this example therefore showed good agreement with the ADCs containing a nnAA at corresponding sites discussed in Examples 1-15. Results of the DAR analysis are presented in Table 18, below.

Next, the ADC variants were used in cell killing experiments to determine their IC$_{50}$ values. Trastuzumab variants were analyzed as described in Example 13. The effects of the conjugated anti-CD74 variants on cell killing were measured by a cell proliferation assay. SU-DHL-6 and NCI-H929 cells were obtained from ATCC and maintained in RPMI-1640 medium (Cellgro-Mediatech; Manassas, Va.) supplemented with 20% heat-inactivated fetal bovine serum (Hyclone; Thermo Scientific; Waltham, Mass.), 2 mM glutamax (Invitrogen; Carlsbad, Calif.) and 1× Penicillin/streptomycin (Cellgro-Mediatech; Manassas, Va.). SU-DHL-6 and NCI-H929 cells were harvested and re-suspended in culture medium at final concentration of 0.5×10$^6$ cells/mL. A total of 20×10$^3$ cells in a volume of 40 µl were seeded in each well of a 96-well half area flat bottom white polystyrene plate. ADC variants were formulated at 2× concentration in RPMI-1640 complete medium and filtered through MultiScreen$_{HTS}$ 96-Well Filter Plates (Millipore; Billerica, Mass.). Filter sterilized ADCs were added into treatment wells and plates were cultured at 37° C. in a CO$_2$ incubator for 72 hrs. For cell viability measurement, 80 µl of Cell Titer-Glo® reagent (Promega Corp. Madison, Wis.) was added into each well, and plates were processed as per product instructions. Relative luminescence was measured on an ENVISION® plate reader (Perkin-Elmer; Waltham, Mass.). Relative luminescence readings were converted to % viability using untreated cells as controls. Data was fitted with non-linear regression analysis, using log(inhibitor) vs. response—variable slope, 4 parameter fit equation using GraphPad Prism (GraphPad v 5.00, Software; San Diego, Calif.). Data was expressed as relative cell viability, ATP content % vs. dose of ADC in nM. Results of the cell killing assays are presented in Table 18.

TABLE 18

DAR and IC$_{50}$ Values for Exemplary Anti-CD74 and Anti-HER2 ADCs

| Antibody | Drug Conjugate | Site | DAR | IC$_{50}$ |
| --- | --- | --- | --- | --- |
| Anti-CD74 Antibody | DBCO-MMAF 2 | HC K121 | 1.601 | 0.122 |
| Anti-CD74 Antibody | DBCO-MMAF 2 | HC S136 | 1.601 | 0.100 |
| Anti-CD74 Antibody | DBCO-MMAF 2 | HC F241 | 1.58 | 0.078 |
| Anti-CD74 Antibody | DBCO-MMAF 2 | HC F404 | 1.631 | 0.137 |
| Anti-CD74 Antibody | DBCO-MMAF 2 | LC S7 | 1.543 | 0.120 |

TABLE 18-continued

DAR and IC$_{50}$ Values for Exemplary
Anti-CD74 and Anti-HER2 ADCs

| Antibody | Drug Conjugate | Site | DAR | IC$_{50}$ |
|---|---|---|---|---|
| Anti-CD74 Antibody | DBCO-MMAF 2 | LC N152 | 1.457 | 0.130 |
| Anti-CD74 Antibody | DBCO-DM4 | HC K121 | 1.572 | 0.191 |
| Anti-CD74 Antibody | DBCO-DM4 | HC S136 | 1.61 | 0.271 |
| Anti-CD74 Antibody | DBCO-DM4 | HC F241 | 1.581 | 0.187 |
| Anti-CD74 Antibody | DBCO-DM4 | HC F404 | 1.531 | 0.253 |
| Anti-CD74 Antibody | DBCO-DM4 | LC S7 | 1.509 | 0.293 |
| Anti-CD74 Antibody | DBCO-DM4 | LC N152 | 1.474 | 0.281 |
| Anti-CD74 Antibody | DBCO-DM4 2 | HC K121 | 1.578 | 0.215 |
| Anti-CD74 Antibody | DBCO-DM4 2 | HC S136 | 1.589 | 0.215 |
| Anti-CD74 Antibody | DBCO-DM4 2 | HC F241 | 1.612 | 0.196 |
| Anti-CD74 Antibody | DBCO-DM4 2 | HC F404 | 1.63 | 0.154 |
| Anti-CD74 Antibody | DBCO-DM4 2 | LC S7 | 1.561 | 0.291 |
| Anti-CD74 Antibody | DBCO-DM4 2 | LC N152 | 1.495 | 0.235 |
| Anti-CD74 Antibody | DBCO-MMAE | HC K121 | 1.811 | 0.166 |
| Anti-CD74 Antibody | DBCO-MMAE | HC S136 | 1.752 | 0.242 |
| Anti-CD74 Antibody | DBCO-MMAE | HC F241 | 1.81 | 0.238 |
| Anti-CD74 Antibody | DBCO-MMAE | HC F404 | 1.572 | 0.235 |
| Anti-CD74 Antibody | DBCO-MMAE | LC S7 | 1.581 | 0.224 |
| Anti-CD74 Antibody | DBCO-MMAE | LC N152 | 1.616 | 0.251 |
| Trastuzumab | DBCO-DM4 | HC F404 | 0.036 | 1.84 |
| Trastuzumab | DBCO-DM4 | HC S136 | 0.038 | 1.82 |
| Trastuzumab | DBCO-DM4 2 | HC F404 | 0.043 | 1.94 |
| Trastuzumab | DBCO-DM4 2 | HC S136 | 0.038 | 1.82 |

Example 17 further demonstrates that the site of incorporation of a nnAA into an antibody can transfer reasonably predictably between antibodies. Further, the identity of the linker and warhead does not appear to significantly affect the conjugation efficiency or DAR of the resulting ADC, demonstrating reasonable predictability that a given warhead-linker combination can be conjugated to the an antibody containing a non-natural amino acid at one of the preferred sites.

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

```
                        Sequence Listing

<210> SEQ ID NO 1
<211> LENGTH: 449
<212> TYPE: PRT
<213> ORGANISM: Artificial sequence
<220> FEATURE:
<223> OTHER INFORMATION: sequence is synthesized
<400> SEQUENCE: 1
Glu Val Gln Leu Val Glu Ser Gly Gly Gly Leu Val Gln Pro Gly
 1               5                  10                  15
Gly Ser Leu Arg Leu Ser Cys Ala Ala Ser Gly Phe Asn Ile Lys
                20                  25                  30
Asp Thr Tyr Ile His Trp Val Arg Gln Ala Pro Gly Lys Gly Leu
                35                  40                  45
Glu Trp Val Ala Arg Ile Tyr Pro Thr Asn Gly Tyr Thr Arg Tyr
                50                  55                  60
Ala Asp Ser Val Lys Gly Arg Phe Thr Ile Ser Ala Asp Thr Ser
                65                  70                  75
Lys Asn Thr Ala Tyr Leu Gln Met Asn Ser Leu Arg Ala Glu Asp
                80                  85                  90
Thr Ala Val Tyr Tyr Cys Ser Arg Trp Gly Gly Asp Gly Phe Tyr
                95                 100                 105
Ala Met Asp Tyr Trp Gly Gln Gly Thr Leu Val Thr Val Ser Ser
               110                 115                 120
Ala Ser Thr Lys Gly Pro Ser Val Phe Pro Leu Ala Pro Ser Ser
               125                 130                 135
Lys Ser Thr Ser Gly Gly Thr Ala Ala Leu Gly Cys Leu Val Lys
               140                 145                 150
Asp Tyr Phe Pro Glu Pro Val Thr Val Ser Trp Asn Ser Gly Ala
               155                 160                 165
Leu Thr Ser Gly Val His Thr Phe Pro Ala Val Leu Gln Ser Ser
               170                 175                 180
Gly Leu Tyr Ser Leu Ser Ser Val Val Thr Val Pro Ser Ser Ser
               185                 190                 195
Leu Gly Thr Gln Thr Tyr Ile Cys Asn Val Asn His Lys Pro Ser
               200                 205                 210
Asn Thr Lys Val Asp Lys Lys Val Glu Pro Lys Ser Cys Asp Lys
               215                 220                 225
Thr His Thr Cys Pro Pro Cys Pro Ala Pro Glu Leu Leu Gly Gly
               230                 235                 240
Pro Ser Val Phe Leu Phe Pro Pro Lys Pro Lys Asp Thr Leu Met
               245                 250                 255
Ile Ser Arg Thr Pro Glu Val Thr Cys Val Val Val Asp Val Ser
               260                 265                 270
His Glu Asp Pro Glu Val Lys Phe Asn Trp Tyr Val Asp Gly Val
               275                 280                 285
```

| Sequence Listing |
| --- |

```
Glu Val His Asn Ala Lys Thr Lys Pro Arg Glu Glu Gln Tyr Asn
            290                 295                 300
Ser Thr Tyr Arg Val Ser Val Leu Thr Val Leu His Gln Asp
        305                 310                 315
Trp Leu Asn Gly Lys Glu Tyr Lys Cys Lys Val Ser Asn Lys Ala
            320                 325                 330
Leu Pro Ala Pro Ile Glu Lys Thr Ile Ser Lys Ala Lys Gly Gln
            335                 340                 345
Pro Arg Glu Pro Gln Val Tyr Thr Leu Pro Pro Ser Arg Glu Glu
            350                 355                 360
Met Thr Lys Asn Gln Val Ser Leu Thr Cys Leu Val Lys Gly Phe
            365                 370                 375
Tyr Pro Ser Asp Ile Ala Val Glu Trp Glu Ser Asn Gly Gln Pro
            380                 385                 390
Glu Asn Asn Tyr Lys Thr Thr Pro Pro Val Leu Asp Ser Asp Gly
            395                 400                 405
Ser Phe Phe Leu Tyr Ser Lys Leu Thr Val Asp Lys Ser Arg Trp
            410                 415                 420
Gln Gln Gly Asn Val Phe Ser Cys Ser Val Met His Glu Ala Leu
            425                 430                 435
His Asn His Tyr Thr Gln Lys Ser Leu Ser Leu Ser Pro Gly
            440                 445

<210> SEQ ID NO 2
<211> LENGTH: 214
<212> TYPE: PRT
<213> ORGANISM: Artificial sequence
<220> FEATURE:
<223> OTHER INFORMATION: Sequence is synthesized.
<400> SEQUENCE: 2
Asp Ile Gln Met Thr Gln Ser Pro Ser Ser Leu Ser Ala Ser Val
 1               5                  10                  15
Gly Asp Arg Val Thr Ile Thr Cys Arg Ala Ser Gln Asp Val Asn
            20                  25                  30
Thr Ala Val Ala Trp Tyr Gln Gln Lys Pro Gly Lys Ala Pro Lys
            35                  40                  45
Leu Leu Ile Tyr Ser Ala Ser Phe Leu Tyr Ser Gly Val Pro Ser
            50                  55                  60
Arg Phe Ser Gly Ser Arg Ser Gly Thr Asp Phe Thr Leu Thr Ile
            65                  70                  75
Ser Ser Leu Gln Pro Glu Asp Phe Ala Thr Tyr Tyr Cys Gln Gln
            80                  85                  90
His Tyr Thr Thr Pro Pro Thr Phe Gly Gln Gly Thr Lys Val Glu
            95                  100                 105
Ile Lys Arg Thr Val Ala Ala Pro Ser Val Phe Ile Phe Pro Pro
            110                 115                 120
Ser Asp Glu Gln Leu Lys Ser Gly Thr Ala Ser Val Val Cys Leu
            125                 130                 135
Leu Asn Asn Phe Tyr Pro Arg Glu Ala Lys Val Gln Trp Lys Val
            140                 145                 150
Asp Asn Ala Leu Gln Ser Gly Asn Ser Gln Glu Ser Val Thr Glu
            155                 160                 165
Gln Asp Ser Lys Asp Ser Thr Tyr Ser Leu Ser Ser Thr Leu Thr
            170                 175                 180
Leu Ser Lys Ala Asp Tyr Glu Lys His Lys Val Tyr Ala Cys Glu
            185                 190                 195
Val Thr His Gln Gly Leu Ser Ser Pro Val Thr Lys Ser Phe Asn
            200                 205                 210
Arg Gly Glu Cys SEQ ID NO 3
> Sequence of brentuximab heavy chain: HC-6His
MQIQLQQSGPEVVKPGASVKISCKASGYTFTDYYITWVKQKPGQGLEWIGWIYPGSGNTKYNEKFKGKAT
LTVDTSSSTAFMQLSSLTSEDTAVYFCANYGNYWFAYWGQGTQVTVSAASTKGPSVFPLAPSSKSTSGGT
AALGCLVKDYFPEPVTVSWNSGALTSGVHTFPAVLQSSGLYSLSSVVTVPSSSLGTQTYICNVNHKPSNT
KVDKKVEPKSCDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLYSKLTVDKSRWQQ
GNVFSCSVMHEALHNHYTQKSLSLSPGKGGSHHHHHH SEQ ID NO 4
> Sequence of brentuximab light chain: LC
MDIVLTQSPASLAVSLGQRATISCKASQSVDFDGDSYMNWYQQKPGQPPKVLIYAASNLESGIPARFSGS
GSGTDFTLNIHPVEEEDAATYYCQQSNEDPWTFGGGTKLEIKRTVAAPSVFIFPPSDEQLKSGTASVVCL
LNNFYPREAKVQWKVDNALQSGNSQESVTEQDSKDSTYSLSSTLTLSKADYEKHKVYACEVTHQGLSSPV
TKSFNRGEC
```

| Sequence Listing |
|---|
| SEQ ID NO 5<br>>Sequence of anti-CD74 heavy chain: HC<br>M Q V Q L V E S G G G V V Q P G R S L R L S C A A S G F T F S S Y G M<br>H W V R Q A P D K G L E W V A V I W Y D G S N K Y Y A D S V K G R F T<br>I S R D N S K N T L Y L Q M N S L R A E D T A V Y Y C A R G G T L V R<br>G A M Y G T D V W G Q G T T V T V S S A S T K G P S V F P L A P S S K<br>S T S G G T A A L G C L V K D Y F E E P V T V S W N S G A L T S G V H<br>T F P A V L Q S S G L Y S L S S V V T V P S S S L G T Q T Y I C N V N<br>H K P S N T K V D K K V E P K S C D K T H T C P P C P A P E L L G G P<br>S V F L F P P K P K D T L M I S R T P E V T C V V V D V S H E D P E V<br>K F N W Y V D G V E V H N A K T K P R E E Q Y N S T Y R V V S V L T V<br>L H Q D W L N G K E Y K C K V S N K A L P A P I E K T I S K A K G Q P<br>R E P Q V Y T L P P S R E E M T K N Q V S L T C L V K G F Y P S D I A<br>V E W E S N G Q P E N N Y K T T P P V L D S D G S F F L Y S K L T V D<br>K S P W Q Q G N V F S C S V M H E A L H N H Y T Q K S L S L S P G K G<br>G S H H H H E H<br><br>SEQ ID NO 6<br>>Sequence of anti-CD74 light chain<br>M D I Q M T Q S D S S L S A S V G D R V T I T C R A S Q G I S S W L A<br>W Y Q Q K P E K A P K S L I Y A A S S L Q S G V P S R F S G S G S G T<br>D F T L T I S S L Q P E D F A T Y Y C Q Q Y N S Y P L T F G G G T K V<br>E I K R T V A A P S V F I F P P S D E Q L K S G T A S V V C L L N N F<br>Y P R E A K V Q W K V D N A L Q S G N S Q E S V T E Q D S K D S T Y S<br>L S S T L T L S K A D Y E K H K V Y A C E V T H Q G L S S P V T K S F<br>N R G E C |

SEQUENCE LISTING

<160> NUMBER OF SEQ ID NOS: 8

<210> SEQ ID NO 1
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gln Ile Gln Leu Gln Gln Ser Gly Pro Glu Val Val Lys Pro Gly
1               5                   10                  15

Ala Ser Val Lys Ile Ser Cys Lys Ala Ser Gly Tyr Thr Phe Thr Asp
            20                  25                  30

Tyr Tyr Ile Thr Trp Val Lys Gln Lys Pro Gly Gln Gly Leu Glu Trp
        35                  40                  45

Ile Gly Trp Ile Tyr Pro Gly Ser Gly Asn Thr Lys Tyr Asn Glu Lys
    50                  55                  60

Phe Lys Gly Lys Ala Thr Leu Thr Val Asp Thr Ser Ser Ser Thr Ala
65                  70                  75                  80

Phe Met Gln Leu Ser Ser Leu Thr Ser Glu Asp Thr Ala Val Tyr Phe
                85                  90                  95

Cys Ala Asn Tyr Gly Asn Tyr Trp Phe Ala Tyr Trp Gly Gln Gly Thr
            100                 105                 110

Gln Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
```

```
                    210                 215                 220
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Tyr Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Lys Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys Gly Gly Ser His His His
        435                 440                 445

His His His
    450

<210> SEQ ID NO 4
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Ile Val Leu Thr Gln Ser Pro Ala Ser Leu Ala Val Ser Leu
1               5                   10                  15

Gly Gln Arg Ala Thr Ile Ser Cys Lys Ala Ser Gln Ser Val Asp Phe
            20                  25                  30

Asp Gly Asp Ser Tyr Met Asn Trp Tyr Gln Gln Lys Pro Gly Gln Pro
        35                  40                  45

Pro Lys Val Leu Ile Tyr Ala Asn Leu Glu Ser Gly Ile Pro Ala Arg
    50                  55                  60

Phe Ser Gly Ser Gly Ser Gly Thr Asp Phe Thr Leu Asn Ile His Pro
65                  70                  75                  80

Val Glu Glu Glu Asp Ala Ala Thr Tyr Tyr Cys Gln Gln Ser Asn Glu
                85                  90                  95

Asp Pro Trp Thr Phe Gly Gly Gly Thr Lys Leu Glu Ile Lys Arg Thr
            100                 105                 110
```

```
Val Ala Ala Pro Ser Val Phe Ile Phe Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 5
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Asp Lys Gly Leu Glu Trp
        35                  40                  45

Val Ala Val Ile Trp Tyr Asp Gly Ser Asn Lys Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Leu Val Arg Gly Ala Met Tyr Gly Thr Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255
```

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser His His His His His His
    450                 455                 460

<210> SEQ ID NO 6
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Ser
            20                  25                  30

Trp Leu Ala Trp Tyr Gln Gln Lys Pro Glu Lys Ala Pro Lys Ser Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Ser Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser

```
145                 150                 155                 160
Gln Glu Ser Val Thr Glu Gln Asp Ser Lys Asp Ser Thr Tyr Ser Leu
                    165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taatacgact cactatagg                                              19

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctagttatt gctcagcg                                               18
```

What is claimed is:

1. An isolated antibody of the IgG class comprising a heavy chain and a light chain, wherein:
the heavy chain comprises at least one non-natural amino acid residue at a specific site selected from the group consisting of heavy chain residue 52 according to the Kabat numbering scheme and heavy chain residues 119, 222, and 241 according to the EU index of Kabat; or
the light chain comprises a non-natural amino acid residue at the light chain residue 152; or a combination thereof; or an aglycosylated variant thereof,
wherein each non-natural amino acid residue is independently selected from the group consisting of ortho-substituted tyrosine, meta substituted tyrosine, para-substituted phenylalanine, ortho-substituted phenylalanine, and meta-substituted phenylalanine.

2. The antibody of claim 1, wherein the antibody is a glycosylated.

3. The antibody of claim 2, wherein the light chain is selected from X, and K.

4. The antibody of claim 2, that is of a class or subclass selected from the group consisting of IgG1, IgG2, IgG3, and IgG4.

5. The antibody of claim 2,. wherein said non-natural amino acid residue comprises a moiety selected from the group consisting of amino, carboxy, acetyl, hydrazino, hydrazido, semicarbazido, sulfanyl, azido and alkynyl.

6. The antibody of claim 2, wherein each non-natural amino acid residue is according to the formula

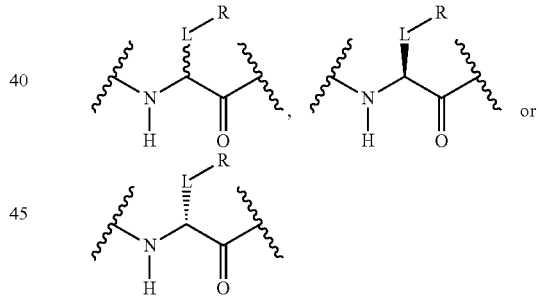

wherein each L is independently a phenylene; and
each R is independently a functional group selected from the group consisting of a therapeutic moiety, a labeling moiety, amino, carboxy, acetyl, hydrazino, hydrazido, semicarbazido, sulfanyl, azido, and alkynyl.

7. The antibody of claim 2, wherein the non-natural amino acid residue is selected from the group consisting of p-acetyl-L-phenylalanine, O-methyl-L-tyrosine, 3-methyl-phenylalanine, O-4-allyl-L-tyrosine, 4-propyl-L-tyrosine, fluorinated phenylalanine, isopropyl-L-phenylalanine, p-azido-L-phenylalanine, p-acyl-L-phenylalanine, p-benzoyl-L-phenylalanine, p-iodo-phenylalanine, p-bromophenylalanine, p-amino-L-phenylalanine, isopropyl-L-phenylalanine, p-propargyloxy-phenylalanine, and p-azidomethyl-L-phenylalanine.

8. The antibody of claim 2, wherein the non-natural amino acid residue is p-azido-L-phenylalanine.

9. The antibody of claim 2, wherein the non-natural amino acid residue is p-azidomethyl-L-phenylalanine.

10. An antibody conjugate comprising the antibody of claim 2 linked to one or more therapeutic moieties or labeling moieties, wherein at least one therapeutic moiety or labeling moiety is linked to one of the non-natural amino acids, or a residue thereof.

11. The antibody conjugate of claim 10, wherein said antibody is linked to one or more drugs or polymers.

12. The antibody conjugate of claim 10, wherein said antibody is linked to one or more labeling moieties.

13. The antibody conjugate of claim 10, wherein said antibody is linked to one or more single chain binding domains (scFvs).

14. The antibody conjugate of claim 10, wherein said at least one therapeutic or labeling moiety is linked to the non-natural amino acid, or a residue thereof, via one or more linkers.

15. A composition comprising the antibody of claim 2, wherein said composition is substantially pure.

16. A composition comprising the antibody of claim 2, wherein said antibody is at least 95% by mass of the total antibody mass of said composition.

* * * * *